United States Patent
Itami et al.

(10) Patent No.: US 9,056,822 B2
(45) Date of Patent: Jun. 16, 2015

(54) METHOD FOR PRODUCING POLYCYCLIC AROMATIC COMPOUND SUBSTITUTED BY ARYL GROUP

(75) Inventors: Kenichiro Itami, Nagoya (JP); Kenji Mochida, Nagoya (JP); Katsuaki Kawasumi, Nagoya (JP); Yasutomo Segawa, Nagoya (JP); Tomonori Kajino, Nagoya (JP)

(73) Assignee: National University Corporation Nagoya University, Nagoya-shi (JP)

( * ) Notice: Subject to any disclaimer, the term of this patent is extended or adjusted under 35 U.S.C. 154(b) by 0 days.

(21) Appl. No.: 14/125,119

(22) PCT Filed: Jun. 8, 2012

(86) PCT No.: PCT/JP2012/064845
§ 371 (c)(1),
(2), (4) Date: Mar. 6, 2014

(87) PCT Pub. No.: WO2012/169635
PCT Pub. Date: Dec. 13, 2012

(65) Prior Publication Data
US 2014/0206908 A1    Jul. 24, 2014

(30) Foreign Application Priority Data

Jun. 10, 2011 (JP) .................................. 2011-130547

(51) Int. Cl.
| | |
|---|---|
| *C07C 2/86* | (2006.01) |
| *C07C 2/66* | (2006.01) |
| *C07C 41/30* | (2006.01) |
| *C07C 43/21* | (2006.01) |
| *C07C 17/263* | (2006.01) |
| *C07C 17/361* | (2006.01) |

(52) U.S. Cl.
CPC . *C07C 41/30* (2013.01); *C07C 2/66* (2013.01); *C07C 43/21* (2013.01); *C07C 2/86* (2013.01); *C07C 17/263* (2013.01); *C07C 2103/40* (2013.01); *C07C 2103/50* (2013.01); *C07C 2103/54* (2013.01); *C07C 17/361* (2013.01)

(58) Field of Classification Search
None
See application file for complete search history.

(56) References Cited

U.S. PATENT DOCUMENTS

| | | | |
|---|---|---|---|
| 2004/0076853 | A1 | 4/2004 | Jarikov |
| 2006/0043858 | A1 | 3/2006 | Ikeda et al. |
| 2010/0048904 | A1 | 2/2010 | Koenemann et al. |
| 2010/0187505 | A1 | 7/2010 | Stoessel et al. |
| 2010/0258791 | A1 | 10/2010 | Iwakuma et al. |

FOREIGN PATENT DOCUMENTS

| | | |
|---|---|---|
| JP | 10-189248 A | 7/1998 |
| JP | 2008-270397 A | 11/2008 |
| JP | 2009-016693 A | 1/2009 |
| JP | 2010-222261 A | 10/2010 |
| JP | 2010-222268 A | 10/2010 |
| JP | 2010-238924 A | 10/2010 |
| WO | WO-2004/018587 A1 | 3/2004 |

OTHER PUBLICATIONS

Takanori Matsuda et al., "Synthesis of Pyrenes by Twofold Hydroarylation of 2,6-Dialkynylbiphenyls," Chemistry Letters, 2011, vol. 40, pp. 40-41.
Zong-Fan Duan et al., "A Novel Thiophene-Fused Polycyclic Aromatic with a Tetracene Core: Synthesis, Characterization, Optical and Electrochemical Properties," Molecules, 2011, vol. 16, pp. 4467-4481, Scheme 1.
Abdelaziz Jouaiti et al., "Molecular Tectonics: Design of 1-D Coordination Networks Based on Pyrene Bearing Pyrazolyl Units" European Journal of Inorganic Chemistry, 2003, No. 1, pp. 57-61, Scheme 1.
Domingo Garcia-Cuadrado et al., "Proton Abstraction Mechanism for the Palladium-Catalyzed Intramolecular Arylation," Journal of the American Chemical Society, 2006, vol. 128, pp. 1066-1067, Table 1.
Chemical Abstracts, 1951, vol. 45, No. 16, the abstract No. 7094e-i, 7095a and a cover page.
Ute Anton et al., "Synthesis of n-Alkyl-Substituted Perylenes and Terrylenes via Alkali-Metal Induced Cyclization of Oligonaphthylenes," Chemische Berichte, 1992, vol. 125, No. 10, pp. 2325-2330.
Kenji Mochida et al., "Direct Arylation of Polycyclic Aromatic Hydrocarbons through Palladium Catalysis," Journal of the American Chemical Society, 2011, vol. 133, pp. 10716-10719.
Lutz Ackermann et al., "Transition-Metal-Catalyzed Direct Arylation of (Hetero)Arenes by C—H Bond Cleavage," Angewandte Chemie International Edition, 2009, vol. 48, No. 51, pp. 9792-9826.
Xiao Chen et al., "Palladium(II)-Catalyzed C—H Activation/C—C Cross Coupling Reactions: Versatility and Practicality," Angewandte Chemie International Edition, 2009, vol. 48, No. 28, pp. 5094-5115.
Hiroshi Kawai et al., "Direct C—H bond arylation of arenes with aryltin reagents catalysed by palladium complexes," Chemical Communications, 2008, vol. 12, pp. 1464-1466.

(Continued)

*Primary Examiner* — Brian J Davis
(74) *Attorney, Agent, or Firm* — Locke Lord LLP; James E. Armstrong, IV

(57) ABSTRACT

PAH is subjected to C—H/C—B coupling using a specific boron compound, a palladium compound, and o-chloranil to produce a compound in which a C—H bond of the PAH is directly arylated regioselectively in a simple manner. When the substrate and the boron compound are appropriately selected, a larger PAH can also be obtained by further performing an annulation reaction after the coupling reaction. Similarly, when PAH is subjected to C—H/C—H cross-coupling using a specific aromatic compound, a palladium compound, and o-chloranil, a compound in which a C—H bond of the PAH is directly arylated regioselectively can be produced in a simple manner. When the substrate and the aromatic compound are appropriately selected in this case, a larger PAH can also be obtained by further performing an annulation reaction after the cross-coupling reaction.

14 Claims, 7 Drawing Sheets

(56) References Cited

OTHER PUBLICATIONS

Hiroto Yoshida et al., "Platinum-catalysed diborylation of arynes: synthesis and reaction of 1,2-diborylarenes," Chemical Communications, 2010, vol. 46, No. 10, pp. 1763-1765.

Kenji Mochida et al., "Pd-catalyzed C—H/C—H Arylation of Polycyclic Aromatic Hydrocarbons," The 91st CSJ(the Chemical Society of Japan) Annual Meeting 2011, KoenYokoshu, 2011, p. 1436, 1C9-43 and cover pages.

Katsuaki Kawasumi et al., "Pd-catalyzed C—H/C—B Arylation of Polycyclic Aromatic Hydrocarbons," The 91st CSJ(the Chemical Society of Japan) Annual Meeting 2011, KoenYokoshu, 2011, p. 1437, 1 C9-44 and cover pages.

International Search Report dated Aug. 7, 2012 and Written Opinion, issued for PCT/JP2012/064845.

Kami L. Hull et al., "Catalytic and Highly Regioselective Cross-Coupling of Aromatic C—H Substrates," Journal of American Chemical Society, vol. 129, pp. 11904-11905, (2007).

Ying Rong et al., "Palladium(II)-Catalyzed Coupling of p-Xylene via Regioselective C-H Activation in TFA," Organometallics, vol. 26, No. 18, Aug. 1, 2007, pp. 4376-4378.

Supplementary European search report dated Mar. 13, 2015 for EP Patent Application No. 12797336.0.

METHOD FOR PRODUCING POLYCYCLIC AROMATIC COMPOUND SUBSTITUTED BY ARYL GROUP

TECHNICAL FIELD

The present invention relates to a method for producing a polycyclic aromatic compound substituted with an aryl group.

BACKGROUND ART

Graphene, which is a two-dimensional sheet of $sp^2$-bonded carbon atoms, has attracted tremendous attention in almost all scientific and technological fields. Because the shape, width, etc., of graphene determine the properties thereof, synthesis of structurally homogeneous graphene is one of the major objectives in this research field.

Polycyclic aromatic hydrocarbon (PAH) is expected to be a promising material for producing graphene, and there is a great potential demand for a simple and efficient method of synthesizing PAH derivatives. Transition-metal-catalyzed direct arylation of one or more C—H bonds of an aromatic ring is considered to be one of the simplest and most ideal methods of synthesizing PAH derivatives. From such a standpoint, direct arylation of C—H bonds of commercially available small PAHs, which can be performed by a simple method, is significantly useful for synthesizing large PAHs (Non-patent Literature 1 to 3). However, thus-far reported substrates applicable for direct arylation are mostly those having a heteroaromatic ring or a directing group, and there have been few reports concerning direct arylation of PAHs (Non-patent Literature 3).

CITATION LIST

Non-Patent Literature

NPL 1: Ackermann, L.; Vicente, R.; Kapdti, A. R. Angew. Chem., Int. Ed. 2009, 48, 9792.
NPL 2: Chen, X.; Engle, K. M.; Wang, D.-H.; Yu, J.-Q. Angew. Chem., Int. Ed. 2009, 48, 5094.
NPL 3: Kawai, H.; Kobayashi, Y.; Oi, S.; Inoue, Y. Chem. Commun. 2008, 1464.

SUMMARY OF INVENTION

Technical Problem

An object of the present invention is to provide a method for producing a polycyclic aromatic compound in which a C—H bond in a desired position is directly arylated can be produced in a simple manner.

Solution to Problem

In view of the above object, the inventors of the present invention conducted intensive research and found that when PAH is subjected to C—H/C—B coupling using a specific boron compound in the presence of a palladium compound and o-chloranil, a compound in which a C—H bond of the PAH is directly arylated regioselectively can be produced in a simple manner. When the substrate and the boron compound are appropriately selected, a larger PAH can also be obtained by further performing an annulation reaction after the coupling reaction. The present inventors further found that when PAH is subjected to C—H/C—H cross-coupling using a specific aromatic compound in the presence of a palladium compound and o-chloranil, a compound in which a C—H bond of the PAH is directly arylated regioselectively can also be similarly produced in a simple manner. The present invention was accomplished as a result of further research based on the above findings. Specifically, the present invention encompasses the inventions described in items 1 to 22 below.

Item 1. A method for producing a polycyclic aromatic compound substituted with at least one substituted or unsubstituted aryl group, the method comprising reacting a polycyclic aromatic compound with a substituted or unsubstituted aryl-containing boron compound in the presence of a palladium compound and o-chloranil.

Item 2. The method according to item 1, wherein at least one hydrogen atom bonded to $sp^2$ hybridized carbon atoms of the polycyclic aromatic compound is replaced by a substituted or unsubstituted aryl derived from the substituted or unsubstituted aryl-containing boron compound.

Item 3. The method according to item 1 or 2, wherein the substituted or unsubstituted aryl-containing boron compound is
an organic boron compound represented by Formula (A1):

[Chem. 1]

$$Ar-B\begin{matrix}OR^1\\OR^1\end{matrix} \quad (A1)$$

wherein Ar is substituted or unsubstituted $C_{6-50}$ aryl;
two $R^1$ may be the same or different, and each represents hydrogen or $C_{1-20}$ alkyl; or
two $R^1$ may bond to each other to form a ring with the adjacent —O—B—O—, and the ring may further have an aromatic ring fused thereto;
a cyclic organic boron compound represented by Formula (A2):

[Chem. 2]

$$(A2)$$

wherein three Ar may be the same or different, and each is as defined above; or
an ionic boron compound represented by Formula (A3):

[Chem. 3]

$$Ar-B^{\ominus}\begin{matrix}X\\X\\X\end{matrix} \ M^{\oplus} \quad (A3)$$

wherein Ar is as defined above; three X may be the same or different, and each represents halogen or substituted or unsubstituted $C_{6-50}$ aryl; and M is an alkali metal.

Item 4. The method according to any one of items 1 to 3, wherein the polycyclic aromatic compound substituted with at least one substituted or unsubstituted aryl group is a compound represented by Formula (D):

[Chem. 4]

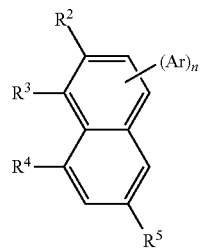

(D)

wherein $R^2$ to $R^5$ may be the same or different, and each represents hydrogen or $C_{1-20}$ alkyl, Ar represents substituted or unsubstituted $C_{6-50}$ aryl and may bond to any of the cyclic structures, n is an integer of 1 to 4, and one of the following requirements (1) to (4) is satisfied:

(1) $R^2$ to $R^5$ are each hydrogen;

(2) $R^2$ and $R^5$ are each hydrogen; $R^3$ and $R^4$ bond to each other to form a 5- or 6-membered unsaturated ring; and the unsaturated ring may further have a monocyclic or fused aromatic ring fused thereto;

(3) $R^2$ and $R^3$ bond to each other to form a substituted or unsubstituted aromatic ring; $R^4$ is hydrogen; and $R^5$ is hydrogen or $C_{1-20}$ alkyl;

(4) $R^2$ and $R^3$ bond to each other to form a substituted or unsubstituted aromatic ring; $R^3$ and $R^4$ bond to each other to form a substituted or unsubstituted aromatic ring; and $R^5$ is hydrogen or $C_{1-20}$ alkyl, and the polycyclic aromatic compound is a compound represented by Formula (B):

[Chem. 5]

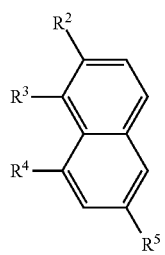

(B)

wherein $R^2$ to $R^5$ are as defined above.

Item 5. The method according to any one of items 1 to 4, wherein the palladium compound comprises zerovalent or divalent palladium.

Item 6. The method according to any one of items 1 to 5, wherein the reaction of the polycyclic aromatic compound with the substituted or unsubstituted aryl-containing boron compound is performed in the presence of a silver compound.

Item 7. A method for producing a compound having a structure represented by Formula (C):

[Chem. 6]

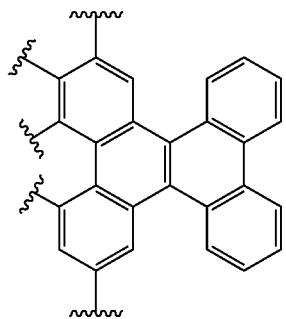

(C)

the method comprising the steps of:

(I) reacting a compound having a structure represented by Formula (B'):

[Chem. 7]

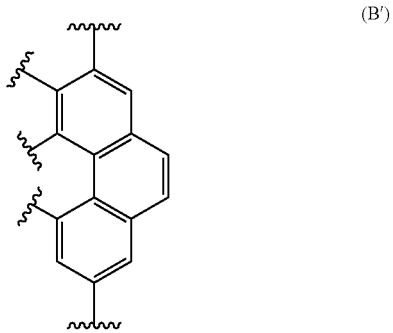

(B')

with a compound represented by Formula (G):

[Chem. 8]

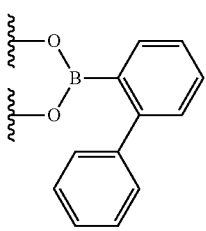

(G)

in the presence of a palladium compound and o-chloranil to produce a compound of Formula (D'):

[Chem. 9]

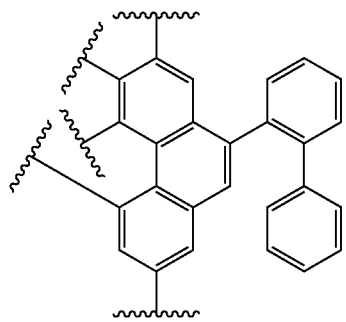
(D')

and, (II) subjecting the compound obtained in Step (I) to an annulation reaction.

Item 8. A method for producing a compound represented by Formula (C'):

[Chem. 10]

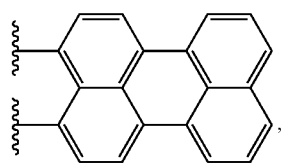
(C')

the method comprising the steps of:
(I) reacting a compound represented by Formula (B"):

[Chem. 11]

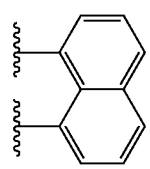
(B")

with a compound having a naphthalene skeleton in the presence of a palladium compound and o-chloranil to produce a compound having a structure represented by Formula (D"):

[Chem. 12]

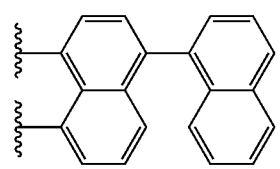
(D")

and (II) subjecting the compound obtained in Step (I) to an annulation reaction.

Item 9. The method according to item 7 or 8, wherein step (II) is a step of performing an oxidation reaction using $FeCl_3$.

Item 10. A method for producing a polycyclic aromatic compound substituted with at least one substituted or unsubstituted aryl group, the method comprising reacting a polycyclic aromatic compound with a substituted or unsubstituted aryl-containing compound in the presence of a palladium compound and o-chloranil.

Item 11. The method according to item 10, wherein at least one hydrogen atom bonded to $sp^2$ hybridized carbon atoms of the polycyclic aromatic compound is replaced by a substituted or unsubstituted aryl group derived from the substituted or unsubstituted aryl-containing compound.

Item 12. The method according to item 10 or 11, wherein the substituted or unsubstituted aryl-containing compound is an aryl-containing compound represented by Formula (E):

[Chem. 13]

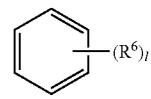
(E)

wherein l $R^6$s, wherein l is the number of $R^6$, may be the same or different, and each represents halogen, $C_{1-20}$ alkyl, $C_{1-20}$ alkoxy, $C_{3-50}$ cycloalkyl, or $C_{6-50}$ aryl; and l is an integer of 0 to 4), or an aryl-containing compound represented by Formula (E'):

[Chem. 14]

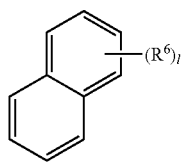
(E')

wherein $R^6$ and l are as defined above; and $R^6$ may bond to any of the benzene rings.

Item 13. The method according to any one of items 10 to 12, wherein the polycyclic aromatic compound substituted with at least one substituted or unsubstituted aryl group is represented by Formula (D):

[Chem. 15]

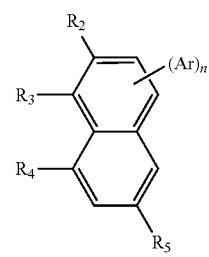
(D)

wherein $R^2$ to $R^5$ may be the same or different, and each represents hydrogen or $C_{1-20}$ alkyl, and Ar represents substituted or unsubstituted $C_{6-50}$ aryl and may bond to any of the cyclic structures, n is an integer of 1 to 4, and one of the following requirements (1) to (4) is satisfied:
(1) $R^2$ to $R^5$ are each hydrogen;
(2) $R^2$ and $R^5$ are each hydrogen: $R^3$ and $R^4$ bond to each other to form a 5- or 6-membered unsaturated ring; and the unsaturated ring may further have a monocyclic or fused aromatic ring fused thereto;

(3) $R^2$ and $R^3$ bond to each other to form a substituted or unsubstituted aromatic ring; $R^4$ is hydrogen; and $R^5$ is hydrogen or $C_{1-20}$ alkyl;

(4) $R^2$ and $R^3$ bond to each other to form a substituted or unsubstituted aromatic ring; $R^3$ and $R^4$ bond to each other to form a substituted or unsubstituted aromatic ring; and $R^5$ is hydrogen or $C_{1-20}$ alkyl and the polycyclic aromatic compound is a compound represented by Formula (B):

[Chem. 16]

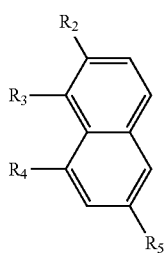

wherein $R^2$ to $R^5$ are as defined above.

Item 14. The method according to any one of items 10 to 13, wherein the reaction of the polycyclic aromatic compound with the aryl-containing compound is performed in the presence of a silver compound.

Item 15. The method according to item 14, wherein the silver compound is silver trifluoromethanesulfonate.

Item 16. A compound represented by Formula (F1a):

[Chem. 17]

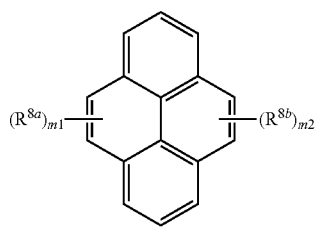
(F1a)

wherein $R^{8a}$ and $R^{8b}$ may be the same or different, and each represents a monocyclic or bicyclic aromatic group optionally substituted with 1 to 3 substituents selected from the group consisting of halogen atoms and fluorine-containing or fluorine-free $C_{1-20}$ alkyl groups (wherein the aromatic group is not phenyl); and m1 and m2 may be the same or different, and each is an integer of 0 to 2 (wherein m1+m2 is an integer of 1 to 4).

Item 17. A compound represented by Formula (F1b):

[Chem. 18]

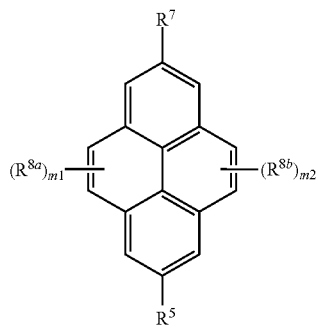

wherein $R^5$ and $R^7$ may be the same or different, and each represents hydrogen or $C_{1-20}$ alkyl (wherein at least one of $R^5$ and $R^7$ is alkyl); $R^{8a}$ and $R^{8b}$ may be the same or different, and each represents a monocyclic or bicyclic aromatic group optionally substituted with 1 to 3 substituents selected from the group consisting of halogen atoms and fluorine-containing or fluorine-free $C_{1-20}$ alkyl groups; and m1 and m2 may be the same or different, and each is an integer of 0 to 2 (wherein m1+m2 is an integer of 1 to 4).

Item 18. A compound represented by Formula (F2):

[Chem. 19]

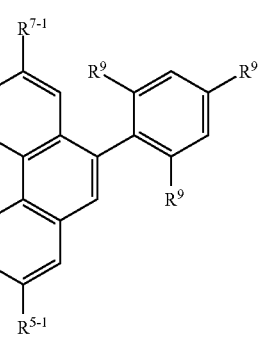
(F2)

wherein $R^{5-1}$ and $R^{7-1}$ may be the same or different, and each represents hydrogen or $C_{1-20}$ alkyl; $R^9$ may be the same or different, and each represents hydrogen, halogen, and fluorine-containing or fluorine-free $C_{1-20}$ alkyl, or a monocyclic or bicyclic aromatic group (wherein none or two of the three $R^9$ are hydrogen).

Item 19. A compound represented by Formula:

[Chem. 20]

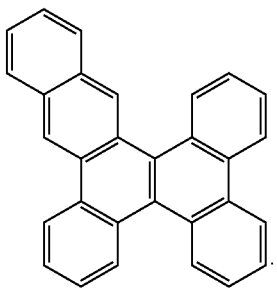

Item 20. A compound represented by Formula (F3):

[Chem. 21]

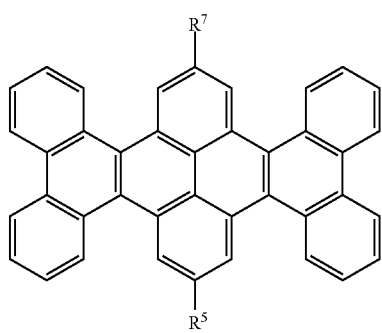

(F3)

wherein $R^5$ and $R^7$ may be the same or different, and each represents hydrogen or $C_{1-20}$ alkyl.

Item 21. A compound represented by Formula (F4):

[Chem. 22]

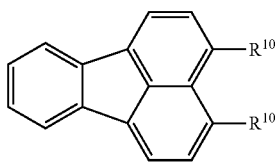

(F4)

wherein $R^{10}$ may be the same or different, and each represents a monocyclic or bicyclic aromatic ring optionally substituted with one to three substituents selected from the group consisting of halogen atoms and fluorine-containing or fluorine-free $C_{1-20}$ alkyl groups, or hydrogen (wherein none or one of the two $R^{10}$ is hydrogen); and two $R^{10}$ may bond to each other to form a ring.

Item 22. A compound represented by Formula (F5):

[Chem. 23]

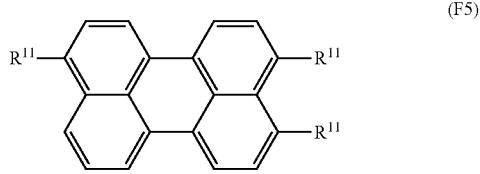

(F5)

wherein $R^{11}$ may be the same or different, and each represents a monocyclic or bicyclic aromatic group optionally substituted with one to three substituents selected from the group consisting of halogen atoms and fluorine-containing or fluorine-free $C_{1-20}$ alkyl groups.

Advantageous Effects of Invention

According to the present invention, PAH is subjected to C—H/C—B coupling using a specific boron compound, a palladium compound, and o-chloranil to produce a compound in which a C—H bond of the PAH is directly arylated regioselectively in a simple manner. For example, when pyrene is used as a typical example of PAH, the C—H bond in position 4 is arylated. When the substrate and the boron compound are appropriately selected, a larger PAH can also be obtained by further performing an annulation reaction after the coupling reaction. Similarly, when PAH is subjected to C—H/C—H cross-coupling using a specific aromatic compound, a palladium compound, and o-chloranil, a compound in which a C—H bond of the PAH is directly arylated regioselectively can be produced in a simple manner. When the substrate and the aromatic compound are appropriately selected in this case, a larger PAH can also be obtained by further performing an annulation reaction after the cross-coupling reaction.

DESCRIPTION OF EMBODIMENTS

1. First Embodiment C—H/C—B Coupling

Figure 1:
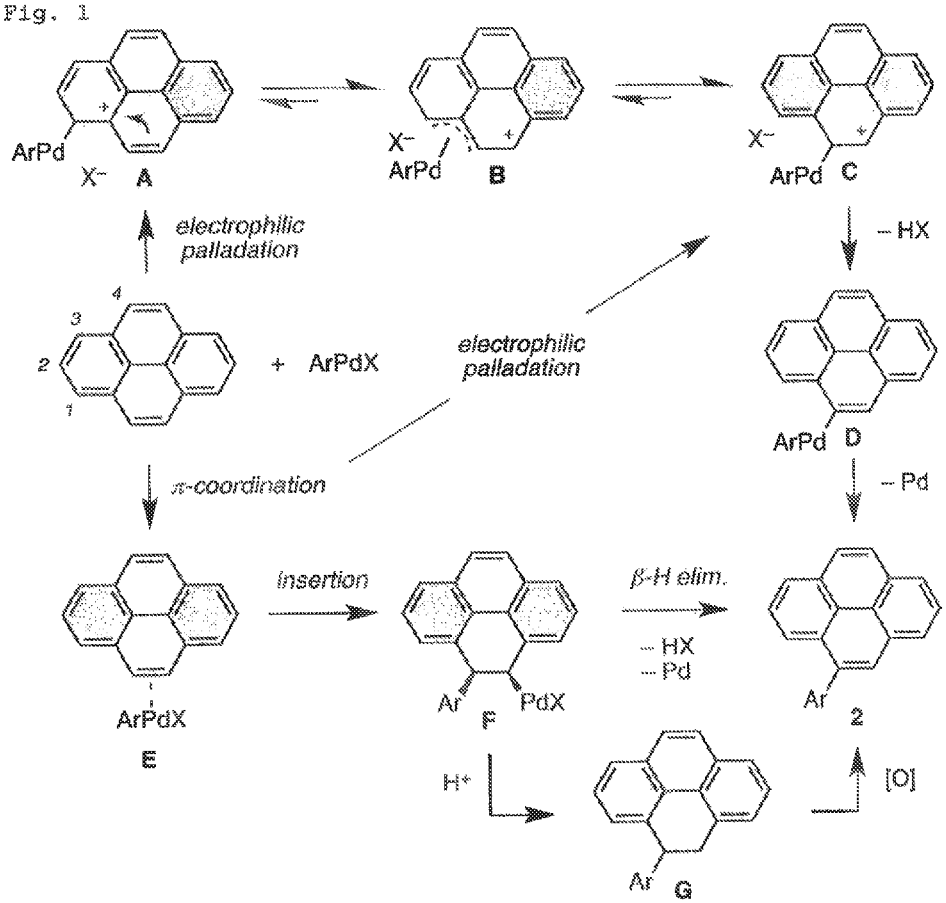
FIG. 1 is a conceptual diagram showing a projected reaction mechanism for the case in which pyrene is used as a substrate in the production method of the present invention.

The method for producing an aromatic compound according to the first embodiment of the present invention is such that a polycyclic aromatic compound is reacted with a substituted or unsubstituted aryl-containing boron compound in the presence of a palladium compound and o-chloranil to obtain a polycyclic aromatic compound substituted with at least one substituted or unsubstituted aryl group.

[1-1] Polycyclic Aromatic Compound

In the present invention, the target compound is obtained through the reaction shown in the reaction scheme below:

[Chem. 24]

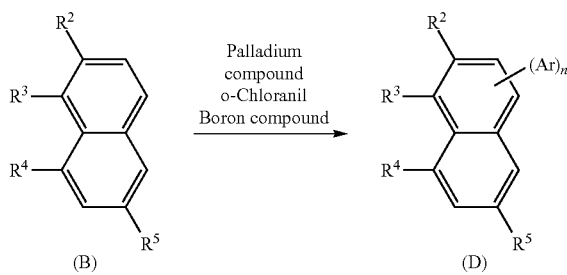

wherein $R^2$ to $R^5$ may be the same or different, and each represents hydrogen or $C_{1-20}$, in particular $C_{1-6}$ alkyl, Ar is a substituted or unsubstituted $C_{6-50}$ aryl, n is an integer of 1 to 4, Ar may bond to any of the cyclic structures, and satisfies any one of the requirements described in (1) to (4) below.

(1) $R^2$ to $R^5$ are each hydrogen.
(2) $R^2$ and $R^5$ are each hydrogen; $R^3$ and $R^4$ bond to each other to form a 5- or 6-membered unsaturated ring; and the unsaturated ring may further have a monocyclic or fused aromatic ring fused thereto.
(3) $R^2$ and $R^3$ bond to each other to form a substituted or unsubstituted aromatic ring; $R^4$ is hydrogen; and $R^5$ is hydrogen or $C_{1-20}$, in particular $C_{1-6}$ alkyl.
(4) $R^2$ and $R^3$ bond to each other to form a substituted or unsubstituted aromatic ring; $R^3$ and $R^4$ bond to each other to form a substituted or unsubstituted aromatic ring; and $R^5$ is hydrogen or $C_{1-20}$, in particular $C_{1-6}$ alkyl.

In the present invention, the polycyclic aromatic compound that is used as a substrate is not particularly limited, as long as it has a structure in which two or more rings are fused. Specifically, polycyclic aromatic compounds represented by Formula (B) are preferable:

[Chem. 25]

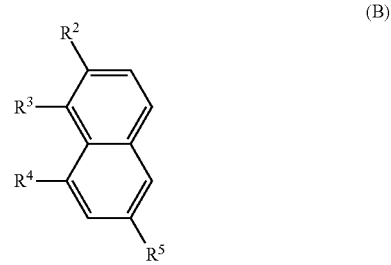

wherein $R^2$ to $R^5$ are as defined above.

More specifically, the polycyclic aromatic compound used in the present invention preferably has at least a naphthalene skeleton.

Polycyclic Aromatic Compound (B1)

Among polycyclic aromatic compounds (B), polycyclic aromatic compound (B1) satisfies requirement (1) below, and is naphthalene. In this case, an arylated naphthalene is obtained by the reaction scheme shown below:

[Chem. 26]

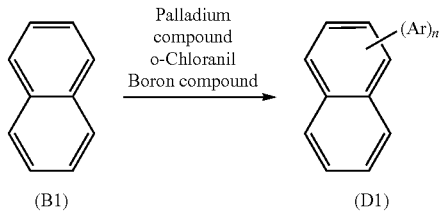

wherein Ar and n are as defined above; and Ar may bond to either of the two benzene rings.

In aromatic compound (D1), Ar is a substituted or unsubstituted aryl that is derived from the boron compound described later. The Ar has 6 to 50 carbon atoms and may have one or more substituents. Specific examples of the aryl groups include phenyl, naphthyl, anthranil, phenanthrenyl, and biphenyl groups. Among these, phenyl is preferable. Examples of the substituents that may be contained in the aryl include halogen atoms (such as F, Cl, and Br); $C_{1-20}$, in particular $C_{1-6}$ alkyl groups (such as methyl, ethyl, and perfluoromethyl) optionally having halogen atoms; and $C_{1-20}$, in particular $C_{1-6}$ alkoxy groups (such as methoxy) optionally having halogen. The number of substituents is not particularly limited, and is preferably 1 to 3.

Specific examples of such aryl groups (Ar) include:

[Chem. 27]

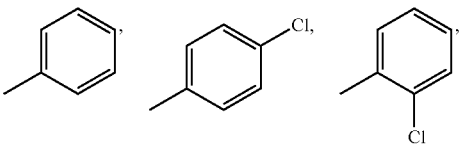

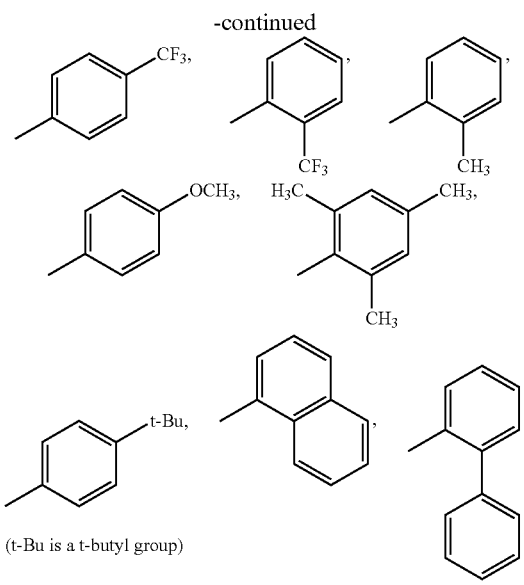

(t-Bu is a t-butyl group)

Polycyclic Aromatic Compound (B2)

Among the polycyclic aromatic compounds (B), polycyclic aromatic compound (B2) satisfies requirement (2). Specific examples thereof include compounds represented by formula (B2):

[Chem. 28]

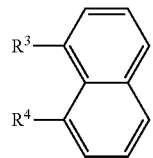

(B2)

wherein $R^3$ and $R^4$ are as defined in (2) of formula (B) above.

In this case, an aromatic compound arylated by the reaction shown in the reaction scheme below is obtained:

[Chem. 29]

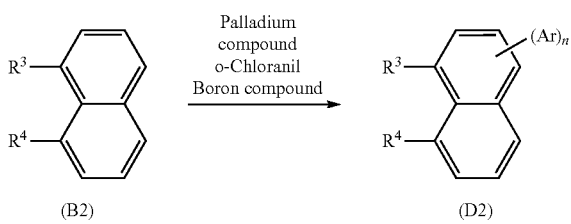

wherein $R^3$ and $R^4$ are as defined in (2) of Formula (B) above; Ar and n are as defined above; and Ar may bond to any of the cyclic structures.

$R^3$ and $R^4$ bond to each other to form a 5- or 6-membered unsaturated ring. Considering the fact that the aromatic compound obtained by the production method of the present invention is used as a precursor of graphene, a 6-membered unsaturated ring (e.g., benzene ring) is preferable.

The unsaturated ring formed by bonding $R^3$ and $R^4$ may further have a monocyclic or fused aromatic ring fused thereto. The aromatic ring preferably has 6 carbon atoms. A specific example of the monocyclic aromatic rings includes benzene ring. Specific examples of the fused aromatic rings include naphthalene ring, phenanthrene ring, and anthracene ring.

Specific examples of such polycyclic aromatic compounds (B2) include perylene represented by the formula below:

[Chem. 30]

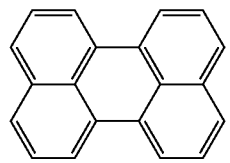

and fluoranthene represented by the formula below:

[Chem. 31]

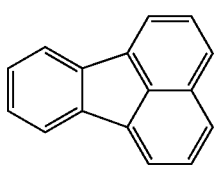

When perylene is used, it is possible to obtain an aromatic compound as represented by Formula (D2a) in which four hydrogen atoms are regioselectively substituted with an aryl group for each:

[Chem. 32]

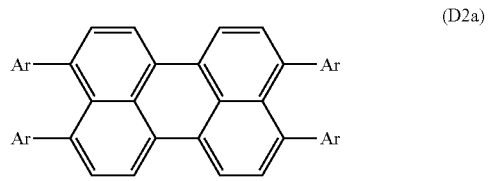

(D2a)

wherein four Ar may be the same or different, and each is as defined above.

Polycyclic Aromatic Compound (B3)

Among polycyclic aromatic compounds (B), polycyclic aromatic compound (B3) satisfies requirement (3). Specific examples thereof include compounds represented by Formula (B3):

[Chem. 33]

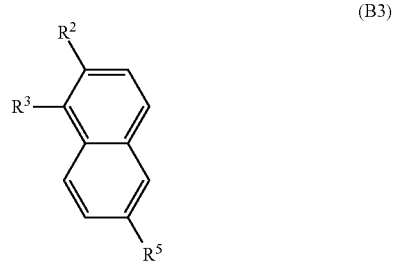

(B3)

wherein $R^2$, $R^3$, and $R^5$ are as defined in (3) of Formula (B).

In this case, an arylated aromatic compound can be obtained by the reaction shown below:

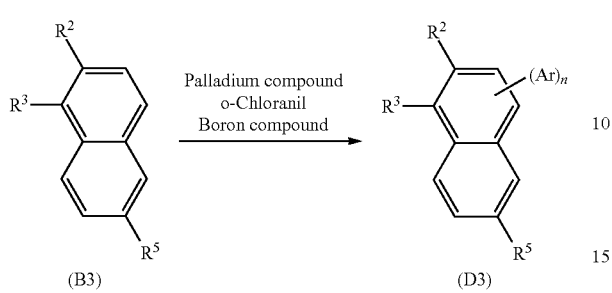

wherein $R^2$, $R^3$, and $R^5$ are as defined in (3) of Formula (B); Ar and n are as defined above; and Ar may bond to any of the cyclic structures.

$R^2$ and $R^3$ bond to each other to form a substituted or unsubstituted aromatic ring. The aromatic ring preferably has 6 to 12 carbon atoms. In this case, examples of the aromatic rings to be fused include benzene ring and naphthalene ring.

Examples of the substituents that may be contained in the aromatic ring include halogen atoms (such as F, Cl, and Br); and $C_{1-20}$, in particular $C_{1-6}$ alkyl optionally having halogen. The number of substituents is not particularly limited, and is preferably 1 to 6.

$R^5$ is hydrogen or $C_{1-20}$, in particular $C_{1-6}$ alkyl. Specific examples thereof include hydrogen atom, methyl, ethyl, isopropyl, n-propyl, t-butyl, and n-hexyl groups.

Specific examples of such polycyclic aromatic compounds (B3) include compounds represented by the formulas below:

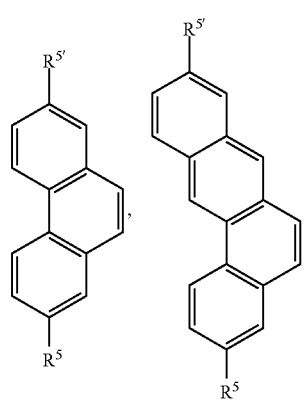

wherein $R^5$ is as defined above; $R^{5'}$ is defined in the same manner as $R^5$, and $R^5$ and $R^{5'}$ may be the same or different.

Polycyclic Aromatic Compound (B4)

Among the polycyclic aromatic compounds (B), polycyclic aromatic compound (B4) satisfies requirement (4). Specific examples thereof include compounds represented by Formula (B4):

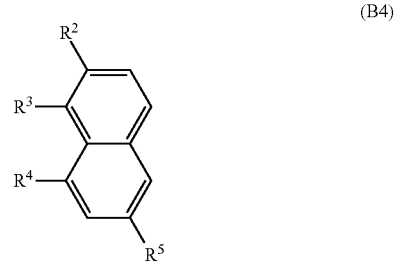

wherein $R^2$ to $R^5$ are as defined in (4) of Formula (B):

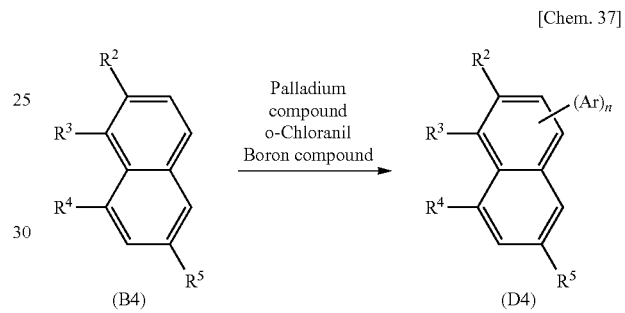

wherein $R^2$ to $R^5$ are as defined in (4) of Formula (B); Ar and n are as defined above; and Ar may bond to any of the cyclic structures.

$R^2$ and $R^3$ bond to each other to form a substituted or unsubstituted aromatic ring. The aromatic ring preferably has 6 to 12 carbon atoms. In this case, examples of the aromatic rings to be fused include benzene ring and naphthalene ring.

Examples of the substituents that may be contained in the aromatic ring include halogen atoms (such as F, Cl, and Br), and $C_{1-20}$, in particular $C_{1-6}$ alkyl optionally having halogen. The number of substituents is not particularly limited, and is preferably 1 to 6.

$R^3$ and $R^4$ bond to each other to form a substituted or unsubstituted aromatic ring. The aromatic ring preferably has 6 carbon atoms. In this case, one example of the aromatic ring is benzene ring.

Examples of the substituents that may be contained in the aromatic ring include halogen atoms (such as F, Cl, and Br), and $C_{1-20}$, in particular $C_{1-6}$ alkyl optionally having halogen. The number of substituents is not particularly limited, and is preferably 1 to 6.

$R^5$ is hydrogen or a $C_{1-20}$, in particular $C_{1-6}$ alkyl. Specific examples thereof include hydrogen atom, methyl, ethyl, isopropyl, n-propyl, t-butyl, and n-hexyl groups.

Specific examples of such polycyclic aromatic compounds (B4) include compounds represented by the formula below:

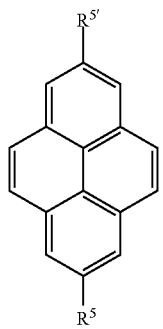

($R^5$ and $R^{5'}$ are as defined above).

[1-2] Boron Compound

The boron compound used in the present invention contains a substituted or unsubstituted aryl group. The substituted or unsubstituted aryl group is the same as the above-mentioned Ar, and examples, etc., of the aryl group are also the same as above.

The boron compound having such an aryl group may be, for example, an organic boron compound represented by Formula (A1):

[Chem. 39]

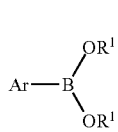
(A1)

wherein Ar is as defined above; two $R^1$ may be the same or different, and each represents hydrogen or $C_{1-20}$, particularly $C_{1-6}$, alkyl; two $R^1$ may bond to each other to form a ring with the adjacent —O—B—O—, and the ring may further have an aromatic ring fused thereto;

a cyclic organic boron compound represented by Formula (A2):

[Chem. 40]

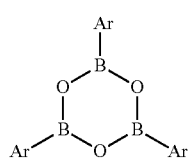
(A2)

wherein three Ar may be the same or different, and each is as defined above; or
an ionic boron compound represented by Formula (A3):

[Chem. 41]

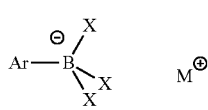
(A3)

wherein Ar is as defined above; three X may be the same or different, and each is halogen, substituted or unsubstituted $C_{6-50}$ aryl; and M is an alkali metal.

Organic Boron Compound (A1)

In the organic boron compound (A1), two $R^1$ each represent hydrogen or $C_{1-20}$, preferably $C_{1-6}$, alkyl. Two $R^1$ may be the same or different. When $R^1$ is alkyl, carbon atoms of alkyl groups may bond to each other to form a ring with boron and oxygen atoms.

When two $R^1$ form a ring, examples of the rings formed are as follows.

[Chem. 42]

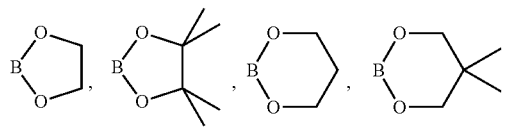

Such a ring may further have an aromatic ring fused thereto. Such an aromatic ring preferably has 6 carbon atoms, and a specific example thereof is a benzene ring or the like.

Examples of the boron compound (A1) include

[Chem. 43]

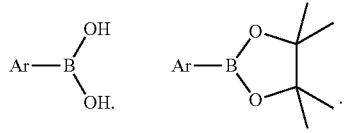

(Ar is as defined above)  (Ar is as defined above)

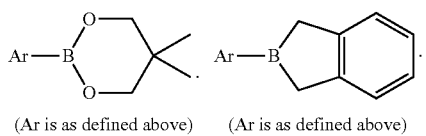

(Ar is as defined above)  (Ar is as defined above)

In this case, from the viewpoint of obtaining in a high yield an aromatic compound regioselectively substituted with substituted or unsubstituted aryl and suppressing the production of by-products, the amount of boron compound (A1) used is typically 1 to 6 mol, and preferably 1.5 to 2.5 mol, per mol of the polycyclic aromatic compound (B).

Cyclic Organic Boron Compound (A2)

Specific examples of the cyclic organic boron compound (A2) include the following.

[Chem. 44]

(Ph is phenyl).

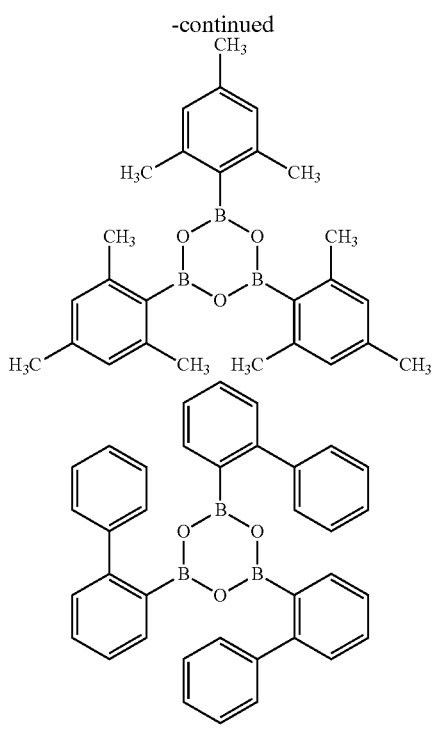

In this case, from the viewpoint of obtaining in a high yield an aromatic compound regioselectively substituted with substituted or unsubstituted aryl and suppressing the production of by-products, the amount of boron compound (A2) used is typically 0.33 to 2 mol, and preferably 0.5 to 0.83 mol, per mol of the polycyclic aromatic compounds (B).

Ionic Boron Compound (A3)

In the ionic boron compound (A3), three X may be the same or different, and each represents halogen or substituted or unsubstituted $C_{6-50}$ aryl. Specific examples thereof include fluorine, chlorine, bromine, iodine, phenyl, and the like. Among these, fluorine is preferable.

M represents an alkali metal. Specific examples thereof include lithium, potassium, sodium, and the like. Among these, potassium is preferable.

Specific examples of the ionic boron compound (A3) include the following compounds.

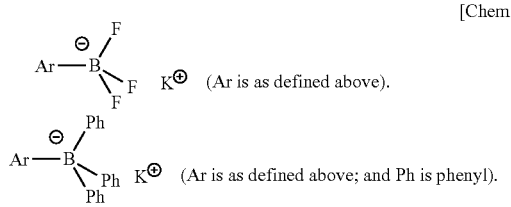

[Chem. 45]

(Ar is as defined above).

(Ar is as defined above; and Ph is phenyl).

In this case, from the viewpoint of obtaining in a high yield an aromatic compound regioselectively substituted with substituted or unsubstituted aryl and suppressing the production of by-products, the amount of boron compound (A3) used is typically 1 to 6 mol, and preferably 1.5 to 2.5 mol, per mol of the polycyclic aromatic compounds (B).

[1-3] Palladium Compound

In the first embodiment of the present invention, the reaction is generally performed in the presence of a palladium compound. Examples of the palladium compounds include known palladium compounds used as a catalyst for synthesizing organic compounds (including polymers). The palladium compounds may be either a compound containing a zerovalent palladium, or a compound containing a divalent palladium. When a compound containing a zerovalent palladium is used, the zerovalent palladium is oxidized in the system to form a divalent palladium. Specific examples of the usable palladium compounds include Pd(OAc)$_2$ (Ac is acetyl), PdCl$_2$, PdBr$_2$, PdI$_2$, and Pd(OTf)$_2$ (Tf is trifluoromethylsulfonyl). Pd(OAc)$_2$ is preferably used in the present invention.

In the first embodiment of the present invention, the amount of palladium compound is, in terms of the yield, typically 0.01 to 0.5 mol and preferably 0.025 to 0.2 mol, per mol of polycyclic aromatic compound (B), which is the starting material.

In the first embodiment of the present invention, a ligand that is capable of coordinating with the palladium atom, which is the central element of the palladium compound, may be combined, if necessary. However, ligands lose their coordinative ability when oxidized due to the oxidizing power of the o-chloranil described later; therefore, when a ligand is used, it is desirable to use a ligand that is strong against oxidation. Examples of such ligands include phosphate-based ligands such as triphenyl phosphite, triisopropyl phosphite, tris(2,2,2-trifluoroethyl)phosphite, and tris(1,1,1,3,3, 3-hexafluoro isopropyl)phosphite.

In the first embodiment of the present invention, when one or more ligands are used, the amount thereof is, in terms of the yield, typically 0.01 to 0.5 mol and preferably 0.025 to 0.2 mol, per mol of polycyclic aromatic compound (B), which is the starting material.

[1-4] o-Chloranil

In the first embodiment of the present invention, o-chloranil is used as an oxidant. The o-chloranil is represented by the formula below:

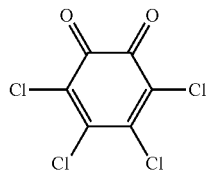

[Chem. 46]

In the first embodiment of the present invention, by the use of o-chloranil as an oxidant, the yield can be improved and the production of by-products such as biphenyl can be suppressed.

The yield can also be improved when 3,5-di-tert-butyl-1, 2-benzoquinone represented by the following formula is used as an oxidant.

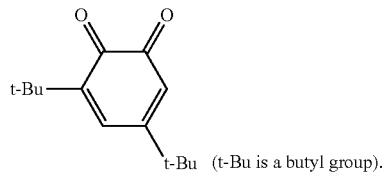

[Chem. 47]

(t-Bu is a butyl group).

However, in this case, a large amount of biphenyl, which is a byproduct, is produced. Furthermore, the yield is also lower compared to the case where o-chloranil is used.

Even if p-chloranil having a structure shown below,

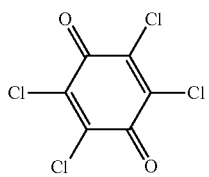

[Chem. 48]

which is similar to that of o-chloranil, is used as an oxidant, the yield cannot be improved.

For the reasons described above, the use of o-chloranil as an oxidant makes it possible, for the first time, to arylate the C—H bonds of a polycyclic aromatic compound in a simple manner.

The amount of o-chloranil is, in terms of the yield, typically 1 to 5 mol and preferably 1 to 2 mol, per mol of polycyclic aromatic compound (B).

[1-5] Silver Compound

In the first embodiment of the present invention, a silver compound may be co-present in the reaction between the polycyclic aromatic compound (B) and substituted or unsubstituted aryl-containing boron compound (A). This can accelerate the reaction.

Examples of such silver compounds include AgOTf (Tf is trifluoromethylsulfonyl), $AgBF_4$, $AgPF_6$, $AgSbF_6$, AgTFA (silver trifluoroacetate), AgOAc (Ac is acetyl), $Ag_2CO_3$, and AgF.

In the first embodiment of the present invention, the amount of silver compound is, in terms of the yield, typically 0.01 to 1 mol and preferably 0.025 to 0.4 mol, per mol of the polycyclic aromatic compound (B), which is the starting material.

[1-6] Reaction Conditions

The reaction of the first embodiment of the present invention is typically performed in the presence of a reaction solvent. Examples of the reaction solvents include aliphatic hydrocarbons such as hexane, cyclohexane, and heptane; aromatic hydrocarbons such as toluene, xylene, benzene, chlorobenzene, o-dichlorobenzene, m-dichlorobenzene and p-dichlorobenzene; esters such as methyl acetate, ethyl acetate and butyl acetate; cyclic ethers such as diethyl ether, tetrahydrofuran, dioxane, dimethoxyethane and diisopropyl ether; halogenated hydrocarbons such as 1,2-dichloroethane (1,2-DCE), methyl chloride, chloroform, dichloromethane, dichloroethane and dibromoethane; ketones such as acetone and methyl ethyl ketone; amides such as dimethylformamide and dimethylacetamide; nitriles such as acetonitrile; alcohols such as methanol, ethanol and isopropyl alcohol; and dimethyl sulfoxide. These solvents may be used singly, or in a combination of two or more. Among these, in the present invention, 1,2-dichloroethane (1,2-DCE), chlorobenzene, o-dichlorobenzene, m-dichlorobenzene, p-dichlorobenzene, dimethoxyethane, and the like, are preferable.

The reaction temperature of the reaction in the first embodiment of the present invention is typically selected from the range of 20° C. or higher and a temperature not higher than the boiling point of the reaction solvent mentioned above. In view of the yield and site-selectivity, the reaction temperature is preferably in the range of about 70 to 90° C.

The reaction pressure is not particularly limited, and may be about atmospheric pressure.

The reaction atmosphere is not particularly limited, and is preferably an inert gas atmosphere selected from an argon gas atmosphere, nitrogen gas atmosphere, or the like.

By setting the reaction conditions as described above, at least one hydrogen atom bonded to $sp^2$ hybridized carbon atoms of the polycyclic aromatic compound (B), which is the starting material, will be replaced by an aryl group derived from boron compound (A) in a site-selective manner.

[1-7] Reaction Mechanism

The reaction mechanism in the present invention is not necessarily clear, but is presumably as shown in FIG. 1. For the sake of convenience, the reaction mechanism is explained below using pyrene as an example of the substrate polycyclic aromatic compound (B).

Reaction Mechanism 1 (Route of the Top Row in FIG. 1)

First, an ArPd species (wherein Ar is as defined above) produced using the boron compound (A) or the aryl group contained in the boron compound electrophilically attacks position 1 of pyrene to produce an intermediate shown as A in FIG. 1. Thereafter, an intermediate shown as C is produced from the intermediate A via an intermediate B by σ->π->σ isomerization. The intermediate C is considered to be the most thermodynamically stable due to its resonance stabilization effect. Further, the intermediate C is deprotonated into an intermediate shown as D. Finally, the intermediate D is converted into pyrene 2 selectively arylated in position 4 by reductive elimination from Pd.

Reaction Mechanism 2 (Route Obliquely Upward from the Bottom Left of FIG. 1)

First, an intermediate shown as E is produced by π interaction of an ArPd species with the double bond in positions 4 and 5 (K-region) of pyrene. Then, Pd electrophilically migrates from the intermediate E to position 4 to produce an intermediate shown as C. Then, pyrene 2 selectively arylated in position 4 is obtained in the same manner as in the above reaction mechanism 1.

Reaction Mechanism 3 (Route of the Bottom Row of FIG. 1)

First, an intermediate shown as E is produced in the same manner as in the above reaction mechanism 2. Then, an intermediate shown as F is produced by an Ar/Pd insertion reaction (Heck reaction). At this time, Pd is considered to be selectively added to position 4. Further, by β hydrogen desorption (or an oxidation reaction after Pd desorption by protonation), pyrene selectively arylated in position 4 is obtained.

Among the compounds produced by the reactions according to the first embodiment of the present invention, compounds represented by Formula (F1a), which are obtained by using the compound of Formula (B) that satisfies requirement (4), are novel compounds that are not disclosed in any documents.

[Chem. 49]

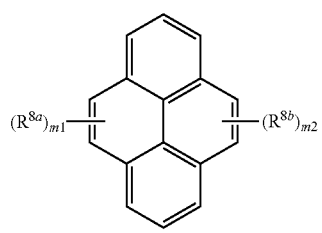

(F1a)

wherein $R^{8a}$ and $R^{8b}$ may be the same or different, and each represents a monocyclic or bicyclic aromatic group optionally substituted with 1 to 3 substituents selected from the group consisting of halogen atoms and fluorine-containing or fluorine-free $C_{1-20}$, particularly $C_{1-6}$, alkyl groups (wherein the aromatic group is not phenyl); and m1 and m2 may be the same or different, and each is an integer of 0 to 2 (wherein m1+m2 is an integer of 1 to 4).

The compound of Formula (F1a) is preferably, for example, a compound represented by Formula (F1a-1):

[Chem. 50]

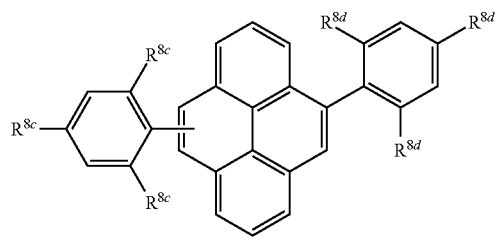

(F1a-1)

wherein three $R^{8c}$ and three $R^{8d}$ may be the same or different, and $R^{8c}$ and $R^{8d}$ may be the same or different, and each represents hydrogen or fluorine-containing or fluorine-free $C_{1-20}$, particularly $C_{1-6}$, alkyl, or a monocyclic or bicyclic aromatic group (wherein none or two of the three $R^{8c}$ are hydrogen, and none or two of the three $R^{8d}$ are hydrogen), or a compound represented by Formula (F1a-2):

[Chem. 51]

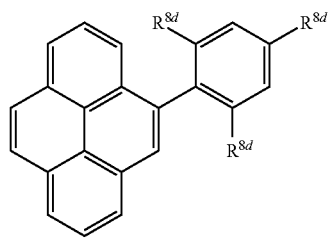

(F1a-2)

wherein $R^{8d}$ is as defined above.

The compounds shown in the Examples below are particularly preferable.

Among the compounds produced by the reactions according to the first embodiment of the present invention, compounds represented by Formula (F1b), which are obtained by using the compound of Formula (B) that satisfies requirement (4), are novel compounds that are not disclosed in any documents.

[Chem. 52]

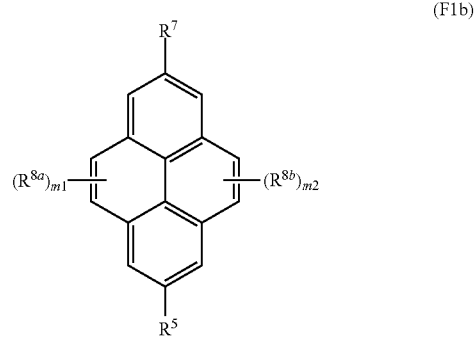

(F1b)

wherein $R^5$ and $R^7$ may be the same or different, and each represents hydrogen or $C_{1-20}$, particularly $C_{1-6}$, alkyl (wherein at least one of $R^5$ and $R^7$ is alkyl); $R^{8a}$ and $R^{8b}$ may be the same or different, and each represents a monocyclic or bicyclic aromatic group optionally substituted with 1 to 3 substituents selected from the group consisting of halogen atoms and fluorine-containing or fluorine-free $C_{1-20}$ particularly $C_{1-6}$, alkyl groups; and m1 and m2 may be the same or different, and each is an integer of 0 to 2 (wherein m1+m2 is an integer of 1 to 4).

The compound represented by Formula (F1b) is preferably a compound represented by Formula (F1b-1):

[Chem. 53]

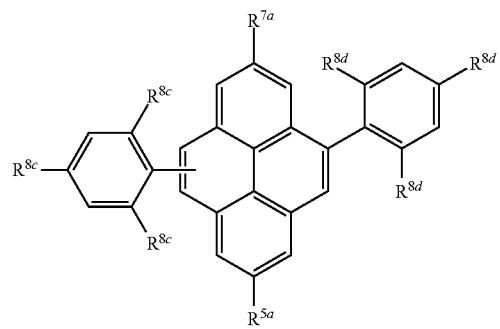

(F1b-1)

wherein $R^{5a}$ and $R^{7a}$ may be the same or different, and each represents $C_{1-20}$, particularly $C_{1-6}$, alkyl; and $R^{8c}$ and $R^{8d}$ are the same as the above; and a compound represented by Formula (F1b-2):

[Chem. 54]

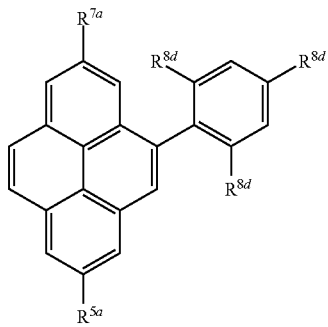

(F1b-2)

wherein $R^{5a}$, $R^{7a}$, and $R^{8d}$ are as defined above.

The compounds shown in the Examples below are particularly preferable.

Among the compounds produced by the reactions according to the first embodiment of the present invention, compounds represented by Formula (F2), which are obtained by using the compound of Formula (B) that satisfies requirement (3), are novel compounds that are not disclosed in any documents.

[Chem. 55]

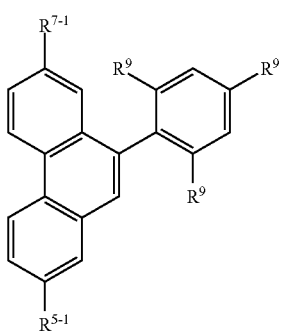

(F2)

wherein $R^{5-1}$ and $R^{7-1}$ may be the same or different, and each represents hydrogen or $C_{1-20}$, particularly $C_{1-6}$, alkyl, particularly 1 to 6 carbon atoms, $R^9$ may be the same or different, and each represents hydrogen, halogen, fluorine-containing or fluorine-free $C_{1-20}$, particularly $C_{1-6}$, alkyl, or a monocyclic or bicyclic aromatic group (wherein none or two of the three $R^9$ are hydrogen).

The compound of Formula (F2) is preferably, for example, a compound represented by Formula (F2-1):

[Chem. 56]

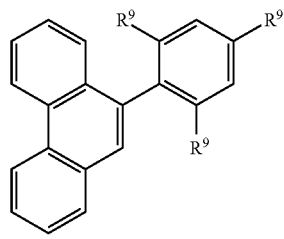

(F2-1)

wherein $R^9$ is as defined above.

The compounds shown in the Examples below are particularly preferable.

Among the compounds produced by the reactions according to the first embodiment of the present invention, compounds represented by Formula (F4), which are obtained by using the compound of Formula (B) that satisfies requirement (2), are novel compounds that are not disclosed in any documents.

[Chem. 57]

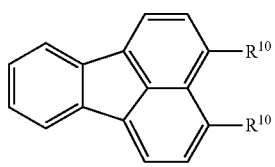

(F4)

wherein $R^{10}$ may be the same or different, and each represents a monocyclic or bicyclic aromatic ring optionally substituted with one to three substituents selected from the group consisting of halogen atoms and fluorine-containing or fluorine-free $C_{1-20}$, particularly $C_{1-6}$, alkyl groups, or hydrogen (wherein none or one of the two $R^{10}$ is hydrogen); and two $R^{10}$ may bond to each other to form a ring.

The compound of Formula (F4) is preferably, for example, a compound represented by Formula (F4-1):

[Chem. 58]

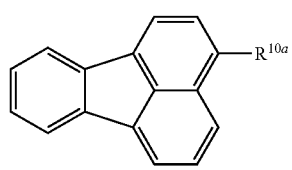

(F4-1)

wherein $R^{10a}$ is a monocyclic or bicyclic aromatic ring optionally substituted with 1 to 3 substituents selected from the group consisting of halogen atoms and fluorine-containing or fluorine-free $C_{1-20}$, particularly $C_{1-6}$, alkyl groups.

The compounds shown in the Examples are particularly preferable.

Among the compounds produced by the reactions according to the first embodiment of the present invention, compounds represented by Formula (F5), which are obtained by using the compound of Formula (B) that satisfies requirement (2), are also novel compounds that are not disclosed in any documents.

[Chem. 59]

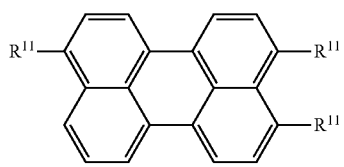

(F5)

wherein $R^{11}$ may be the same or different, and each represents a monocyclic or bicyclic aromatic group optionally substituted with one to three substituents selected from the group consisting of halogen atoms and fluorine-containing or fluorine-free $C_{1-20}$, particularly $C_{1-6}$, alkyl groups.

The compound represented by this formula (F5) is preferably, for example, a compound represented by Formula (F5-1):

[Chem. 60]

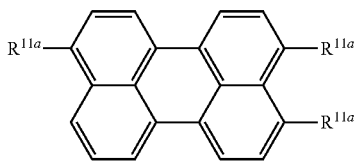

(F5)

wherein $R^{11a}$ may be the same, and each represents a monocyclic or bicyclic aromatic ring optionally substituted with 1 to 3 substituents selected from the group consisting of halogen atoms and fluorine-containing or fluorine-free $C_{1-20}$, preferably $C_{1-6}$, alkyl groups.

The compounds shown in the Examples below are particularly preferable.

2. Second Embodiment (Annulation Reaction) after C—H/C—B Coupling

In the production method according to the second embodiment of the present invention, an annulation reaction (Step (II)) is performed after performing a C—H/C—B coupling reaction or C—H/C—H coupling reaction (Step (I)).

[2-1]C—H/C—B Coupling Reaction or C—H/C—H Coupling Reaction (Step (I))

The reaction in Step (I) is the same as that in the first embodiment described above and that in the third embodiment explained later. In order to perform an annulation reaction in the subsequence step, i.e., Step (II), it is necessary to appropriately select the polycyclic aromatic compound (B), and boron compound (A) or substituted or unsubstituted aryl-containing compound (E), which are the starting materials. The components other than those mentioned above, and the reaction conditions may be the same as that in the first embodiment and that in the third embodiment.

Polycyclic Aromatic Compound (B)

In the second embodiment of the present invention, a compound having a phenanthrene skeleton is used as a starting material, because in such a compound, the C—H bonds can be easily regioselectively arylated, and the annulation reaction can be easily performed in subsequent Step (II). Such a starting material satisfies (3) or (4) in Formula (B) above. Specifically, a compound having a structure represented by Formula (B') below is used.

[Chem. 61]

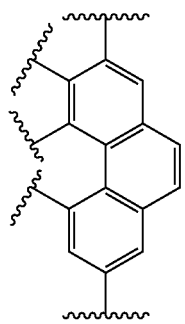

(B')

In this case, an arylated aromatic compound can be obtained by the reaction shown below:

[Chem. 62]

Palladium compound
o-Chloranil
Boron compound
→

(B')

(D')

In the present invention, a compound having a phenanthrene skeleton is a concept including such as pyrene represented by the formula below:

[Chem. 63]

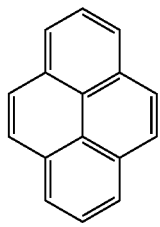

As a polycyclic aromatic compound (B), such as fluoranthene represented by the formula below:

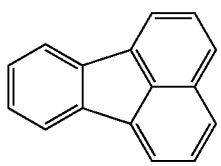

a compound having a structure represented by Formula (B''):

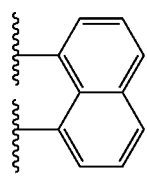
(B'')

may also be used.

In this case, by the reaction shown in the reaction scheme below:

[Chem. 66]

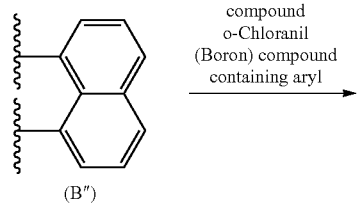

an arylated aromatic compound can be obtained.

Boron Compound (A)

In the second embodiment of the present invention, because the annulation reaction can be easily performed in subsequent Step (II), in a compound having a structure represented by Formula (B'), an aryl group having a biphenyl skeleton is used. Specifically, a compound having a structure represented by Formula (G):

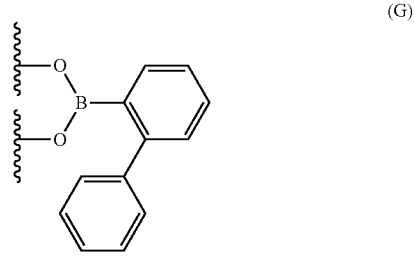

and preferably a compound having a structure represented by the formula below is used.

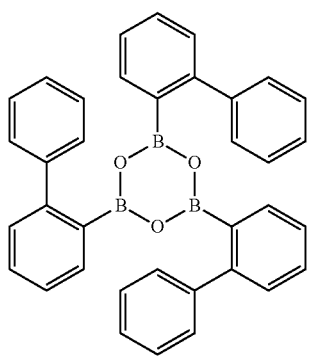

The compound is encompassed in cyclic organic boron compound (A2).

In a compound having a structure represented by Formula (B''), an aryl group having a naphthalene skeleton is used. Specifically, a compound having a structure represented by Formula (G'):

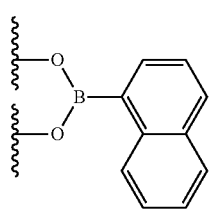

and preferably a compound having a structure represented by the formula below is used.

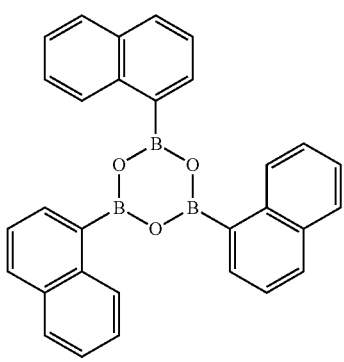

[Chem. 70]

The compound is encompassed in cyclic organic boron compound (A2).

Substituted or Unsubstituted Aryl-Containing Compound (E)

When the fluoranthene described above is used as the polycyclic aromatic compound (B), other than the compounds represented by Formula (G') described above, naphthalene or the like can be used (the compounds represented by Formula (G') may be collectively called a compound having a naphthalene skeleton). The compounds are encompassed in the substituted or unsubstituted aryl-containing compound (E) described later.

[2-2] Annulation Reaction (Step (II))

In Step (II), a known annulation reaction is performed. For example, when a polycyclic aromatic compound having a structure represented by Formula (B') and the boron compound containing an aryl group having a biphenyl skeleton described above are used, due to the reaction shown below:

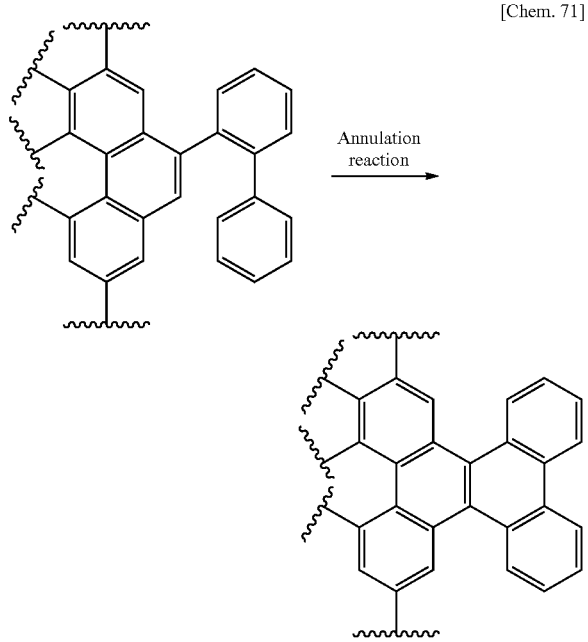

[Chem. 71]

the conjugated system can be expanded.

When a compound represented by Formula (B") is used as the polycyclic aromatic compound (B) and naphthalene is used as the substituted or unsubstituted aryl-containing compound (E), the conjugated system can be expanded by the reaction shown below:

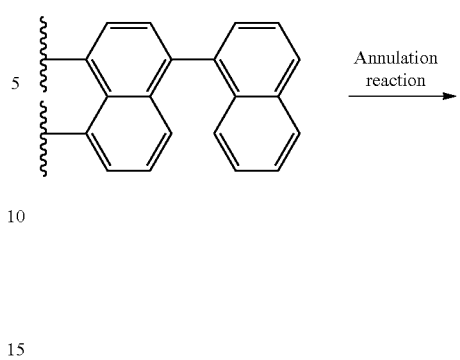

[Chem. 72]

The annulation reaction is not particularly limited. By combining with a known annulation reaction as described above, the conjugated system can be expanded.

Such an annulation reaction may be performed by a general oxidation reaction or a Scholl reaction. Moreover, the reaction is not limited to an oxidation reaction, and may be an anionic reaction. In this case, an oxidation reaction may be performed using antimony pentachloride, aluminum chloride, aluminum bromide, titanium tetrachloride, tin tetrachloride, zinc chloride, copper chloride, iron(III) chloride ($FeCl_3$), boron trifluoride, hydrogen fluoride, phosphoric acid, diphosphorus pentaoxide, polyphosphoric acid, potassium ferricyanide, manganese dioxide, hydrogen peroxide, persulfuric acid, iodine, selenium dioxide, and organic peroxide. Alternatively, an anionic reaction using potassium may be performed. In the present invention, a Scholl reaction using $FeCl_3$ or an anionic reaction using potassium is preferable.

The solvent used in this step may be a nonpolar solvent or polar solvent. Examples of the usable solvents include alkanes such as hexane, heptane, and octane; haloalkanes such as methylene chloride, chloroform, carbon tetrachloride, and ethylene chloride; benzenes such as benzene, toluene, xylene, mesitylene, and pentamethylbenzene; halobenzenes such as chlorobenzene, 1,2-dichloroethylene (1,2-DCE) and bromobenzene; ethers such as diethyl ether and anisole; methyl nitrate; dimethyl sulfoxide; and nitromethane. These solvents may be used singly, or in a combination of two or more.

The reaction temperature of the annulation reaction is generally selected from the range of from 0° C. to the boiling point of the solvent. The reaction pressure of the annulation reaction of the present invention is generally selected within an atmospheric pressure. The reaction time of the annulation reaction is generally selected from the range of 1 to 24 hours.

The reaction atmosphere is not particularly limited, and is preferably an inert gas atmosphere such as argon gas atmosphere or nitrogen gas atmosphere. An air atmosphere may also be adopted.

When a compound having a pyrene skeleton represented by Formula (B'-1) is used as a starting material,

[Chem. 73]

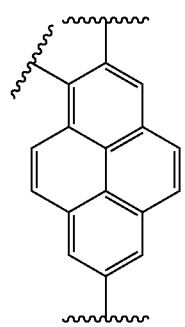
(B'-1)

two C—H bonds can be selectively substituted with an aryl group in Step (I). Therefore, compared to the case where one C—H bond is selectively substituted with an aryl group, the conjugated system can be further expanded. In this case, it is possible to eventually obtain a compound having the structure represented by Formula (C-1) below:

[Chem. 74]

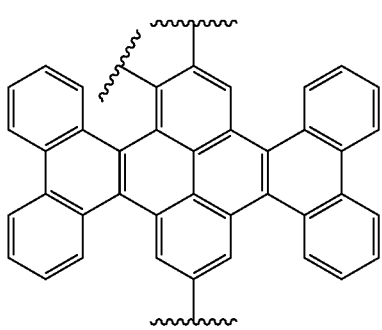
(C-1)

Among the compounds produced in the second embodiment of the present invention, a compound represented by the formula below:

[Chem. 75]

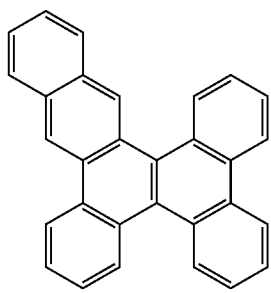

and a compound represented by Formula (F3):

[Chem. 76]

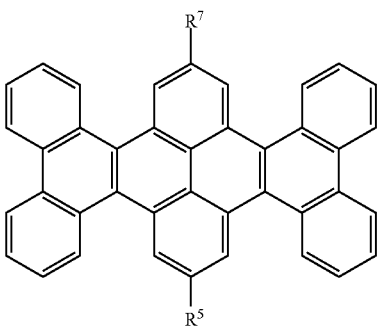
(F3)

wherein $R^5$ and $R^7$ are as defined above, are novel compounds that are not disclosed in any documents.

Among these, as a compound represented by Formula (F3), a compound represented by Formula (F3-1) is preferable:

[Chem. 77]

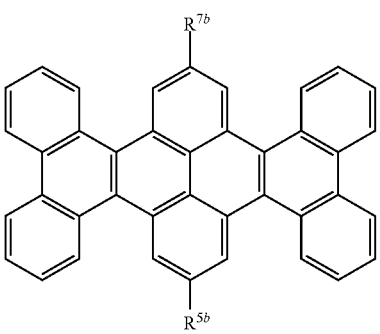
(F3-1)

wherein $R^{5b}$ and $R^{7b}$ may be the same or different, and each represents a $C_{1-6}$ alkyl.

The compounds described in the Examples later are particularly preferable.

Among the compounds produced by the method of the second embodiment of the present invention, a compound represented by the formula below:

[Chem. 78]

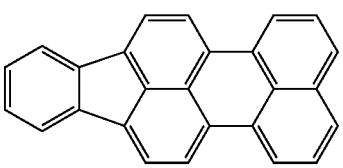

is a novel compound that is not disclosed in any documents.

3. Third Embodiment C—H/C—H Coupling

The method for producing an aromatic compound according to the third embodiment of the present invention is such that a polycyclic aromatic compound and a substituted or unsubstituted aryl-containing compound are reacted in the presence of a palladium compound and o-chloranil to obtain a polycyclic aromatic compound substituted with at least one substituted or unsubstituted aryl group.

[3-1] Polycyclic Aromatic Compound (B)

As the polycyclic aromatic compound (B), the same compounds as those used in the first embodiment can be used. Specific examples are described below.

The polycyclic aromatic compound used as a substrate in the present invention is not particularly limited, as long as it has a structure in which two or more rings are fused thereto. Specifically, a polycyclic aromatic compound represented by Formula (B) is preferable:

[Chem. 79]

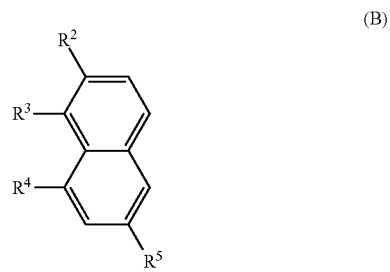

(B)

wherein $R^2$ to $R^5$ may be the same or different, and each represents hydrogen or $C_{1-20}$, in particular $C_{1-6}$ alkyl, and satisfies any one of requirements described in (1) to (4) below.
(1) $R^2$ to $R^5$ are each hydrogen.
(2) $R^2$ and $R^5$ are each hydrogen; $R^3$ and $R^4$ bond to each other to form a 5- or 6-membered unsaturated ring; and the unsaturated ring may further have a monocyclic or fused aromatic ring fused thereto.
(3) $R^2$ and $R^3$ bond to each other to form a substituted or unsubstituted aromatic ring; $R^4$ is hydrogen; and $R^5$ is hydrogen or $C_{1-20}$, in particular $C_{1-6}$ alkyl.
(4) $R^2$ and $R^3$ bond to each other to form a substituted or unsubstituted aromatic ring; $R^3$ and $R^4$ bond to each other to form a substituted or unsubstituted aromatic ring; and $R^5$ is hydrogen or $C_{1-20}$, in particular $C_{1-6}$ alkyl.

More specifically, the polycyclic aromatic compound used in the present invention preferably has at least a naphthalene skeleton.

Polycyclic Aromatic Compound (B1)

Among various polycyclic aromatic compounds (B), polycyclic aromatic compound (B1) satisfies requirement (1), and is naphthalene. In this case, an arylated naphthalene can be obtained by the reaction scheme shown below:

[Chem. 80]

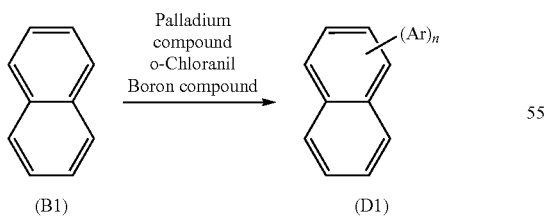

wherein Ar is a substituted or unsubstituted $C_{6-50}$ aryl; n is an integer of 1 to 4; and Ar may bond to either of the two benzene rings.

In aromatic compound (D1), Ar is substituted or unsubstituted $C_{6-50}$ aryl derived from the boron compound described above. Specific examples of the aryl groups include phenyl, naphthyl, anthranil, phenanthryl, and biphenyl groups. Among these, phenyl is preferable. Examples of the substituents that may be contained in the aryl include halogen atoms (such as F, Cl, and Br); $C_{1-20}$, in particular $C_{1-6}$ alkyl groups (such as methyl, ethyl, and perfluoromethyl) optionally having halogen; and $C_{1-20}$, in particular $C_{1-6}$ alkoxy groups (such as methoxy) optionally having halogen. The number of substituents is not particularly limited, and is preferably 1 to 3.

Specific examples of such aryl groups (Ar) are shown below.

[Chem. 81]

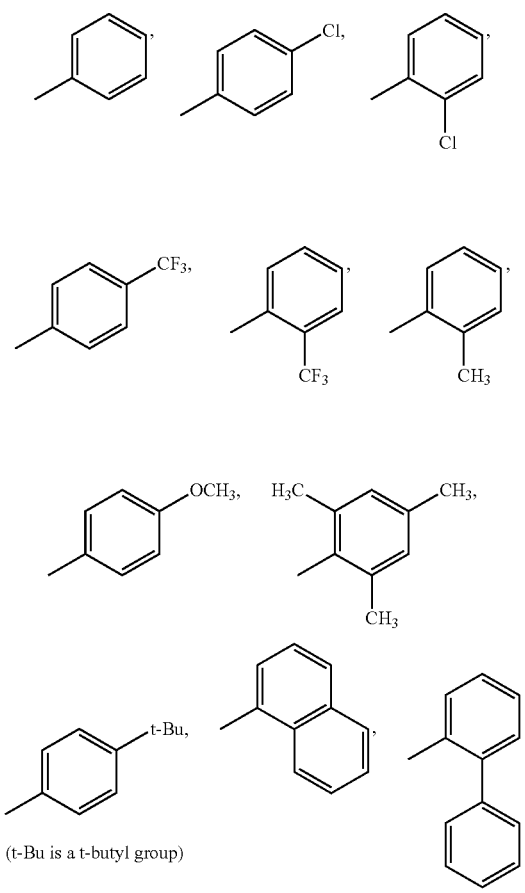

(t-Bu is a t-butyl group)

Polycyclic Aromatic Compound (B2)

Among polycyclic aromatic compounds (B), polycyclic aromatic compound (B2) satisfies requirement (2). Specific examples thereof include a compound represented by Formula (B2):

[Chem. 82]

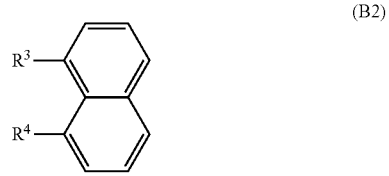

(B2)

wherein $R^3$ and $R^4$ are as defined in (2) of Formula (B).

In this case, an arylated aromatic compound can be obtained by the reaction shown below:

[Chem. 83]

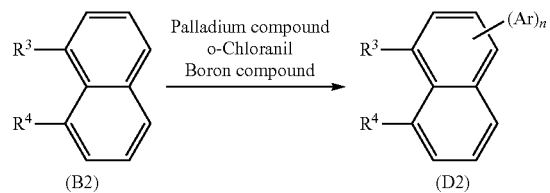

wherein $R^3$ and $R^4$ are as defined in (2) of Formula (B) above; Ar and n are as defined above; and Ar may bond to any of the cyclic structures.

$R^3$ and $R^4$ bond to each other to form a 5- or 6-membered unsaturated ring. Considering the fact that the aromatic compound obtained by the production method of the present invention is used as a precursor of graphene, a 6-member unsaturated ring (e.g., benzene ring) is preferable.

The unsaturated ring formed by bonding $R^3$ and $R^4$ may further have a monocyclic or fused aromatic ring fused thereto. The aromatic ring preferably has 6 carbon atoms. A specific example of the aromatic ring is a benzene ring. Specific examples of the fused aromatic rings include naphthalene ring, phenanthrene ring, and anthracene ring.

Specific examples of such polycyclic aromatic compounds (B2) include perylene represented by the formula below:

[Chem. 84]

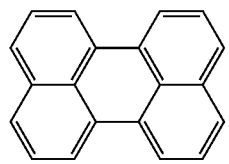

and fluoranthene represented by the formula below:

[Chem. 85]

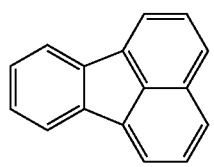

When perylene is used, it is possible to obtain an aromatic compound as represented by Formula (D2a) in which four hydrogen atoms are regioselectively substituted with an aryl group for each:

[Chem. 86]

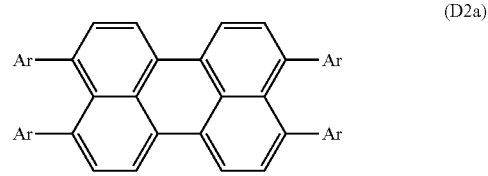

wherein four Ar may be the same or different, and each is as defined above.

Polycyclic Aromatic Compound (B3)

Among polycyclic aromatic compounds (B), polycyclic aromatic compound (B3) satisfies requirement (3). Specific examples thereof include a compound represented by Formula (B3):

[Chem. 87]

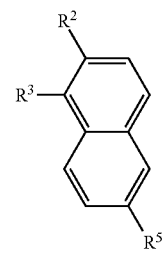

wherein $R^2$, $R^3$, and $R^5$ are as defined in (3) of Formula (B).

In this case, an arylated aromatic compound can be obtained by the reaction shown below:

[Chem. 88]

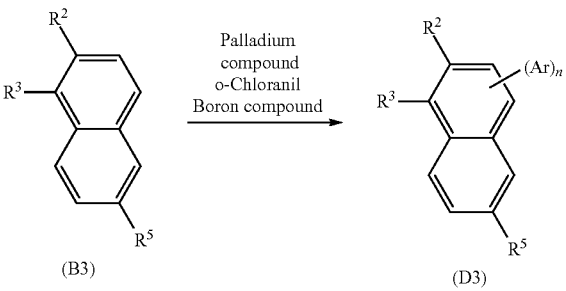

wherein $R^2$, $R^3$, and $R^5$ are as defined in (3) of Formula (B); Ar and n are as defined above; and Ar may bond to any of the cyclic structures.

$R^2$ and $R^3$ bond to each other to form a substituted or unsubstituted aromatic ring. The aromatic ring preferably has 6 to 12 carbon atoms. In this case, examples of the fused aromatic ring include benzene ring and naphthalene ring.

Examples of the substituents that may be contained in the aromatic ring include halogen atoms (such as F, Cl, and Br); and $C_{1-20}$, in particular $C_{1-6}$ alkyl optionally having halogen. The number of substituents is not particularly limited, and is preferably 1 to 6.

$R^5$ is a hydrogen atom or $C_{1-20}$, in particular $C_{1-6}$ alkyl. Specific examples thereof include hydrogen atom, methyl, ethyl, isopropyl, n-propyl, t-butyl, and n-hexyl groups.

Specific examples of such polycyclic aromatic compounds (B3) include compounds represented by the formulas below:

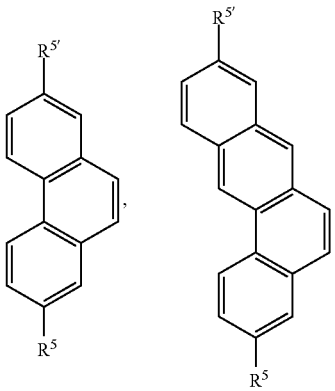

[Chem. 89]

wherein $R^5$ is as defined above; $R^{5'}$ is defined in the same manner as $R^5$, and $R^5$ and $R^{5'}$ may be the same or different.

Polycyclic Aromatic Compound (B4)

Among polycyclic aromatic compounds (B), polycyclic aromatic compound (B4) satisfies requirement (4). Specific examples thereof include a compound represented by Formula (B4):

[Chem. 90]

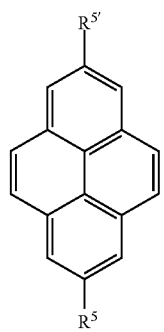

(B4)

wherein $R^2$ to $R^5$ are as defined in (4) of Formula (B).

In this case, an arylated aromatic compound can be obtained by the reaction shown below:

[Chem. 91]

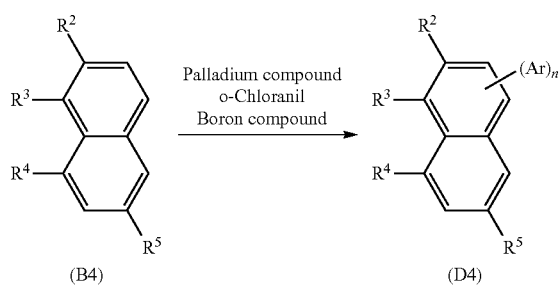

wherein $R^2$ to $R^5$ are as defined in (4) of Formula (B); Ar and n are as defined above; and Ar may bond to any of the cyclic structures.

$R^2$ and $R^3$ bond to each other to form a substituted or unsubstituted aromatic ring. The aromatic ring preferably has 6 to 12 carbon atoms. In this case, examples of the aromatic rings to be fused include benzene ring and naphthalene ring.

Examples of the substituents that may be contained in the aromatic ring include halogen atoms (such as F, Cl, and Br); and $C_{1-20}$, in particular $C_{1-6}$ alkyl optionally having halogen. The number of substituents is not particularly limited, and is preferably 1 to 6.

$R^3$ and $R^4$ bond to each other to form a substituted or unsubstituted aromatic ring. The aromatic ring preferably has 6 carbon atoms. In this case, one example of the aromatic ring is a benzene ring.

Examples of the substituents that may be contained in the aromatic ring include halogen atoms (such as F, Cl, and Br); and $C_{1-20}$, in particular $C_{1-6}$ alkyl optionally having halogen. The number of substituents is not particularly limited, and is preferably 1 to 6.

$R^5$ is a hydrogen atom or a $C_{1-20}$, in particular $C_{1-6}$ alkyl. Specific examples thereof include hydrogen atom, methyl, ethyl, isopropyl, n-propyl, t-butyl, and n-hexyl groups.

Specific examples of such polycyclic aromatic compounds (B4) include a compound represented by the formula below:

[Chem. 92]

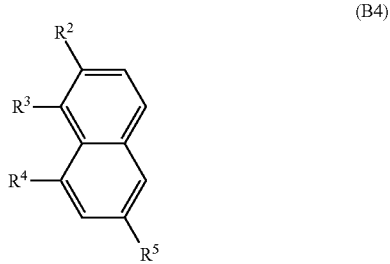

wherein $R^5$ and $R^{5'}$ are as defined above.

[3-2] Palladium Compound

As the palladium compound, the same compounds as those used in the first embodiment can be used. Specific examples thereof are described below.

Here, the reaction is generally performed in the presence of a palladium compound. Examples of the palladium compound include known palladium compounds used as a catalyst for synthesizing organic compounds (including polymers). The palladium compounds may be either a compound containing a zerovalent palladium, or a compound containing a divalent palladium. When a compound containing a zerovalent palladium is used, the zerovalent palladium is oxidized in the system to form a divalent palladium. Specific examples of the usable palladium compounds include $Pd(OAc)_2$ (Ac is acetyl), $PdCl_2$, $PdBr_2$, $PdI_2$, and $Pd(OTf)_2$ (Tf is trifluoromethylsulfonyl). $Pd(OAc)_2$ is preferably used in the present invention.

The amount of palladium compound is, in terms of the yield, typically 0.01 to 0.5 mol and preferably 0.025 to 0.2 mol, per mol of polycyclic aromatic compound (B), which is the starting material.

Here, a ligand that is capable of coordinating with the palladium atom, which is the central element of the palladium compound, may be combined, if necessary. However, ligands lose their coordinative ability when oxidized due to the oxidizing power of the o-chloranil described later; therefore, when a ligand is used, it is desirable to use a ligand that is strong against oxidation. Examples of such ligands include phosphate-based ligands such as triphenyl phosphite, triisopropyl phosphite, tris(2,2,2-trifluoroethyl)phosphite, and tris(1,1,1,3,3,3-hexafluoroisopropyl)phosphite.

When a ligand is used, the amount thereof is, in terms of the yield, typically 0.01 to 0.5 mol, preferably 0.025 to 0.2 mol, per mol of polycyclic aromatic compound (B), which is the starting material.

[3-3] o-Chloranil

Here, o-chloranil is used as an oxidant in the same manner as in the first embodiment. The o-chloranil is represented by the formula below:

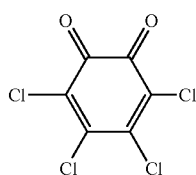

[Chem. 93]

By the use of o-chloranil as an oxidant, the yield can be improved and the production of by-products such as biphenyl can be suppressed.

The yield can also be improved when 3,5-di-tert-butyl-1,2-benzoquinone represented by the following formula is used as an oxidant.

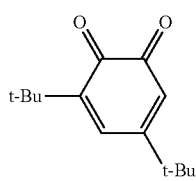

[Chem. 94]

(t-Bu is a t-butyl group).

However, in this case, a large amount of biphenyl, which is a byproduct, is produced. Furthermore, the yield is also lower compared to the case where o-chloranil is used.

Even if p-chloranil having the structure shown below

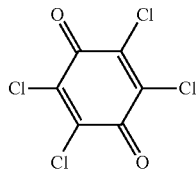

[Chem. 95]

which is similar to that of o-chloranil, is used as an oxidant, the yield cannot be improved.

For the reasons described above, the use of o-chloranil as an oxidant makes it possible, for the first time, to arylate the C—H bonds of a polycyclic aromatic compound in a simple manner.

The amount of o-chloranil is, in terms of the yield, typically 1 to 5 mol and preferably 1 to 2 mol, per mol of polycyclic aromatic compound (B).

[3-4] Substituted or Unsubstituted Aryl-Containing Compound

The aryl contained in the substituted or unsubstituted aryl-containing compound used in the present invention is the same as the Ar described above, and the specific examples thereof are also the same. The substituents that may be contained in the aryl are the same as those described above that the Ar may contain. Specific examples thereof include the following:

The aryl has 6 to 50 carbon atoms, and may contain one or more substituents. Specific examples of the aryl groups include phenyl, naphthyl, anthranil, phenanthrenyl, and biphenyl groups. Among these, phenyl is preferable. Examples of the substituents that may be contained in the aryl include halogen atoms (such as F, Cl, and Br), $C_{1-20}$, in particular $C_{1-6}$ alkyl groups (such as methyl, ethyl, and perfluoromethyl) optionally having halogen; and $C_{1-20}$, in particular $C_{1-6}$ alkoxy groups (such as methoxy) optionally having halogen. The number of substituents is not particularly limited, and is preferably 1 to 3.

Specific examples of such aryl groups include the following:

[Chem. 96]

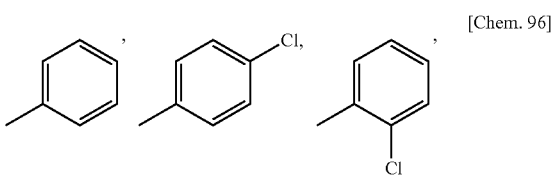

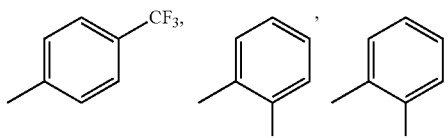

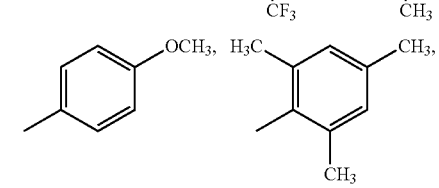

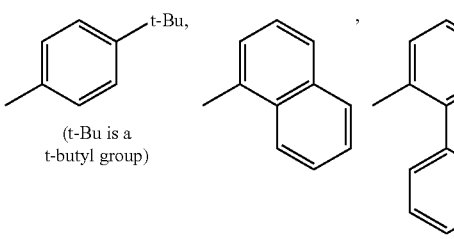

(t-Bu is a t-butyl group)

One example of a preferable compound containing a substituted or unsubstituted aryl is a compound represented by Formula (E):

[Chem. 97]

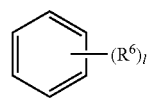

(E)

wherein the l number of $R^6$ may be the same or different, and each represents halogen atom, $C_{1-20}$ alkyl, $C_{1-20}$ alkoxy, $C_{3-50}$ cycloalkyl, or $C_{6-50}$ aryl; and l is an integer of 0 to 4; or a compound represented by Formula (E'):

[Chem. 98]

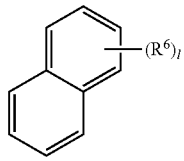

(E')

wherein $R^6$ and l are as defined above; and each $R^6$ may bond to a benzene ring.

In particular, a compound represented by Formula (E1) is preferable:

[Chem. 99]

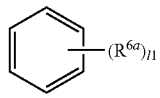

(E1)

wherein the $l_1$ number of $R^{6a}$ may be the same or different, and each represents a $C_{1-6}$ alkyl or $C_{1-6}$ alkoxy; and $l_1$ is an integer of 2 to 4.

Specific examples of such compounds include the following:

[Chem. 100]

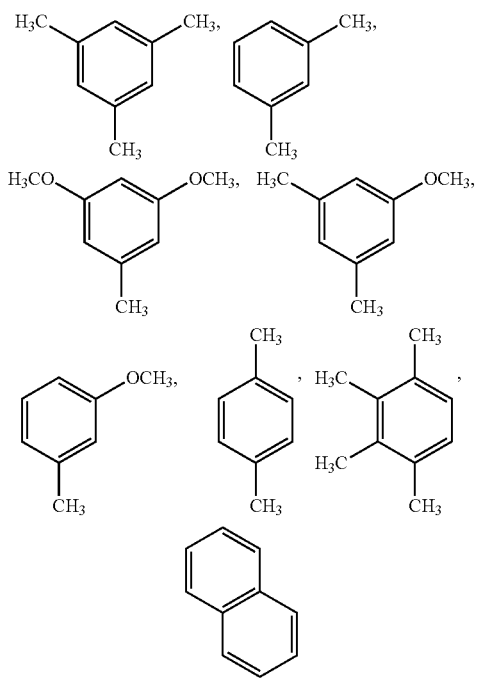

Among these, the following compounds are preferable in terms of the yield.

[Chem. 101]

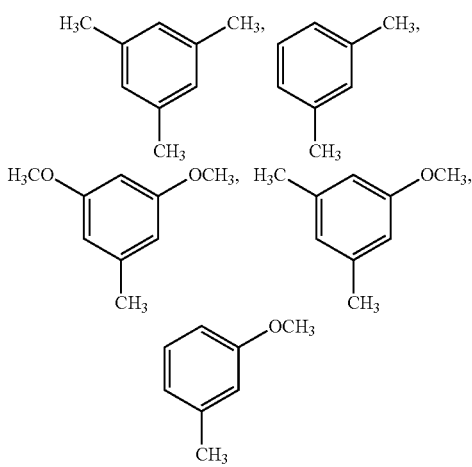

[Chem. 102]

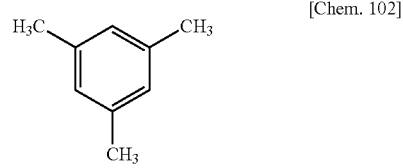

When a compound having a structure represented by Formula (B"), such as fluoranthene, perylene, or the like, is used as a polycyclic aromatic compound, and naphthalene is used as a substituted or unsubstituted aryl-containing compound, the conjugated system in the second embodiment described above can be expanded. In this respect, naphthalene is preferable as the substituted or unsubstituted aryl-containing compound.

In the third embodiment of the present invention, among the substituted or unsubstituted aryl-containing compounds, since a compound represented by Formula (E) can be used as a solvent, it is preferable to use an excessive amount of a compound represented by Formula (E). In contrast, a compound represented by Formula (E') cannot be used as a solvent; however, in view of the reactivity, it is also preferable to use an excessive amount of a compound represented by Formula (E').

[3-5] Silver Compound

In the third embodiment of the present invention, a silver compound may be co-present in the reaction between the polycyclic aromatic compound (B) and the substituted or unsubstituted aryl-containing compound (E). This can accelerate the reaction.

AgOTf (Tf is trifluoromethylsulfonyl) is preferable as such a silver compound.

In the third embodiment of the present invention, the amount of silver compound is, in terms of the yield, typically 0.01 to 1 mol and preferably 0.025 to 0.4 mol, per mol of the polycyclic aromatic compound (B), which is the starting material.

[3-6] Solvent

When a compound represented by Formula (E) is used as the substituted or unsubstituted aryl-containing compound (E), since the compound itself can be used as a substrate-solvent, the use of a solvent is not particularly necessary. When a compound represented by Formula (E') is used as the compound (E), it is preferable that a solvent is used.

Examples of the solvents include aliphatic hydrocarbons such as hexane, cyclohexane and heptane; aromatic hydrocarbons such as toluene, xylene, benzene, chlorobenzene, o-dichlorobenzene, m-dichlorobenzene and p-dichlorobenzene; esters such as methyl acetate, ethyl acetate and butyl acetate; cyclic ethers such as diethyl ether, tetrahydrofuran, dioxane, dimethoxyethane and diisopropyl ether; halogenated hydrocarbons such as 1,2-dichloroethane (1,2-DCE), methyl chloride, chloroform, dichloromethane, dichloroethane and dibromoethane; ketones such as acetone and methyl ethyl ketone; amides such as dimethylformamide and dimethylacetamide; nitriles such as acetonitrile; alcohols such as methanol, ethanol and isopropyl alcohol; and dimethyl sulfoxide. These solvents may be used singly, or in a combination of two or more. Among these, in the present invention, 1,2-dichloroethane (1,2-DCE), chlorobenzene, o-dichlorobenzene, m-dichlorobenzene, p-dichlorobenzene, dimethoxyethane, and the like, are preferable.

[3-7] Reaction Conditions

The reaction temperature in the third embodiment of the present invention is generally selected from the range of room temperature or higher, and not higher than the boiling point of the aryl-containing compound (E) that is used as the substrate-solvent. The reaction pressure in the third embodiment of the present invention is generally selected from the atmospheric pressure. The reaction time in the third embodiment of the present invention is generally selected from the range of 1 to 24 hours.

The reaction atmosphere is not particularly limited, and is preferably an inert gas atmosphere selected from an argon gas atmosphere, nitrogen gas atmosphere, or the like.

By setting the reaction conditions as described above, at least one hydrogen atom bonded to $sp^2$ hybridized carbon atoms of the polycyclic aromatic compound (B), which is the starting material, will be regioselectively replaced by an aryl group derived from an aryl-containing compound (E).

The aromatic compound eventually obtained is the same as that obtained in the first embodiment. More specifically, a compound represented by Formula (D) can be obtained:

[Chem. 103]

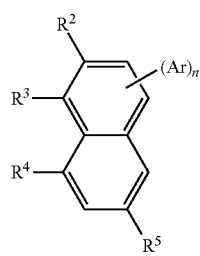

(D)

wherein $R^2$ to $R^5$ may be the same or different, and each represents hydrogen or $C_{1-20}$, in particular $C_{1-6}$ alkyl, and satisfies any one of requirements described in (1) to (4) below.
(1) $R^2$ to $R^5$ are each hydrogen.
(2) $R^2$ and $R^5$ are each hydrogen; $R^3$ and $R^4$ bond to each other to form a 5- or 6-membered unsaturated ring; and the unsaturated ring may further have a monocyclic or fused aromatic ring fused thereto.
(3) $R^2$ and $R^3$ bond to each other to form a substituted or unsubstituted aromatic ring; $R^4$ is hydrogen; and $R^5$ is hydrogen or $C_{1-20}$, in particular $C_{1-6}$ alkyl.
(4) $R^2$ and $R^3$ bond to each other to form a substituted or unsubstituted aromatic ring; $R^3$ and $R^4$ bond to each other to form a substituted or unsubstituted aromatic ring; and $R^5$ is hydrogen or $C_{1-20}$, in particular $C_{1-6}$ alkyl.

Among these, compounds represented by Formulas (F1a), (F1b), (F2), (F4), and (F5) are novel compounds that are not disclosed in any documents.

EXAMPLES

The present invention is explained in detail below with reference to the Examples; however, the present invention is not limited thereto or thereby.

All of the materials containing a dry solvent were used as purchased, i.e., without being purified, unless otherwise specified. All of the reactions were performed in flame-dried glassware in an argon atmosphere unless otherwise specified.

In the analysis, thin-layer chromatography (TLC) was performed using an E. Merck 60 $F_{254}$ thin-layer plate (0.25 mm). In preparative thin-layer chromatography (PTLC), a Wakogel® B5-F silica coated plate (0.75 mm) was produced and used. Gas chromatography (GC) analysis was performed using Shimadzu GC-2010 equipped with an HP-5 column (30 m×0.25 mm, Hewlett-Packard). In chromatography, UV lamps (254 nm and 365 nm) were used, and in high-resolution mass spectrometry (HRMS), JMS-T100TD (DART) was used. The melting point was measured using an MPA 100 OptiMelt melting point apparatus. The nuclear magnetic resonance (NMR) spectrum was recorded using an ECS-400 ($^1$H 400 MHz, $^{13}$C 100 MHz) and ECS-600 ($^1$H 600 MHz, $^{13}$C 150 MHz) produced by JEOL Ltd. The chemical shift of $^1$H NMR was expressed in ppm relative to tetramethylsilane (δ 0.0 ppm). The chemical shift of $^{13}$C NMR was expressed in ppm relative to $CDCl_3$ (δ 77.0 ppm).

Examples 1 to 6

In Examples 1 to 6, phenylated pyrene was obtained by the reaction of the formula below.

[Chem. 104]

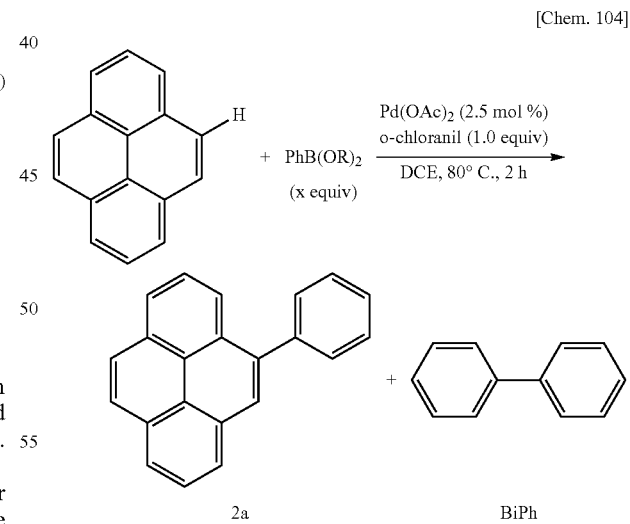

The details are described below.

Example 1

A $Pd(OAc)_2$ solution (1.1 mg, 5.0 µmol, 2.5 mol %), o-chloranil (49 mg, 0.20 mol, 1 equivalent), pyrene (40 mg, 0.20 mmol, 1 equivalent) represented by the formula below:

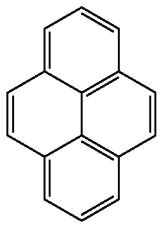

and phenylboronic acid (0.40 mmol, 2 equivalents) represented by the formula below:

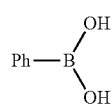

(Ph indicates a phenyl group.)

were introduced into 1,2-dichloroethane (1,2-DCE, 2.0 mL), and the mixture was stirred for 2 hours at 80° C. The GC yield was measured using n-dodecane as an internal standard.

Example 2

Example 2 was prepared in the same manner as Example 1, except that a compound represented by the formula below:

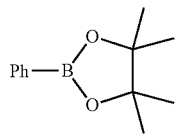

(Ph indicates a phenyl group.)

was used as a boron compound.

Example 3

Example 3 was prepared in the same manner as Example 1, except that a compound represented by the formula below:

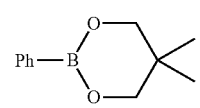

(Ph indicates a phenyl group.)

was used as a boron compound.

Example 4

Example 4 was prepared in the same manner as Example 1, except that a compound represented by the formula below:

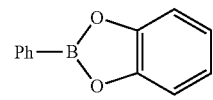 [SMILES: c1ccc(B2Oc3ccccc3O2)cc1]

(Ph indicates a phenyl group.)

was used as a boron compound.

Example 5

Example 5 was prepared in the same manner as Example 1, except that a compound (0.13 mol, 0.67 equivalents) represented by the formula below:

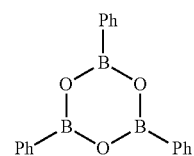 [SMILES: c1ccc(B2OB(c3ccccc3)OB(c3ccccc3)O2)cc1]

(Ph indicates a phenyl group.)

was used as a boron compound.

Example 6

Example 6 was prepared in the same manner as Example 1, except that a compound represented by the formula below:

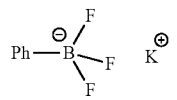

(Ph indicates a phenyl group.)

was used as a boron compound.

Table 1 shows the GC yields of 4-phenyl pyrene (2a) and biphenyl (BiPh), which were respectively the target product and the by-product of Examples 1 to 6.

TABLE 1

| Example | Boron compound | Amount of boron compound used (equivalent) | GC yield (%) 2a | BiPh |
|---|---|---|---|---|
| 1 | Ph—B(OH)$_2$ | 2.0 | 35 | 29 |
| 2 | Ph—Bpin | 2.0 | 4 | nd |

TABLE 1-continued

| Example | Boron compound | Amount of boron compound used (equivalent) | GC yield (%) 2a | GC yield (%) BiPh |
|---|---|---|---|---|
| 3 | Ph—B(OCH₂C(CH₃)₂CH₂O) | 2.0 | 8 | nd |
| 4 | Ph—B(O-catechol) | 2.0 | 4 | nd |
| 5 | (PhBO)₃ triphenylboroxine | 0.67 | 50 | 3 |
| 6 | Ph—BF₃⁻ K⁺ | 2.0 | 21 | 1 |

Examples 7 to 11

In Example 7 to 11, phenylated pyrene was obtained by the reaction of the formula below.

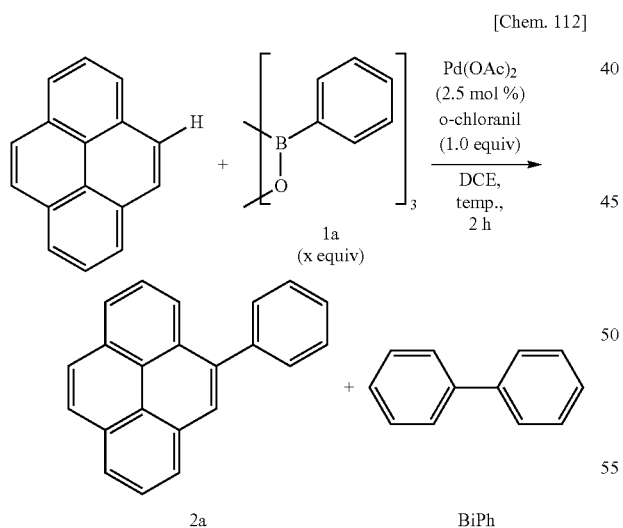

[Chem. 112]

The details are described below.

Example 7

A Pd(OAc)₂ solution (1.1 mg, 5.0 μmol, 2.5 mol %), o-chloranil (49 mg, 0.20 mol, 1 equivalent), pyrene (40 mg, 0.20 mmol, 1 equivalent) represented by the formula below:

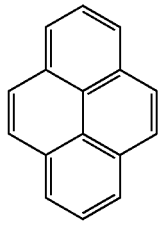

[Chem. 113]

and a boron compound (0.067 mmol, 0.33 equivalents) represented by the formula below:

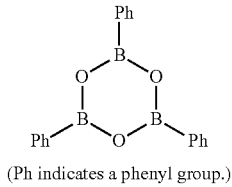

[Chem. 114]

(Ph indicates a phenyl group.)

were introduced into 1,2-dichloroethane (1,2-DCE, 2.0 mL), and the mixture was stirred for 2 hours at 80° C. The GC yield was measured using n-dodecane as an internal standard.

Example 8

Example 8 was prepared in the same manner as Example 7, except that the amount of the boron compound used was changed to 0.13 mmol (0.67 equivalents).

Example 9

Example 9 was prepared in the same manner as Example 7, except that the amount of the boron compound used was changed to 0.2 mmol (1 equivalent).

Example 10

Example 10 was prepared in the same manner as Example 7, except that the amount of the boron compound used was changed to 0.13 mmol (0.67 equivalents), and the stirring temperature was set at 50° C.

Example 11

Example 11 was prepared in the same manner as Example 7, except that the amount of the boron compound was changed to 0.13 mmol (0.67 equivalents), and the stirring temperature was set at room temperature (rt).

Table 2 shows the GC yields of phenylated pyrene (2a) and biphenyl (BiPh), which were respectively the target product and the by-product of Examples 7 to 11.

TABLE 2

| Example | Amount of boron compound used (equivalent) | Stirring temperature (° C.) | GC yield (%) 2a | GC yield (%) BiPh |
|---|---|---|---|---|
| 7 | 0.33 | 80 | 36 | 2 |
| 8 | 0.67 | 80 | 50 | 3 |
| 9 | 1.00 | 80 | 54 | 11 |

TABLE 2-continued

| Example | Amount of boron compound used (equivalent) | Stirring temperature (° C.) | GC yield (%) 2a | BiPh |
|---|---|---|---|---|
| 10 | 0.67 | 50 | 51 | 8 |
| 11 | 0.67 | rt | 41 | 11 |

Example 12 and Comparative Examples 1 to 7

In Example 12 and Comparative Examples 1 to 7, phenylated pyrene was obtained by the reaction of the formula below.

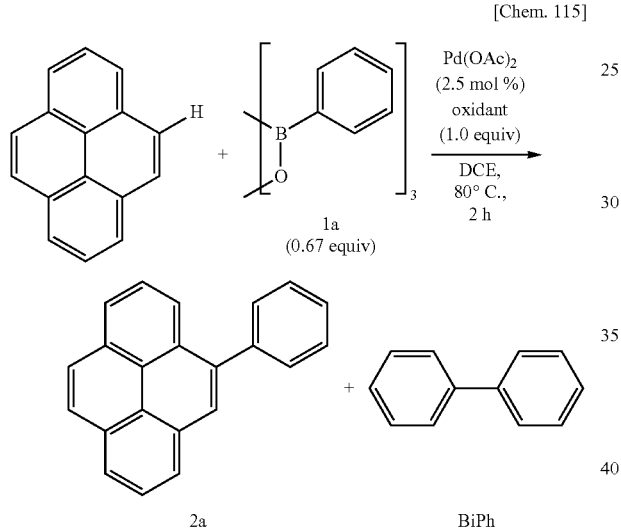

The details are described below.

Example 12

A Pd(OAc)$_2$ solution (1.1 mg, 5.0 μmol, 2.5 mol %), o-chloranil (49 mg, 0.20 mmol, 1 equivalent), pyrene (40 mg, 0.20 mmol, 1 equivalent) represented by the formula below:

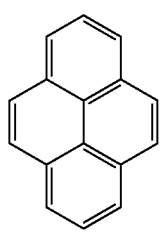

and a boron compound (0.13 mmol, 0.67 equivalents) represented by the formula below:

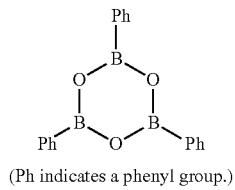

(Ph indicates a phenyl group.)

were introduced into 1,2-dichloroethane (1,2-DCE, 2.0 mL), and the mixture was stirred for 2 hours at 80° C. The GC yield was measured using n-dodecane as an internal standard.

Comparative Example 1

Comparative Example 1 was prepared in the same manner as Example 12, except that 44.0 mg (0.20 mol, 1 equivalent) of 3,5-di-tert-butyl-1,2-benzoquinone (o-DBQ) represented by the formula below:

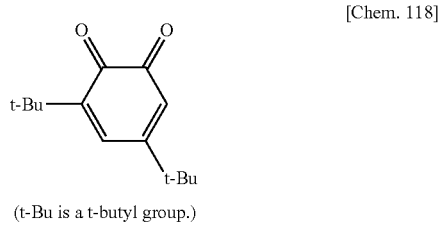 [SMILES: CC(C)(C)C1=CC(=O)C(=O)C(C(C)(C)C)=C1]

(t-Bu is a t-butyl group.)

was used in place of o-chloranil.

Comparative Example 2

Comparative Example 2 was prepared in the same manner as Example 12, except that 41.6 mg (0.20 mmol, 1 equivalent) of 9,10-phenanthrenequinone (9,10-PQ) represented by the formula below:

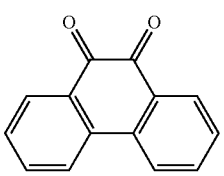 [SMILES: O=C1C(=O)c2ccccc2-c2ccccc21]

was used in place of o-chloranil.

Comparative Example 3

Comparative Example 3 was prepared in the same manner as Example 12, except that 49.2 mg (0.20 mmol, 1 equivalent) of p-chloranil represented by the formula below:

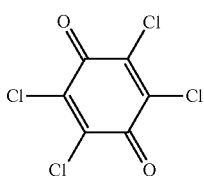 [SMILES: O=C1C(Cl)=C(Cl)C(=O)C(Cl)=C1Cl]

was used in place of o-chloranil.

Comparative Example 4

Comparative Example 4 was prepared in the same manner as Example 12, except that 45.4 mg (0.20 mmol, 1 equivalent) of 2,3-dichloro-5,6-dicyano-p-benzoquinone represented by the formula below:

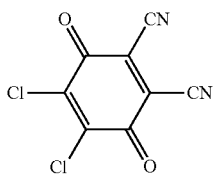 [SMILES: N#CC1=C(C#N)C(=O)C(Cl)=C(Cl)C1=O]

was used in place of o-chloranil.

Comparative Example 5

Comparative Example 5 was prepared in the same manner as Example 12, except that 21.6 mg (0.20 mmol, 1 equivalent) of 1,4-benzoquinone represented by the formula below:

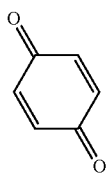

was used in place of o-chloranil.

Comparative Example 6

Comparative Example 6 was prepared in the same manner as Example 12, except that 26.9 mg (0.20 mmol, 1 equivalent) of $CuCl_2$ was used in place of o-chloranil.

Comparative Example 7

Comparative Example 7 was prepared in the same manner as Example 12, except that 54.0 mg (0.20 mol, 1 equivalent) of $K_2S_2O_8$ was used in place of o-chloranil.

Table 3 shows the GC yields of 4-phenylated pyrene (2a) and biphenyl (BiPh), which were respectively the target product and the by-product of Example 12 and Comparative Examples 1 to 7.

TABLE 3

| Example | Oxidizing agent | GC yield (%) 2a | GC yield (%) BiPh |
|---|---|---|---|
| Example 12 | o-chloranil (tetrachloro-o-benzoquinone) | 50 | 3 |
| Comp. Exam. 1 | 3,5-di-t-Bu-o-benzoquinone | 28 | 29 |
| Comp. Exam. 2 | phenanthrenequinone | <1 | 11 |
| Comp. Exam. 3 | tetrachloro-p-benzoquinone | 1 | 1 |
| Comp. Exam. 4 | DDQ | 3 | 1 |
| Comp. Exam. 5 | 1,4-benzoquinone | nd | <1 |
| Comp. Exam. 6 | $CuCl_2$ | 1 | 1 |
| Comp. Exam. 7 | $K_2S_2O_8$ | nd | 3 |

Examples 13 to 21

In Examples 13 to 21, arylated pyrene was obtained by the reaction of the formula below.

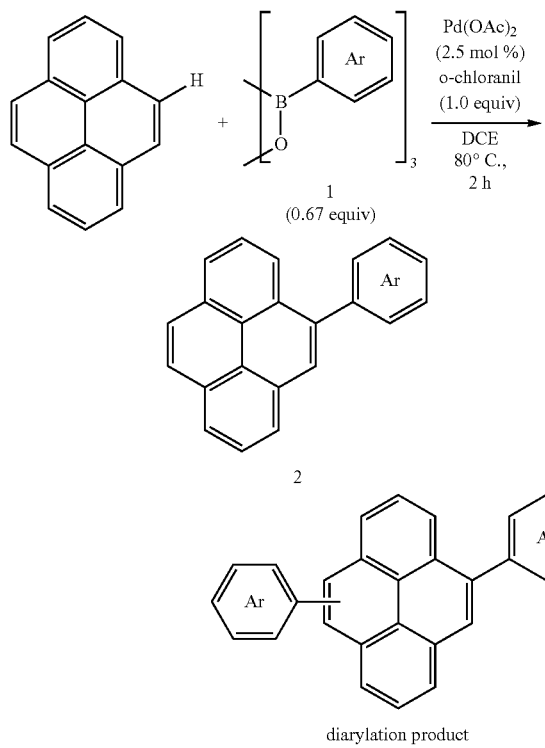

The details are described below.

Example 13

A Pd (OAc)$_2$ solution (1.1 mg, 5.0 μmol, 2.5 mol %), o-chloranil (49 mg, 0.20 mmol, 1 equivalent), pyrene (40 mg, 0.20 mol, 1 equivalent) represented by the formula below:

[Chem. 124]

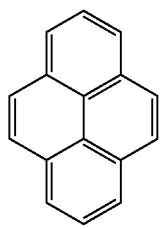

and a boron compound (0.13 mol, 0.67 equivalents) represented by the formula below:

[Chem. 125]

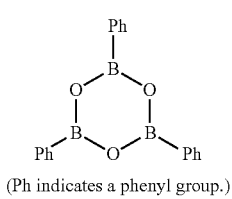

(Ph indicates a phenyl group.)

were introduced into 1,2-dichloroethane (1,2-DCE, 2.0 mL), and the mixture was stirred for 2 hours at 80° C. The reaction product was filtered using a silica gel (eluent (東野さん : 溶離液 OK?): CH$_2$Cl$_2$, 50 mL), and the volatile substance was removed under reduced pressure. The residue was purified by PTLC (eluent: hexane/toluene). As a result, 4-phenyl pyrene (2a) represented by the formula below:

[Chem. 126]

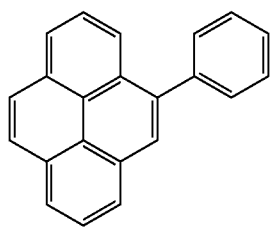

was obtained.

PTLC (hexane only): 2a (28 mg, 50% yield), diarylation product (11 mg, 15% yield), and pyrene (12 mg, 31% yield).
$^1$H NMR (400 MHz, CDCl$_3$) δ 8.20-8.16 (m, 4H), 8.08 (s, 2H), 8.005 (s, 1H), 7.996 (t, J=7.6 Hz, 1H), 7.92 (t, J=8.0 Hz, 1H), 7.66 (d, J=8.0 Hz, 2H), 7.55 (dd, J=8.0, 7.6 Hz, 2H), 7.48 (dd, J=7.6, 7.2 Hz, 1H); $^{13}$C NMR (100 MHz, CDCl$_3$) δ 140.8, 139.5, 131.3, 131.1, 130.8, 130.4, 130.1, 128.4, 127.8, 127.6, 127.5, 127.2, 126.1, 125.7, 125.2, 125.1, 125.0, 124.8, 124.2, 123.9. HRMS (DART, ESI+) m/z calcd for C$_{22}$H$_{14}$ [M+H]$^+$: 279.1174, found: 279.1184. Mp: 131.9-133.5° C.

Example 14

Example 14 was prepared in the same manner as Example 13, except that a boron compound represented by the formula below:

[Chem. 127]

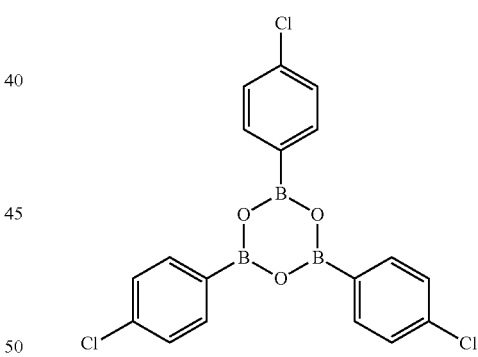

was used as a boron compound. As a result, 4-(4-chlorophenyl)pyrene (2b) represented by the formula below:

[Chem. 128]

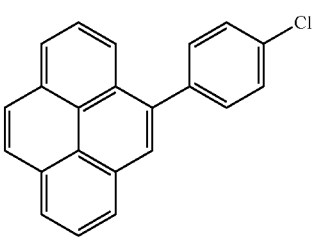

was obtained.

PTLC (hexane only): 2b (30 mg, 49% yield), diarylation product (6.2 mg, 7% yield), and pyrene (11 mg, 26% yield).

$^1$H NMR (600 MHz, CDCl$_3$) δ 8.19 (d, J=7.2 Hz, 2H), 8.17 (d, J=7.2 Hz, 1H), 8.12 (d, J=7.2 Hz, 1H), 8.090 (d, J=9.0 Hz, 1H), 8.089 (d, J=9.0 Hz, 1H), 8.01 (dd, J=7.8, 7.2 Hz, 1H), 7.97 (s, 1H), 7.94 (dd, J=7.8, 7.2 Hz, 1H), 7.58 (d, J=8.4 Hz, 2H), 7.52 (d, J=8.4 Hz, 2H); $^{13}$C NMR (100 MHz, CDCl$_3$) δ139.2, 138.2, 133.5, 131.4, 131.0, 130.6, 130.1, 128.6, 127.9, 127.6, 127.3, 126.1, 125.8, 125.3, 125.14, 125.06, 124.9, 124.2, 123.5. HRMS (DART, ESI+) m/z calcd for C$_{22}$H$_{13}$Cl [M+H]$^+$: 313.0784, found: 313.0784. Mp: 120.5-121.5° C.

Example 15

Example 15 was prepared in the same manner as Example 13, except that a boron compound represented by the formula below:

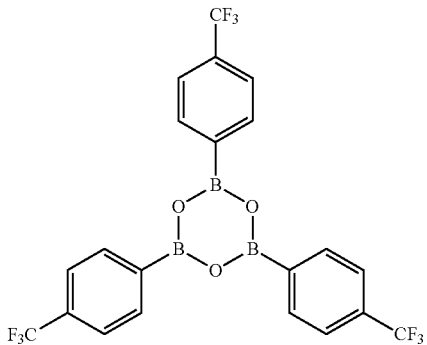

[Chem. 129]

was used as a boron compound. As a result, 4-[4-(trifluoromethyl)phenyl]pyrene (2c) represented by the formula below:

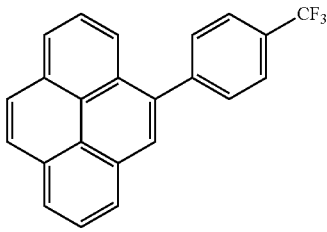

[Chem. 130]

was obtained.

PTLC (hexane only): 2c (37 mg, 53% yield), diarylation product (11 mg, 11% yield), and pyrene (11 mg, 28% yield).

$^1$H NMR (CDCl$_3$, 600 MHz) δ 8.21 (d, J=7.2 Hz, 2H), 8.18, (d, J=7.2 Hz, 1H), 8.10 (s, 2H), 8.08 (d, J=7.8 Hz, 1H), 8.03 (dd, J=7.8, 7.2 Hz, 1H), 7.99 (s, 1H), 7.94 (dd, J=7.8, 7.2 Hz, 1H), 7.81 (d, J=7.8 Hz, 2H), 7.76 (d. J=7.8 Hz, 2H); $^{13}$C NMR (CDCl$_3$, 100 MHz) δ 144.6, 138.0, 131.4, 131.1, 130.5, 130.4, 129.9, 129.7 (q, $^2J_{FC}$=33.5 Hz), 128.1, 127.6, 127.4, 126.2, 125.9, 125.5, 125.4 (q, $^3J_{FC}$=3.8 Hz), 125.32, 125.30, 124.9, 124.34 (q, $^1J_{FC}$=273.4 Hz), 124.32, 123.4. HRMS (DART, ESI+) m/z calcd for C$_{23}$H$_{13}$F$_3$[M+H]$^+$: 347.1048, found: 347.1044. Mp: 145.6-147.1° C.

Example 16

Example 16 was prepared in the same manner as Example 13, except that a boron compound represented by the formula below:

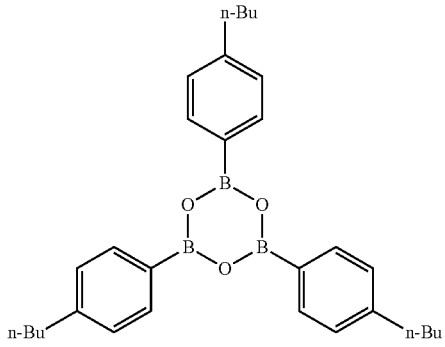

[Chem. 131]

was used as a boron compound. As a result, 4-(4-n-butylphenyl)pyrene (2d) represented by the formula below:

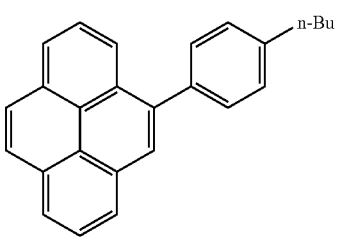

[Chem. 132]

(n-Bu indicates an n-butyl group.)

was obtained.

PTLC (hexane only): 2d (29 mg, 43% yield), diarylation product (9.9 mg, 11% yield), and pyrene (13 mg, 32% yield).

$^1$H NMR (CDCl$_3$, 600 MHz) δ 8.23 (d, J=7.8 Hz, 1H), 8.17 (d, J=7.8 Hz, 1H), 8.16 (d, J=8.4 Hz, 2H), 8.08 (d, J=9.0 Hz, 1H), 8.07 (d, J=9.0 Hz, 1H), 8.00 (s, 1H), 7.99 (dd, J=7.8, 7.2 Hz, 1H), 7.93 (dd, J=7.8, 7.2 Hz, 1H), 7.57 (d, J=7.8 Hz, 2H), 7.36 (d, J=7.8 Hz, 2H), 2.74 (t, J=7.8 Hz, 2H), 1.75 to 1.68 (m, 2H), 1.50-1.42 (m, 2H), 0.99 (t, J=7.8 Hz, 3H); $^{13}$C NMR (CDCl$_3$, 100 MHz) δ 142.2, 139.5, 138.0, 131.3, 131.1, 130.9, 130.5, 129.9, 128.4, 127.7, 127.6, 127.2, 126.1, 125.6, 125.1, 125.0, 124.7, 124.1, 124.0, 35.5, 33.7, 22.5, 14.0. HRMS (DART, ESI+) m/z calcd for C$_{26}$H$_{22}$ [M+H]$^+$: 335.1800, found: 335.1802. Mp: 61.4-62.5° C.

Example 17

Example 17 was prepared in the same manner as Example 13, except that a boron compound represented by the formula below:

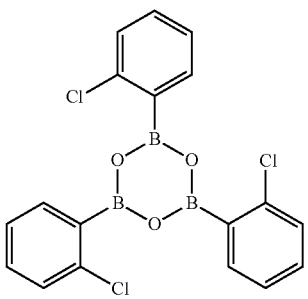

was used as a boron compound. As a result, 4-(2-chlorophenyl)pyrene (2e) represented by the formula below:

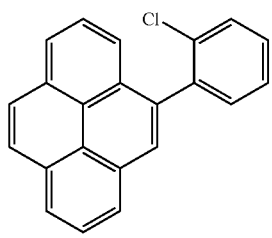

was obtained.

PTLC (hexane only): 2e (32 mg, 52% yield), diarylation product (7.1 mg, 8% yield), and pyrene (15 mg, 37% yield).

$^1$H NMR (CDCl$_3$, 600 MHz) δ 8.18 (d, J=7.2 Hz, 1H), 8.17 (d, J=7.2 Hz, 2H), 8.08 (d, J=8.7 Hz, 1H), 8.07 (d, J=8.7 Hz, 1H), 8.00 (dd, J=7.8, 7.2 Hz, 1H), 7.98 (s, 1H), 7.91 (dd, J=7.8, 7.2 Hz, 1H), 7.78 (d. J=9.0 Hz, 1H), 7.60 (dd, J=7.8, 7.2 Hz, 1H), 7.50 (dd, J=7.8, 7.2 Hz, 1H), 7.44 to 7.40 (m, 2H); $^{13}$C NMR (CDCl$_3$, 100 MHz) δ 139.4, 136.9, 134.3, 132.2, 131.3, 131.1, 130.5, 130.1, 129.7, 129.2, 128.2, 127.6, 127.2, 126.8, 126.1, 125.8, 125.3, 125.2, 124.7, 124.4, 123.7. HRMS (DART, ESI+) m/z calcd for C$_{22}$H$_{13}$Cl [M+H]$^+$: 313.0784, found: 313.0777. Mp: 114.3-115.9° C.

Example 18

Example 18 was prepared in the same manner as Example 13, except that a boron compound represented by the formula below:

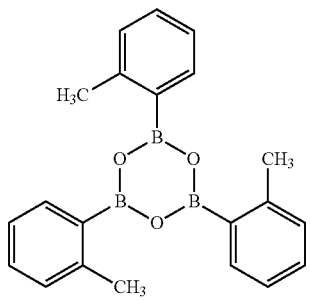

was used as a boron compound. As a result, 4-[2-(trifluoromethyl)phenyl]pyrene (2f) represented by the formula below:

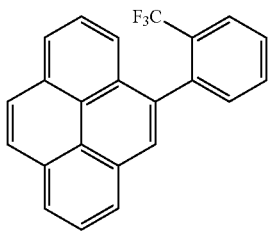

was obtained.

PTLC (hexane only): 2f (42 mg, 61% yield), diarylation product (14 mg, 14% yield), and pyrene (8.0 mg, 20% yield).

$^1$H NMR (CDCl$_3$, 600 MHz) δ 8.19 (d, J=7.8 Hz, 1H), 8.17 (d, J=7.2 Hz, 1H), 8.16 (d, J=7.8 Hz, 1H), 8.09 (s2H), 8.01 (dd, J=7.8, 7.2 Hz, 1H), 7.97 (s, 1H), 7.90 (d, J=8.4 Hz, 1H), 7.88 (dd, J=7.8, 7.2 Hz, 1H), 7.64 (t, J=7.8 Hz, 1H), 7.63 (d, J=7.2 Hz, 1H), 7.59 (t, J=7.2 Hz, 1H), 7.49 (d, J=7.2 Hz, 1H); $^{13}$C NMR (CDCl$_3$, 100 MHz) δ 139.2, 136.1, 132.8, 131.3, 131.2, 131.12, 131.07, 130.2, 130.0 (q, $^2J_{FC}$=30.0 Hz), 128.2, 127.9, 127.6, 127.3, 126.3 (q, $^3J_{FC}$=4.8 Hz), 126.2, 125.7, 125.32, 125.26, 125.1, 124.6, 124.4, 124.1 (q, $^1J_{FC}$=275.4 Hz), 124.0. HRMS (DART, ESI+) m/z calcd for C$_{23}$H$_{13}$F$_3$ [M+H]$^+$: 347.1048, found: 347.1053. Mp: 104.7-106.6° C.

Example 19

Example 19 was prepared in the same manner as Example 13, except that a boron compound represented by the formula below:

[Chem. 137]

was used as a boron compound. As a result, 4-(2-methylphenyl)pyrene (2g) represented by the formula below:

[Chem. 138]

was obtained.

PTLC (hexane only): 2g (31 mg, 53% yield), diarylation product (12 mg, 16% yield), and pyrene (10 mg, 23% yield).

$^1$H NMR (CDCl$_3$, 600 MHz) δ 8.17 (d, J=7.8 Hz, 1H), 8.154 (d, J=7.8 Hz, 1H), 8.149 (d, J=7.8 Hz, 1H), 8.08 (s, 2H), 8.00 (dd, J=7.8, 7.2 Hz, 1H), 7.93 (s, 1H), 7.88 (dd, J=7.8, 7.2 Hz, 1H), 7.76 (d, J=7.8 Hz, 1H), 7.42-7.34 (m, 4H), 2.10 (s, 3H); $^{13}$C NMR (CDCl$_3$, 100 MHz) δ 140.2, 139.2, 137.1, 131.3, 131.1, 130.8, 130.7, 130.4, 130.0, 127.8, 127.6, 127.4, 127.3, 126.1, 125.82, 125.78, 125.1, 125.0, 124.8, 124.7, 124.2, 123.8, 20.1. HRMS (DART, ESI+) m/z calcd for C$_{23}$H$_{16}$ [M+H]$^+$: 293.1330, found: 293.1334. Mp: 112.6-114.6° C.

Example 20

Example 20 was prepared in the same manner as Example 13, except that a boron compound represented by the formula below:

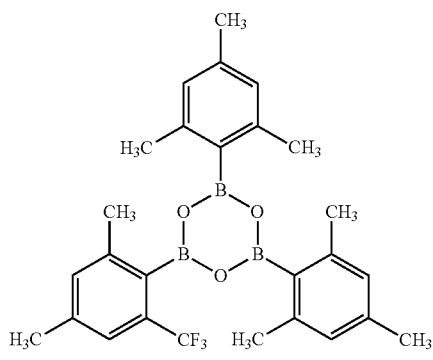
[Chem. 139]

was used as a boron compound. As a result, 4-(2,4,6-trimethylphenyl)pyrene (2h) represented by the formula below:

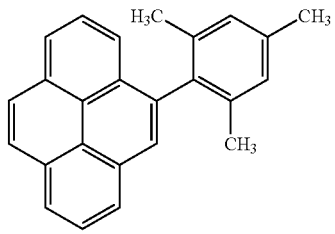
[Chem. 140]

was obtained.

PTLC (hexane only): 2h (35 mg, 54% yield), diarylation product (6.6 mg, 8% yield), and pyrene (7.9 mg, 20% yield).

$^1$H NMR (400 MHz, CDCl$_3$) δ 8.20-8.15 (m, 3H), 8.110 (s, 1H), 8.106 (s, 1H), 8.02 (dd, J=8.0, 7.6 Hz 1H), 7.89 (s, 1H), 7.87 (t, J=8.0 Hz, 1H), 7.70 (d, J=8.0 Hz, 1H), 7.08 (s, 2H), 2.44 (s, 3H), 1.98 (s, 6H); $^{13}$C NMR (100 MHz, CDCl$_3$) δ 138.2, 137.1, 137.0, 136.6, 131.4, 131.2, 131.1, 130.5, 128.2, 127.6, 127.2, 126.0, 125.1, 124.95, 124.91, 124.7, 124.2, 123.1, 21.2, 20.3. HRMS (DRAT, ESI+) m/z calcd for C$_{25}$H$_{20}$ [M+H]$^+$: 321.1643, found: 321.1632. Mp: 78.0-80.0° C.

Example 21

Example 21 was prepared in the same manner as Example 13, except that a boron compound represented by the formula below:

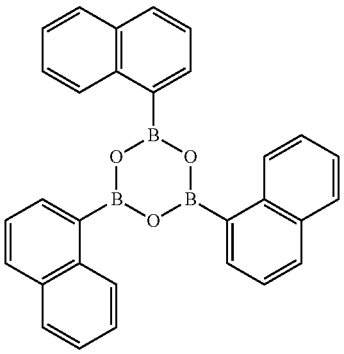
[Chem. 141]

was used as a boron compound. As a result, 4-(naphthalen-1-yl)pyrene (21) represented by the formula below:

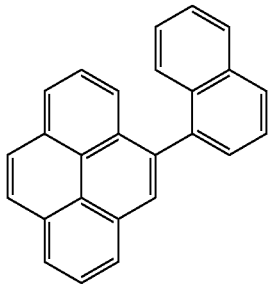
[Chem. 142]

was obtained.

PTLC (hexane/toluene=19:1): 21 (30 mg, 45% yield), and pyrene (16 mg, 39% yield).

$^1$H NMR (CDCl$_3$, 600 MHz) δ 8.22 (d, J=7.2 Hz, 1H), 8.18 (d, J=7.2 Hz, 1H), 8.16 (d, J=7.2 Hz, 1H), 8.12 (s, 2H), 8.10 (s, 1H), 8.03 (dd, J=7.8, 7.2 Hz, 1H), 8.01 to 8.00 (m, 1H), 7.97 (d, J=7.8 Hz, 1H), 7.79 (dd, J=7.8, 7.2 Hz, 1H), 7.69 (d, J=7.2 Hz, 1H), 7.65 to 7.64 (m, 2H), 7.53 (d, J=7.8 Hz, 1H), 7.47 (t, J=7.2 Hz, 1H), 7.23 (t, J=7.2 Hz, 1H); $^{13}$C NMR (CDCl$_3$, 100 MHz) δ 138.5, 137.9, 133.6, 133.0, 131.4, 131.2, 131.1, 130.8, 128.8, 128.2, 128.1, 127.9, 127.6, 127.3, 126.7, 126.2, 126.0, 125.9, 125.8, 125.6, 125.1, 125.0, 124.7, 124.5, 124.4. HRMS (DART, ESI+) m/z calcd for C$_{26}$H$_{16}$ [M+H]$^+$: 329.1330, found: 329.1332. Mp: 158.0-160.0° C.

Examples 22 to 24

In Examples 22 to 24, arylated 2,7-di-tert-butylpyrene was obtained by the reaction of the formula below.

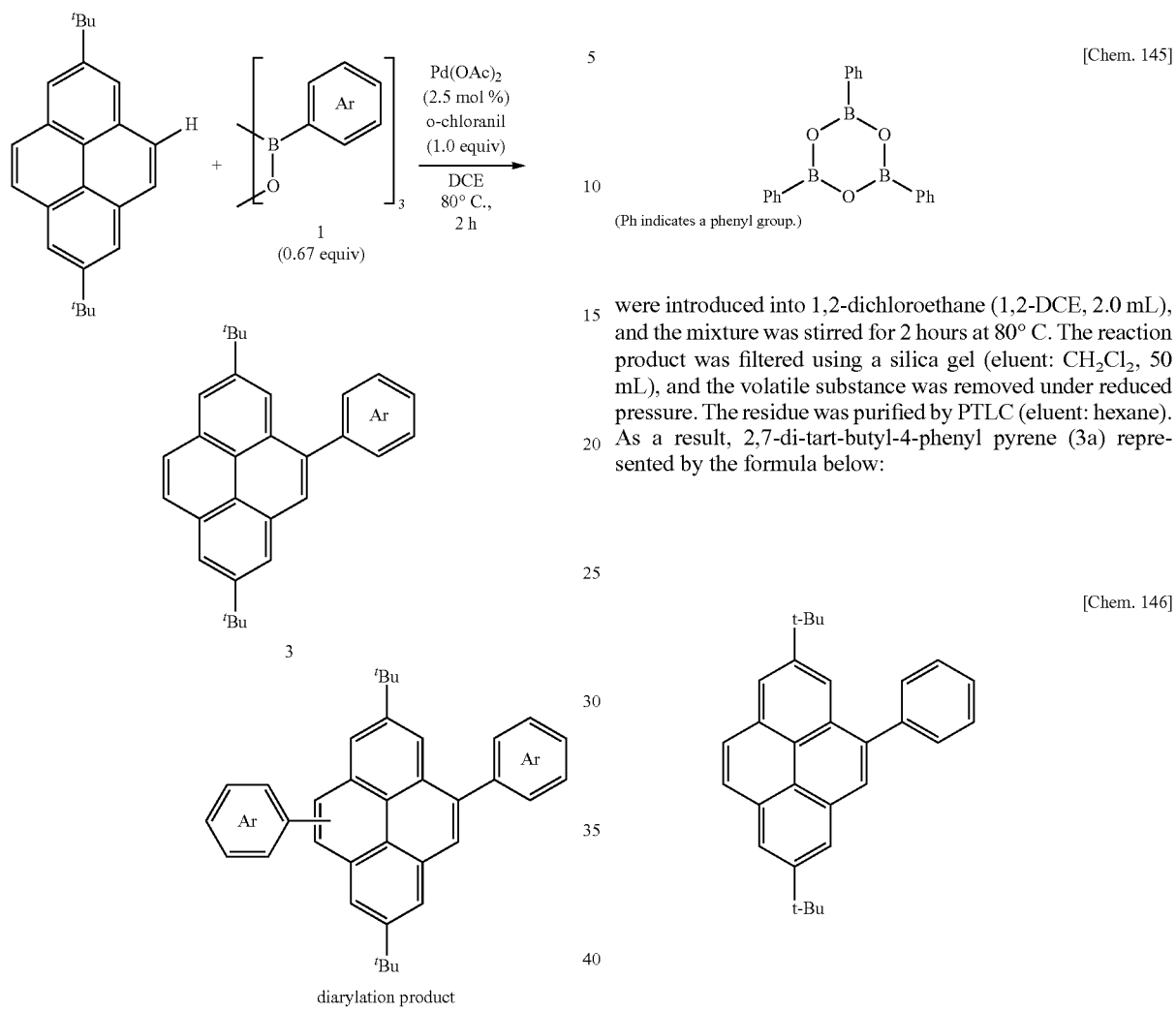

The details are described below.

Example 22

A Pd(OAc)$_2$ solution (1.1 mg, 5.0 μmol, 2.5 mol %), o-chloranil (49 mg, 0.20 mmol, 1 equivalent), 2,7-di-tert-butylpyrene (63 mg, 0.20 mmol, 1 equivalent) represented by the formula below:

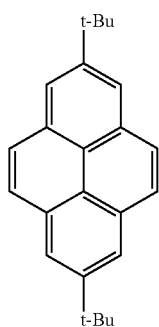

(t-Bu is a t-butyl group.)

and a boron compound (0.13 mmol, 0.67 equivalents) represented by the formula below:

[Chem. 145]

(Ph indicates a phenyl group.)

were introduced into 1,2-dichloroethane (1,2-DCE, 2.0 mL), and the mixture was stirred for 2 hours at 80° C. The reaction product was filtered using a silica gel (eluent: CH$_2$Cl$_2$, 50 mL), and the volatile substance was removed under reduced pressure. The residue was purified by PTLC (eluent: hexane). As a result, 2,7-di-tart-butyl-4-phenyl pyrene (3a) represented by the formula below:

[Chem. 146]

(t-Bu is a t-butyl group.)

was obtained.

Yield: 3a (38 mg, 49% yield) and diarylation product (19 mg, 20% yield).

$^1$H NMR (CDCl$_3$, 400 MHz) δ 8.25 (s, 1H), 8.199 (s, 1H), 8.195 (s, 1H), 8.189 (s, 1H), 8.05 (d, J=9.2 Hz, 1H), 8.04 (d, J=9.2 Hz, 1H), 7.98 (s, 1H), 7.70 (d, J=8.3 Hz, 2H), 7.57 (dd, J=8.0, 7.6 Hz, 2H), 7.49 (t, J=8.0 Hz, 1H), 1.58 (s, 9H), 1.47 (s, 9H); $^{13}$C NMR (CDCl$_3$, 100 MHz) δ 148.8, 148.3, 141.1, 139.5, 131.0, 130.8, 130.5, 130.0, 129.9, 128.4, 128.0, 127.7, 127.4, 127.3, 123.2, 122.4, 122.13, 122.11, 121.9, 121.0, 35.3, 35.2, 31.9, 31.8. HRMS (DART, ESI+) m/z calcd for C$_{30}$H$_{30}$ [M+H]$^+$: 391.2426, found: 391.2459. Mp: 95.2-97.2° C.

Example 23

Example 23 was prepared in the same manner as Example 22, except that a boron compound represented by the formula below:

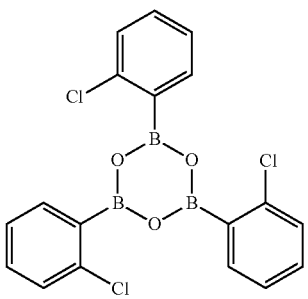

was used as a boron compound. As a result, 2,7-di-tert-butyl-4-(2-chlorophenyl)pyrene (3e) represented by the formula below:

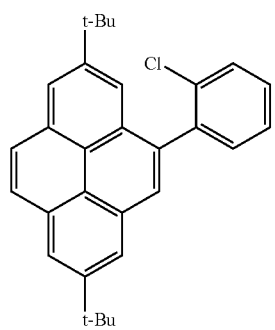

was obtained.

Yield: 3e (47 mg, 55% yield) and diarylation product (9.9 mg, 9% yield).

$^{1}$H NMR (CDCl$_3$, 400 MHz) δ 8.21-8.19 (m, 3H), 8.05 (s, 2H), 7.95 (s, 1H), 7.80 (d, J=1.6 Hz, 1H), 7.63-7.61 (m, 1H), 7.56-7.54 (m, 1H), 7.47-7.44 (m, 2H), 1.58 (s, 9H), 1.44 (s, 9H); $^{13}$C NMR (CDCl$_3$, 100 MHz) δ148.8, 148.4, 139.6, 137.0, 134.3, 132.3, 130.9, 130.8, 130.1, 129.6, 129.5, 129.0, 128.3, 127.7, 127.2, 126.8, 122.8, 122.6, 122.3, 122.1, 121.0, 35.21, 35.18, 31.9, 31.8. HRMS (DART, ESI+) m/z calcd for C$_{30}$H$_{29}$Cl [M+H]$^{+}$: 425.2036, found: 425.2026. Mp: 116.7-117.7° C.

Example 24

Example 24 was prepared in the same manner as Example 22, except that a boron compound represented by the formula below:

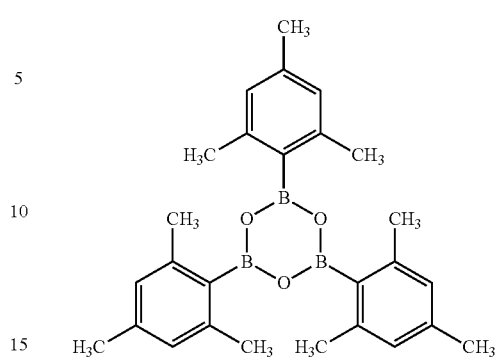

was used as a boron compound. As a result, 2,7-di-tert-butyl-4-(2,4,6-trimethylphenyl)pyrene (3h) represented by the formula below:

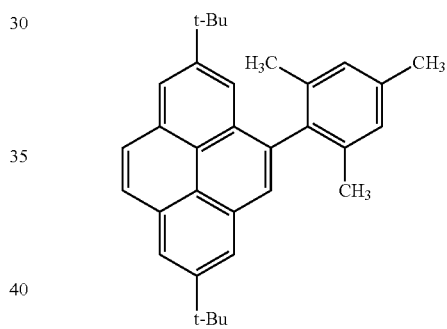

was obtained.

Yield: 3h (61 mg, 71% yield) and diarylation product (17 mg, 16% yield).

$^{1}$H NMR (CDCl$_3$, 400 MHz) δ 8.20 (s, 1H), 8.17 (s, 1H), 8.14 (s, 1H), 8.05 (s, 2H), 7.81 (s, 1H), 7.69 (s, 1H), 7.06 (s, 2H), 2.44 (s, 3H), 1.98 (s, 6H), 1.58 (s, 9H), 1.41 (s, 9H); $^{13}$C NMR (CDCl$_3$, 100 MHz) δ148.7, 148.6, 138.2, 137.0, 136.7, 130.9, 130.8, 130.1, 128.1, 127.7, 127.6, 127.2, 123.1, 122.4, 121.9, 121.82, 121.78, 120.3, 35.2, 35.1, 32.0, 31.8, 21.2, 20.3. HRMS (DART, ESI+) m/z calcd for C$_{33}$H$_{37}$[M+H]$^{+}$: 433.2895, found: 433.2862. Mp: 122.5-124.4° C.

Examples 25 to 27

In Examples 25 to 27, diarylated 2,7-di-tert-butylpyrene was obtained by the reaction of the formula below.

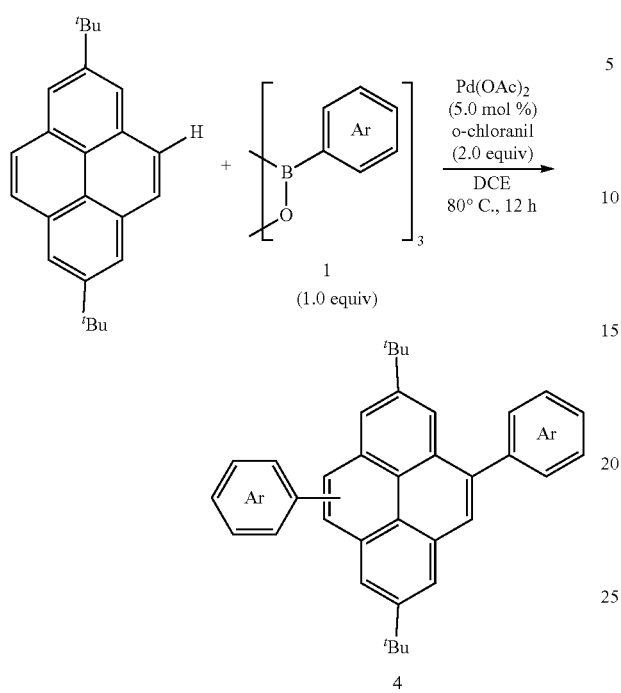

The details are described below.

Example 25

A Pd(OAc)$_2$ solution (2.2 mg, 10 μmol, 5.0 mol %), o-chloranil (98 mg, 0.40 mmol, 2 equivalents), 2,7-di-tert-butylpyrene (63 mg, 0.20 mmol, 1 equivalent) represented by the formula below:

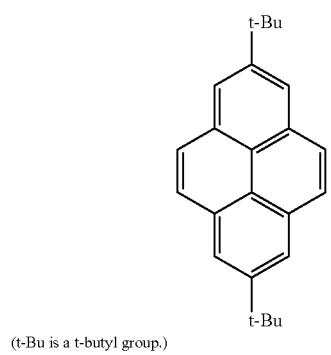

(t-Bu is a t-butyl group.)

and a boron compound (0.20 mmol, 1 equivalent) represented by the formula below:

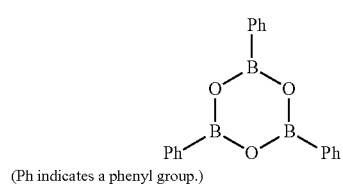

(Ph indicates a phenyl group.)

were introduced into 1,2-dichloroethane (1,2-DCE, 3.0 mL), and the mixture was stirred for 12 hours at 80° C. The reaction product was filtered using a silica gel (eluent: CH$_2$Cl$_2$, 50 mL), and the volatile substance was removed under reduced pressure. The residue was purified by PTLC (eluent: hexane). As a result, 2,7-di-tert-butyl-4,9-di-phenyl pyrene and 2,7-di-tert-butyl-4,10-di-phenyl pyrene (4a) represented by the formula below:

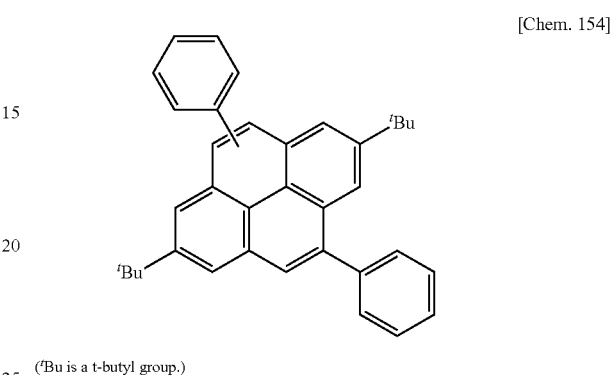

($^t$Bu is a t-butyl group.)

were obtained.

Yield: 77 mg (83% yield), Regioisomer ratio: 4,9–/4,10– =1.1:1

$^1$H NMR (CDCl$_3$, 400 MHz) δ 8.27 (s, 4H), 8.21 (s, 2H), 8.20 (s, 2H), 8.02 (s, 2H), 8.00 (s, 2H), 7.71 (t, J=7.9 Hz, 8H), 7.59-7.56 (m, 8H), 7.51-7.48 (m, 4H), 1.85 (s, 9H), 1.47 (s, 18H), 1.36 (s, 9H); $^{13}$C NMR (CDCl$_3$, 100 MHz) δ 149.1, 148.6, 148.0, 141.2, 141.1, 139.7, 139.3, 130.7, 130.3, 130.07, 130.05, 130.0, 129.9, 128.4, 128.3, 127.9, 127.4, 123.5, 122.7, 122.3, 122.1, 121.1, 120.9, 35.4, 35.3, 35.2, 31.9, 31.8, 31.7. HRMS (DART, ESI+) m/z calcd for C$_{36}$H$_{35}$ [M+H]$^+$: 467.2739, found: 467.2713.

Example 26

Example 26 was prepared in the same manner as Example 25, except that a boron compound represented by the formula below:

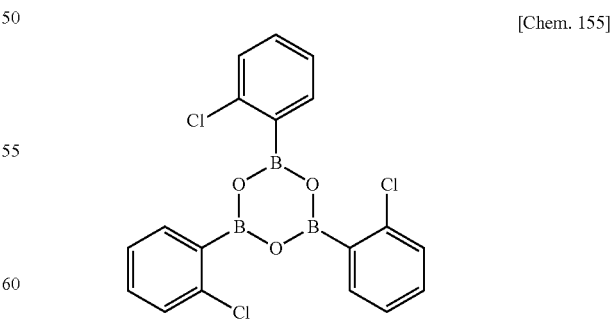

was used as a boron compound. As a result, 2,7-di-tert-butyl-4,9-bis(2-chlorophenyl)pyrene and 2,7-di-tert-butyl-4,10-bis(2-chlorophenyl)pyrene (4e) represented by the formula below:

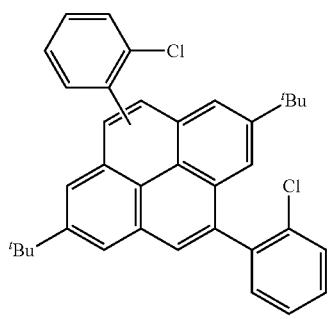

(<sup>t</sup>Bu indicates a t-butyl group.)

were obtained.

Yield: 60 mg (56%), Regioisomer ratio: 4,9–/4,10–=1.1:1

$^1$H NMR (CDCl$_3$, 400 MHz) δ 8.23 (s, 2H), 8.21 (s, 2H), 7.99 (s, 2H), 7.98 (s, 2H), 7.84 (s, 2H), 7.82 (s, 2H), 7.64-7.60 (m, 4H), 7.59-7.52 (m, 4H), 7.48-7.43 (m, 8H), 1.58 (s, 9H), 1.44 (s, 18H), 1.30 (s, 9H); $^{13}$C NMR (CDCl$_3$, 100 MHz) δ149.0, 148.7, 148.7, 139.69, 139.66, 139.6, 137.2, 137.1, 136.8, 134.3, 132.3, 130.3, 130.1, 129.7, 129.6, 129.6, 129.49, 129.46, 128.6, 128.3, 128.2, 126.82, 126.78, 126.7, 122.6, 122.4, 121.3, 121.1, 121.0, 35.2, 31.9, 31.8, 31.6. HRMS (DART, ESI+) m/z calcd for C$_{36}$H$_{33}$Cl$_2$[M+H]$^+$: 535.1959, found: 535.1991.

Example 27

Example 27 was prepared in the same manner as Example 25, except that a boron compound represented by the formula below:

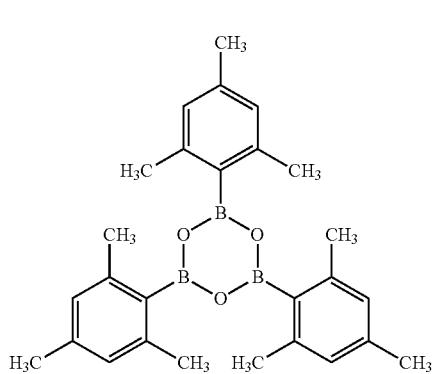

was used as a boron compound. As a result, 2,7-di-tert-butyl-4,9-bis(2,4,6-trimethylphenyl)pyrene and 2,7-di-tert-butyl-4,10-bis(2,4,6-trimethylphenyl)pyrene (4h) represented by the formula below:

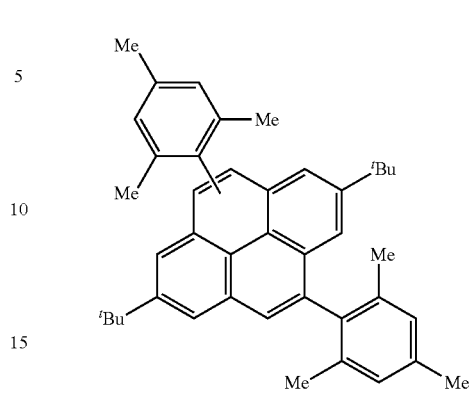

(<sup>t</sup>Bu indicates a t-butyl group. Me indicates a methyl group.)
were obtained.

Yield: 88 mg (80% yield), Regioisomer ratio: 4,9–/4,10–=1:1.5.

$^1$H NMR of 2,7-di-tert-butyl-4,9-bis(2,4,6-trimethylphenyl)pyrene (CDCl$_3$, 400 MHz): δ 8.14 (d, J=2.0 Hz, 2H), 7.85 (s, 2H), 7.71 (d, J=2.0 Hz, 2H), 7.08 (s, 4H), 2.45 (s, 6H), 2.03 (s, 12H), 1.42 (s, 18H). $^1$H NMR of 2,7-di-tert-butyl-4,10-bis(2,4,6-trimethylphenyl)pyrene (CDCl$_3$, 400 MHz): δ 8.17 (s, 2H), 7.84 (s, 2H), 7.67 (s, 2H), 7.07 (s, 4H), 2.44 (s, 6H), 2.02 (s, 12H), 1.60 (s, 9H), 1.24 (s, 9H). $^{13}$C NMR of the mixture (CDCl$_3$, 100 MHz) δ148.7, 148.6, 148.5, 138.4, 138.0, 137.1, 137.0, 136.9, 136.7, 136.6, 130.9, 130.7, 130.3, 130.1, 128.1, 127.9, 127.4, 123.4, 122.7, 121.7, 121.6, 120.1, 35.2, 35.1, 35.0, 32.0, 31.9, 31.7, 21.2, 20.4. HRMS (DART, ESI+) m/z calcd for C$_{42}$H$_{47}$[M+H]$^+$: 551.3678, found: 551.3685.

Examples 28 to 30

In Examples 28 to 30, arylated phenanthrene was obtained by the reaction of the formula below.

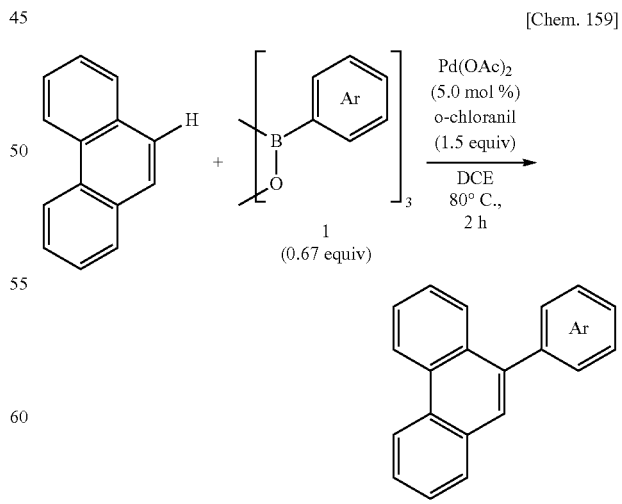

The details are described below.

Example 28

A Pd(OAc)$_2$ solution (2.2 mg, 10 μmol, 5.0 mol %), o-chloranil (74 mg, 0.30 mmol, 1.5 equivalents), phenanthrene (36 mg, 0.20 mmol, 1 equivalent) represented by the formula below:

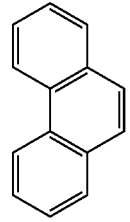
[Chem. 160]

and a boron compound (0.13 mol, 0.67 equivalents) represented by the formula below:

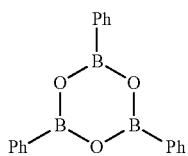
[Chem. 161]

(Ph indicates a phenyl group.)

were introduced into 1,2-dichloroethane (1,2-DCE, 1.0 mL), and the mixture was stirred for 12 hours at 80° C. The reaction product was filtered using a silica gel (eluent: CH$_2$Cl$_2$, 50 mL), and the volatile substance was removed under reduced pressure. The residue was purified by PTLC (eluent: hexane). As a result, 9-phenyl phenanthrene (5a) represented by the formula below:

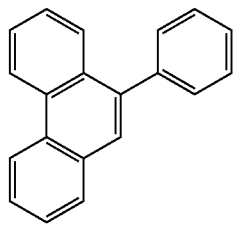
[Chem. 162]

was obtained.

Yield: 5a (33 mg, 64% yield). The spectral data of 9-phenylphenanthrene (5a) has been reported from Oi et al. (Kawai, H.; Kobayashi, Y.; Oi, S.; Inoue, Y. Chem. Commun. 2008, 1464).

Example 29

Example 29 was prepared in the same manner as Example 28, except that a boron compound represented by the formula below:

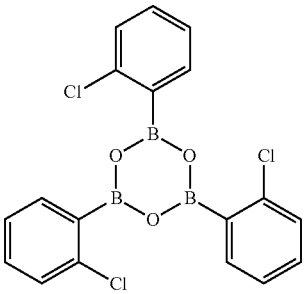
[Chem. 163]

was used as a boron compound. As a result, 9-(2-chlorophenyl)phenanthrene (5e) represented by the formula below:

[Chem. 164]

was obtained.

Yield: 5e (47 mg, 81% yield).

$^1$H NMR (CDCl$_3$, 600 MHz) δ 8.74 (d, J=8.4 Hz, 1H), 8.71 (d, J=8.4 Hz, 1H), 7.87 (d, J=7.2 Hz, 1H), 7.67-7.64 (m, 3H), 7.59 (dd, J=7.8, 7.2 Hz, 1H), 7.54 (d, J=7.2 Hz, 1H), 7.52-7.48 (m, 2H), 7.41-7.34 (m, 3H); $^{13}$C NMR (CDCl$_3$, 100 MHz) δ 139.3, 136.1, 134.3, 132.1, 131.3, 130.8, 130.2, 129.5, 129.1, 128.7, 127.8, 126.85, 126.81, 126.70, 126.67, 126.6, 126.5, 122.9, 122.6. HRMS (DART, ESI+) m/z calcd for C$_{20}$H$_{13}$Cl [M+H]$^+$: 289.0784, found: 289.0790. Mp: 118.9-120.1° C.

Example 30

Example 30 was prepared in the same manner as Example 28, except that a boron compound represented by the formula below:

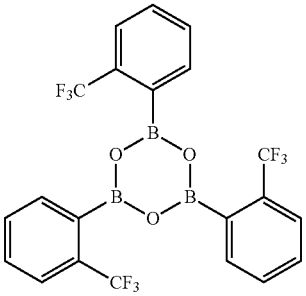
[Chem. 165]

was used as a boron compound. As a result, 9-[2-(trifluoromethyl)phenyl]phenanthrene (5f) represented by the formula below:

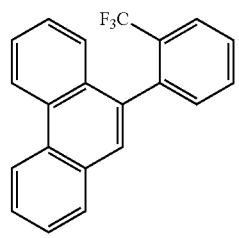

was obtained.

Yield: 5f (51 mg, 79% yield).

$^1$H NMR (CDCl$_3$, 600 MHz) δ 8.74 (d, J=8.4 Hz, 1H), 8.72 (d, J=8.4 Hz, 1H), 7.87 (d, J=7.2 Hz, 1H), 7.85 (d, J=8.4 Hz, 1H), 7.67 (dd, J=8.4, 7.2 Hz, 1H), 7.64-7.59 (m, 4H), 7.55 (dd, J=7.8, 7.2 Hz, 1H), 7.47 (dd, J=7.2, 6.6 Hz, 1H), 7.40 (d, J=7.8 Hz, 1H), 7.36 (d, J=8.4 Hz, 1H); $^{13}$C NMR (CDCl$_3$, 100 MHz) δ 139.2, 135.4, 132.7, 131.8, 131.2, 131.0, 130.19, 130.16, 129.8 (q, $^2J_{FC}$=30.0 Hz), 128.8, 127.82, 127.79, 127.0, 126.9, 126.5, 126.4, 126.2 (q, $^3J_{FC}$=5.1 Hz), 124.0 (q, $^1J_{FC}$=275.3 Hz), 122.7, 122.6. HRMS (DART, ESI+) m/z calcd for C$_{21}$H$_{13}$F$_3$ [M+H]$^+$: 323.1048, found: 323.1050. Mp: 104.7-106.6° C.

Example 31

In Example 31, the conjugated system was extended by the reaction of the formula below.

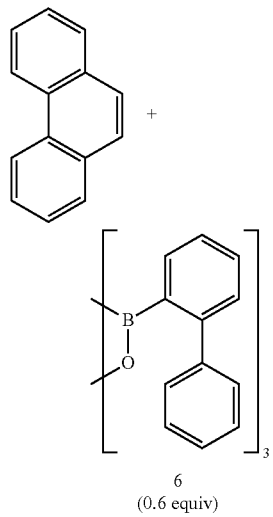

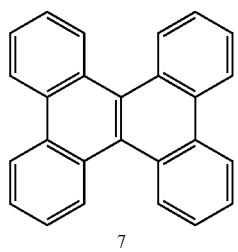

The details are described below.

A Pd(OAc)$_2$ solution (2.2 mg, 10 μmol, 5.0 mol %), o-chloranil (59 mg, 0.24 mmol, 1.2 equivalents), phenanthrene (36 mg, 0.20 mmol, 1 equivalent) represented by the formula below:

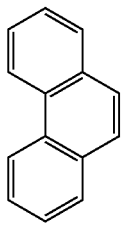

and a boron compound (64 mg, 0.12 mmol, 0.6 equivalents) represented by the formula below:

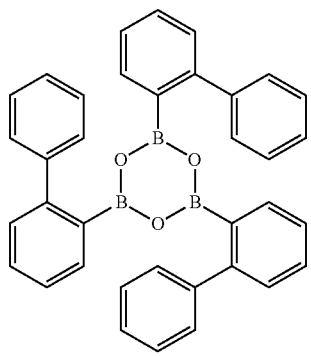

were introduced into 1,2-dichloroethane (1,2-DCE, 2.0 mL), and the mixture was stirred for 12 hours at 80° C. The reaction product was filtered using a silica gel (eluent: CH$_2$Cl$_2$. 50 mL), and the volatile substance was removed under reduced pressure. The residue was purified by PTLC (eluent: hexane/CH$_2$Cl$_2$=10:1). As a result, 46 mg of 9-(o-biphenyl)phenyl phenanthrene represented by the formula below:

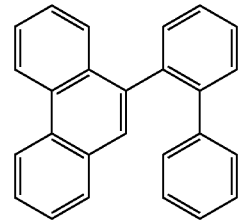

was obtained (yield: 70%).

A nitromethane solution (1.0 mL) of FeCl$_3$ (41 mg, 0.25 mmol, 5 equivalents) was added to a CH$_2$Cl$_2$ solution (0.5 mL) of 9-(o-biphenyl)phenyl phenanthrene (17 mg, 0.05 mmol, 1 equivalent) at room temperature. After the mixture was stirred for 12 hours, methanol (2 mL) was added to the reaction product. The mixture was passed through the silica gel layer, and further washed with CH$_2$Cl$_2$. The volatile substance was removed under reduced pressure, and the residue was purified by PTLC (eluent: hexane/CH$_2$Cl$_2$=10:1). As a result, dibenzo[g,p]chrysene(7) represented by the formula below:

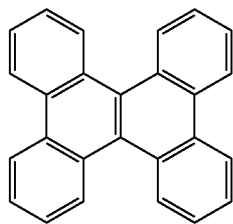

was obtained (14 mg, yield: 60% in two steps). Spectral data of dibenzo[g,p]chrysene(7) have been reported from Liu et al. (Li, C.-W.; Wang, C.-I.; Liao, H.-Y.; Chaudhuri, R.; Liu, R.-S. J. Org. Chem. 2007, 72, 9203).

Example 32

In Example 32, the conjugated system was extended by the reaction of the formula below.

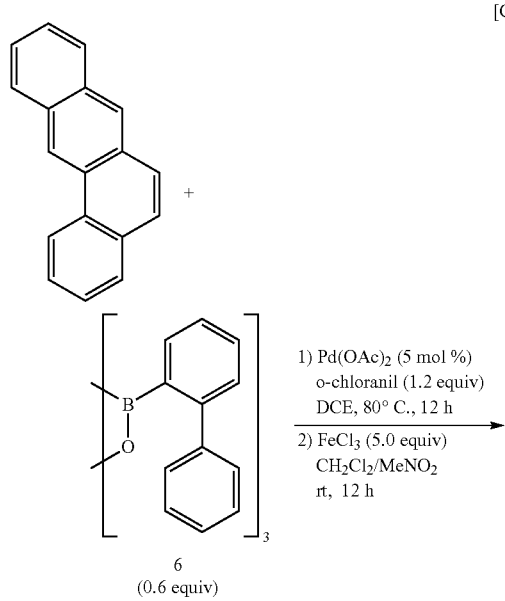

The details are described below.

A Pd(OAc)$_2$ solution (2.2 mg, 10 μmol, 5.0 mol %), o-chloranil (59 mg, 0.24 mmol, 1.2 equivalents), benzo[a]anthracene (46 mg, 0.20 mmol, 1 equivalent) represented by the formula below:

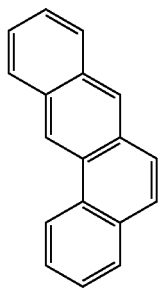

and a boron compound (64 mg, 0.12 mmol, 0.6 equivalents) represented by the formula below:

[Chem. 174]

were introduced into 1,2-dichloroethane (1,2-DCE, 2.0 mL), and the mixture was stirred for 12 hours at 80° C. The reaction product was filtered using a silica gel (eluent: CH$_2$Cl$_2$, 50 mL), and the volatile substance was removed under reduced pressure. The residue was purified by PTLC (eluent: hexane/CH$_2$Cl$_2$=10:1). As a result, biphenylated benzo[a]anthracene was obtained as a mixture of position isomers (43 mg, yield 57% in total).

A nitromethane solution (1.0 mL) of FeCl$_3$ (41 mg, 0.25 mmol, 5 equivalents) was added at room temperature to a CH$_2$Cl$_2$ solution (0.5 mL) of biphenylated benzo[a]anthracene (19 mg, 0.05 mmol, 1 equivalent). After the mixture was stirred for 12 hours, methanol (2 mL) was added to the reaction product. The mixture was passed through the silica gel layer, and further washed with CH$_2$Cl$_2$. The volatile substance was removed under reduced pressure. The residue was purified by PTLC (eluent: hexane/CH$_2$Cl$_2$=10:1). As a result, tribenzo[a,c,f]tetraphene (8) represented by the formula below:

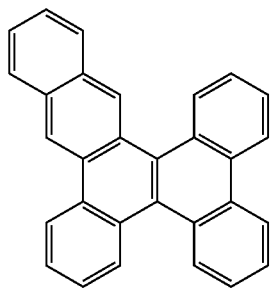

was obtained (4 mg, yield: 12% in two steps).

$^1$H NMR (CDCl$_3$, 400 MHz) δ 9.13 (d, J=4.1 Hz, 2H), 8.88 (d, J=8.2 Hz, 1H), 8.82 (d, J=7.2 Hz, 1H), 8.76-8.69 (m, 3H), 8.61 (t, J=8.4 Hz, 1H), 8.15 (d, J=7.7 Hz, 1H), 8.03 (d, J=7.7 Hz, 1H), 7.74-7.54 (m, 8H); $^{13}$C NMR (CDCl$_3$, 100 MHz) δ 132.0, 131.6, 131.3, 131.0, 130.9, 129.9, 129.8, 129.3, 129.2, 129.1, 128.62, 128.57, 128.3, 128.2, 128.0, 127.9, 127.7, 127.0, 126.9, 126.8, 126.62, 126.57, 126.2, 125.9, 124.2, 123.7, 123.6, 122.3. HRMS (DART, ESI+) m/z calcd for C$_{30}$H$_{18}$[M+H]$^+$: 379.1487, found: 379.1496. Mp: 114.0-116.0° C.

Example 33

In Example 33, the conjugated system was extended by the reaction of the formula below.

[Chem. 176]

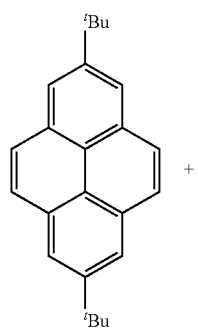

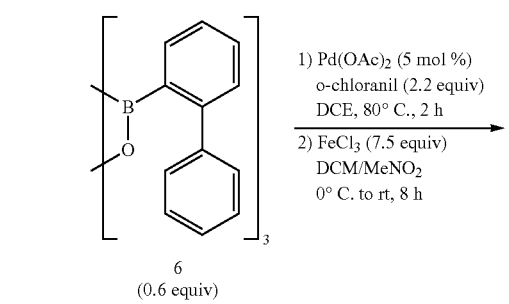

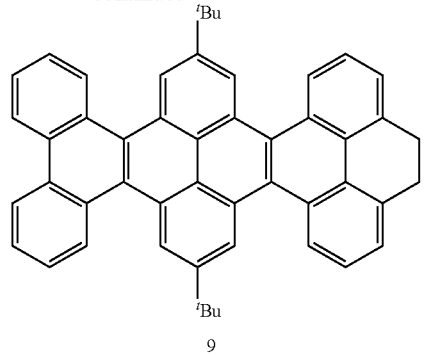

9

The details are described below.

A Pd(OAc)$_2$ solution (36 mg, 0.16 mmol, 5.0 mol %), o-chloranil (1.7 g, 7.0 mmol, 2.2 equivalents), 2,7-di-tert-butylpyrene (1.0 g, 3.2 mmol, 1 equivalent) represented by the formula below:

[Chem. 177]

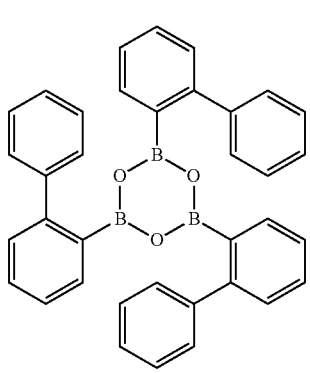

(t-Bu is a t-butyl group.)

and a boron compound (1.7 g, 7.0 mmol, 1 equivalent) represented by the formula below:

[Chem. 178]

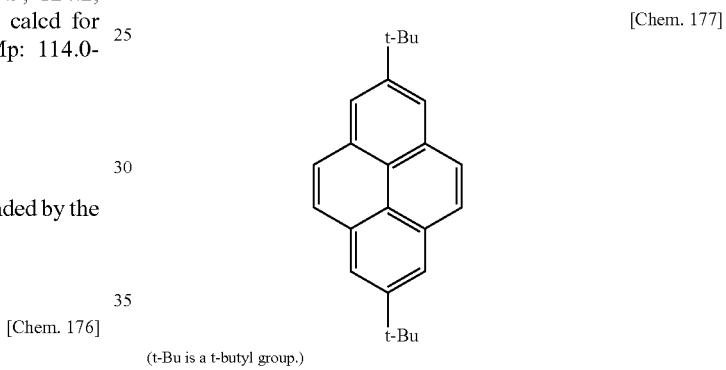

were introduced into 1,2-dichloroethane (1,2-DCE, 30 mL), and the mixture was stirred for 2 hours at 80° C. The reaction product was filtered using a silica gel (eluent: CH$_2$Cl$_2$, 100 mL), and the volatile substance was removed under reduced pressure. The residue was purified by PTLC (eluent: hexane/CH$_2$Cl$_2$=9:1). As a result, 2,7-di-tert-butylpyrene diarylated with biphenyl was obtained as a mixture of position isomers (1.4 g, yield: 73%).

A nitromethane solution (30 mL) of FeCl$_3$ (2.8 g, 17 mmol, 7.5 equivalents) was added at 0° C. to a CH$_2$Cl$_2$ solution (200 mL) of diarylated compound (1.4 g, 2.3 mmol, 1 equivalent). After the mixture was stirred for 8 hours, methanol (30 mL) was added to the reaction product. After being removed, the solvent was passed through the silica gel layer and washed with CH$_2$Cl$_2$. The volatile substance was removed under reduced pressure. The residue was dissolved in CH$_2$Cl$_2$, and the resulting solution was poured into methanol. As a result, 10,21-di-tert-butylhexabenzo[a,c,fg,j,l,op]tetracene (9) represented by the formula below:

[Chem. 179]

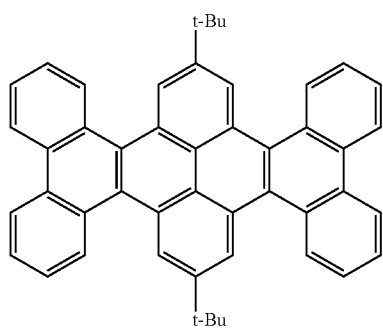

was obtained (1.2 g, yield: 60% in two steps).

$^1$H NMR (CDCl$_3$, 600 MHz) δ 9.05 (s, 4H), 8.90 (d, J=8.3 Hz, 4H), 8.82 (d, J=8.2 Hz, 4H), 7.76 (dd, J=8.2, 6.8 Hz, 4H), 7.70 (dd, J=8.3, 6.8 Hz, 4H), 1.61 (s, 18H); $^{13}$C NMR (CDCl$_3$, 100 MHz) δ147.7, 131.0, 129.9, 128.5, 128.3, 127.9, 126.7, 126.6, 123.8, 123.4, 122.8, 35.7, 31.7. HRMS (DART, ESI+) m/z calcd for C$_{46}$H$_{38}$ [M+H]$^+$: 615.3052, found: 615.3067. Mp: 260-265° C. (decompose).

Example 34

In Example 34, the conjugated system was extended by the reaction of the formula below:

[Chem. 180]

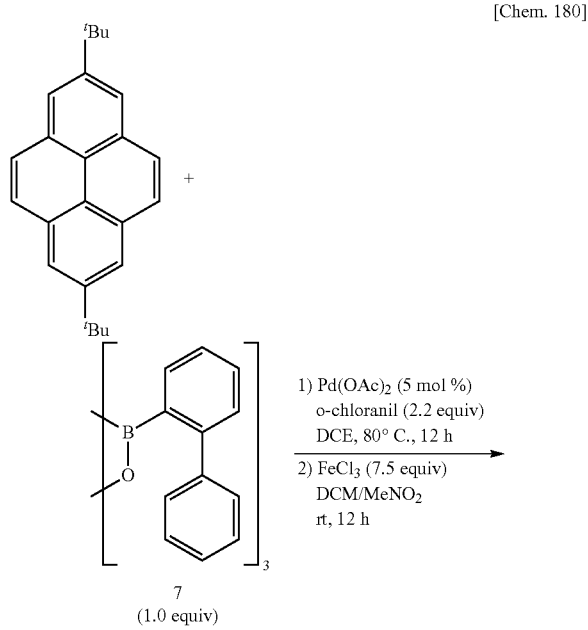

-continued

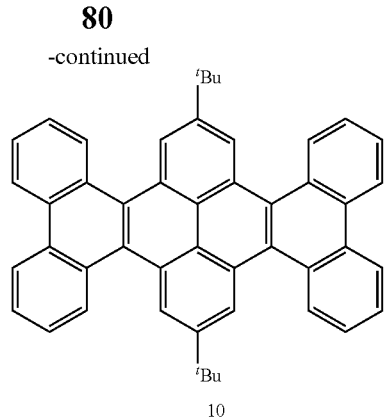

The details are described below.

A Pd(OAc)$_2$ solution (1.1 mg, 5 μmol, 5.0 mol %), o-chloranil (54 mg, 0.22 mmol, 2.2 equivalents), 2,7-di-tert-butylpyrene (31 mg, 0.10 mmol, 1 equivalent) represented by the formula below:

[Chem. 181]

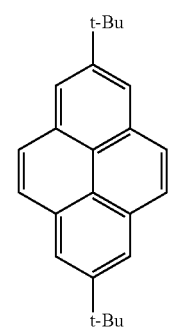

(t-Bu is a t-butyl group.)

and a boron compound (54 mg, 0.10 enol, 1 equivalent) represented by the formula below:

[Chem. 182]

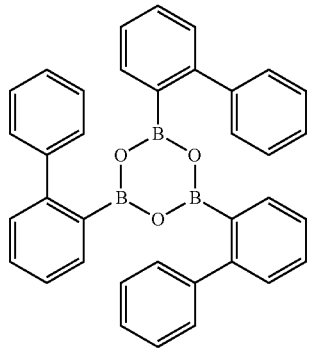

were introduced into 1,2-dichloroethane (1,2-DCE, 1.0 mL), and the mixture was stirred for 12 hours at 80° C. The reaction product was filtered using a silica gel (eluent: CH$_2$Cl$_2$, 50 mL), and the volatile substance was removed under reduced pressure. The residue was purified by PTLC (eluent: hexane/CH$_2$Cl$_2$=10:1). As a result, 2,7-di-tert-butylpyrene diarylated with biphenyl was obtained as a mixture of position isomers (31 mg, yield: 82%).

A nitromethane solution (0.2 mL) of FeCl$_3$ (24 mg, 0.15 mmol, 7.5 equivalents) was added at room temperature to a CH$_2$Cl$_2$ solution (1.5 mL) of the diarylated compound (12 mg, 0.02 mol, 1 equivalent). After the mixture was stirred for 12 hours, methanol (2 mL) was added to the reaction product. The mixture was passed through the silica gel layer and further washed with CH$_2$Cl$_2$. The volatile substance was removed under reduced pressure. The residue was purified by PTLC (eluent: hexane/CH$_2$Cl$_2$=10:1). As a result, 10,21-di-tart-butylhexabenzo[a,c,fg,j,l,op]tetracene (9) represented by the formula below:

[Chem. 183]

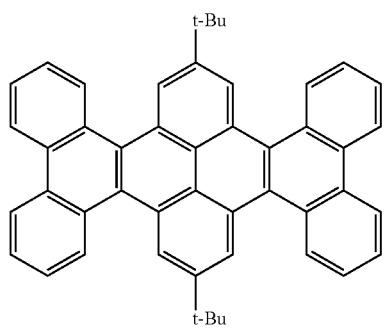

was obtained (12 mg, yield: 82% in two steps)

Reference Example 1

X-Ray Structure Analysis of 4-phenyl pyrene (2a), 4-(2,4,6-trimethylphenyl)pyrene (2h), and tribenzo[a,c,f]tetraphene (8)

Figure 2:
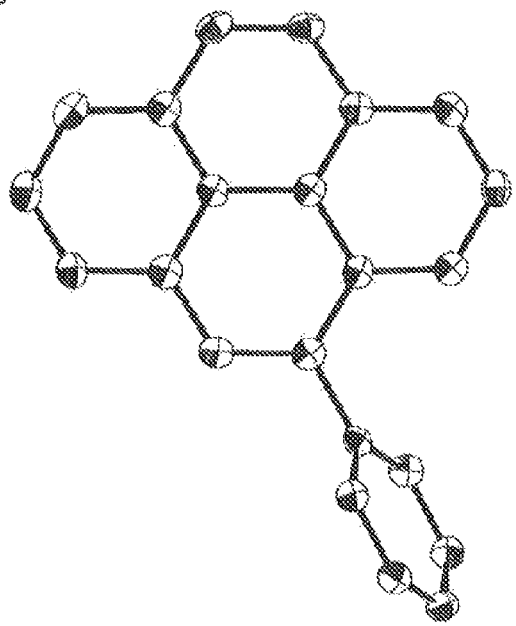
FIG. 2 is a drawing showing a structure of 4-phenylpyrene (2a), produced using the Oak Ridge Thermal Ellipsoid Plot (ORTEP) program (50% probability ellipsoids).
Figure 3:
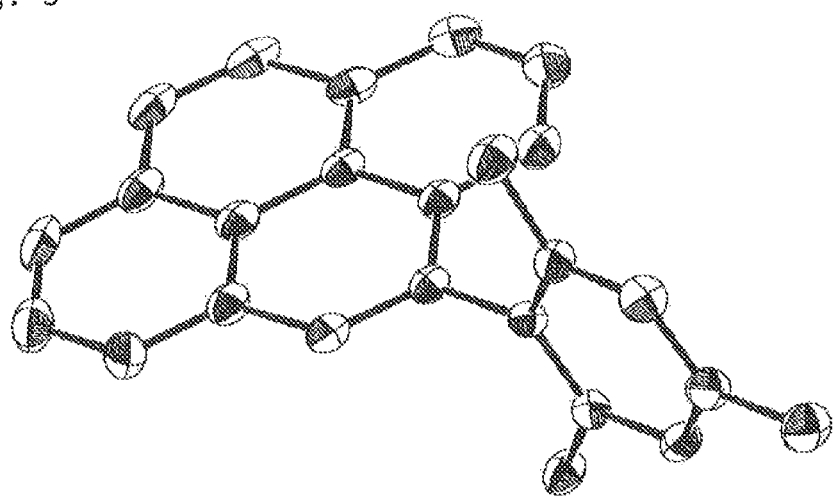
FIG. 3 is a drawing showing a structure of 4-(2,4,6-trimethyl phenyl)pyrene (2h), produced using the Oak Ridge Thermal Ellipsoid Plot (ORTEP) program (50% probability ellipsoids).
Figure 4:
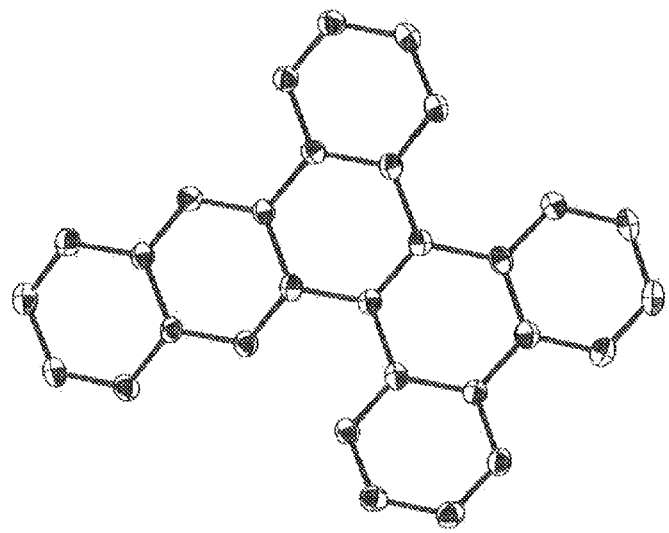
FIG. 4 is a drawing showing a structure of tribenzo[a,c,f]tetraphen (8), produced using the Oak Ridge Thermal Ellipsoid Plot (ORTEP) program (50% probability ellipsoids).

Using "Saturn" (trade name, CCD single-crystal automatic X-ray structure analysis device produced by Rigaku Corporation), the X-ray structure analysis of 4-phenyl pyrene (2a), 4-(2,4,6-trimethylphenyl)pyrene (2h), and tribenzo[a,c,f]tetraphene (8) was performed. Table 4 shows the results. FIGS. 2 to 4 show the structures according to the Oak Ridge Thermal Ellipsoid Plot (ORTEP) program.

TABLE 4

|  | 2a | 2h | 8 |
|---|---|---|---|
| formula | C$_{22}$H$_{14}$ | C$_{25}$H$_{20}$ | C$_{30}$H$_{18}$ |
| fw | 278.33 | 320.41 | 378.44 |
| T (K) | 103(2) | 103(2) | 103(2) |
| λ (Å) | 0.7107 | 0.7107 | 0.7107 |
| cryst syst | Triclinic | Monoclinic | Triclinic |
| space group | P-1 | P2$_1$/c | P-1 |
| a, (Å) | 5.739(3) | 7.910(3) | 3.9020(15) |
| b, (Å) | 10.226(6) | 29.258(11) | 12.153(5) |
| c, (Å) | 12.543(7) | 8.208(3) | 19.400(8) |
| α, (deg) | 82.33(2) | 90 | 85.547(12) |
| β, (deg) | 77.27(2) | 111.797(6) | 85.134(11) |
| γ, (deg) | 75.35(2) | 90 | 78.235(12) |
| V, (Å$^3$) | 692.2(6) | 1763.8(12) | 895.7(6) |
| Z | 2 | 4 | 2 |
| Dcalc, (g/cm$^3$) | 1.335 | 1.207 | 1.403 |
| μ (mm$^{-1}$) | 0.076 | 0.068 | 0.080 |
| F(000) | 292 | 680 | 396 |
| cryst size (mm) | 0.10 × 0.10 × 0.02 | 0.10 × 0.05 × 0.05 | 0.10 × 0.02 × 0.02 |
| 2 θ range, (deg) | 3.34-25.00 | 3.10-25.00 | 3.43-25.00 |
| reflns collected | 6990 | 11789 | 6035 |
| indep reflns/R$_{int}$ | 2425/0.0488 | 3082/0.0759 | 3107/0.0393 |
| params | 199 | 229 | 271 |
| GOF on F$^2$ | 1.072 | 1.050 | 1.061 |

TABLE 4-continued

|  | 2a | 2h | 8 |
|---|---|---|---|
| R$_1$, wR$_2$ [1 > 2 σ (l)] | 0.0599, 0.1337 | 0.0664, 0.1331 | 0.0564, 0.1211 |
| R$_1$, wR$_2$ (all data) | 0.0935, 0.1552 | 0.1193, 0.1555 | 0.0954, 0.1419 |

Examples 35 and 36

In Examples 35 and 36, a regioselectively arylated aromatic compound was obtained by the reaction of the formula below.

[Chem. 184]

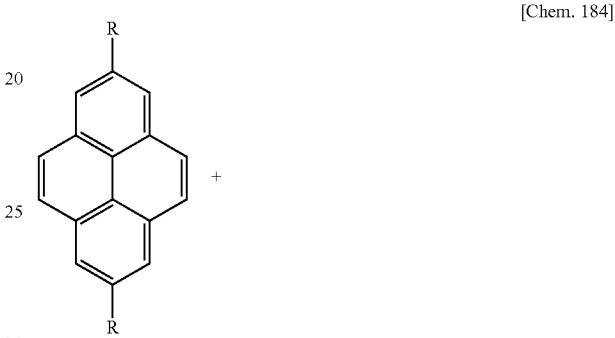

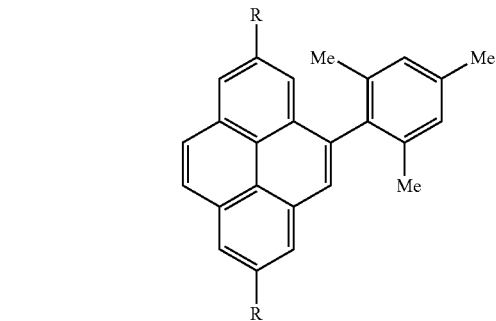

The details are described below.

Example 35

A Pd(OAc)$_2$ solution (4.4 mg, 20 mmol, 10 mol %), AgOTf (Tf indicates a trifluoromethylsulfonyl group) (10 mg, 40 μmol, 20 mol %), o-chloranil (49 mg, 0.20 mmol, 1.0 equivalent), and pyrene (40 mg, 0.20 mmol, 1.0 equivalent) represented by the formula below:

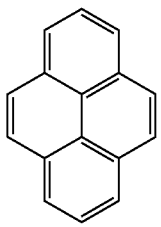

were introduced into mesitylene (1.0 mL, 36 equivalents) represented by the formula below:

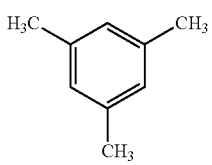

and the mixture was stirred for 14 hours at 50° C. The reaction product was filtered using a silica gel (eluent: CH$_2$Cl$_2$, 50 mL), and the volatile substance was removed under reduced pressure. The residue was purified by PTLC (hexane/CH$_2$Cl$_2$=10:1). As a result, 28 mg of 4-(2,4,6-trimethylphenyl)pyrene (2h) represented by the formula below:

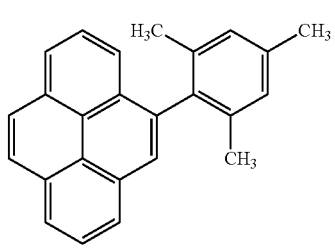

was obtained at a yield of 44%.

Example 36

Example 36 was prepared in the same manner as Example 35, except that a compound represented by the formula below:

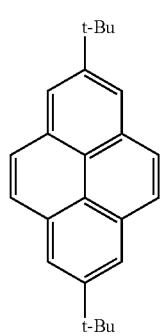

(t-Bu is a t-butyl group.)

was used in place of pyrene. As a result, 49 mg of 2,7-di-tert-butyl 4-(2,4,6-trimethylphenyl)pyrene (3h) represented by the formula below:

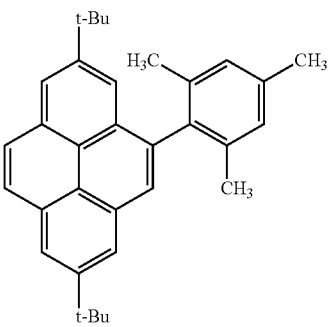

was obtained at a yield of 57%.

Examples 37 to 46

In Examples 37 to 46, a regioselectively arylated aromatic compound (arylated fluoranthene) was obtained by the reaction (C—H/C—B coupling) of the formula below.

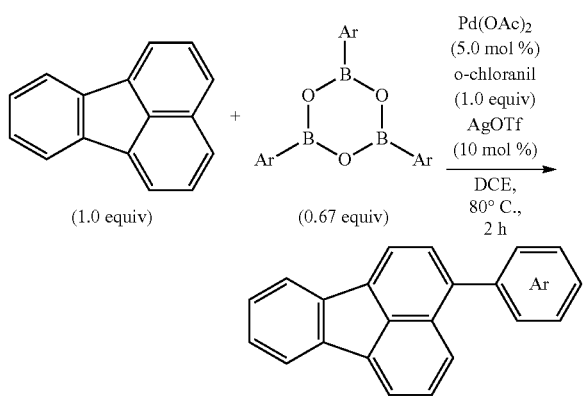

The details are described below.

Example 37

A Pd(OAc)$_2$ solution (2.2 mg, 10 µmol, 5.0 mol %), o-chloranil (49 mg, 0.20 mol, 1.0 equivalent), AgOTf (Tf indicates a trifluoromethylsulfonyl group) (5.2 mg, 20 μmol, 10 mol %), fluoranthene (40 mg, 0.20 mmol, 1.0 equivalent) represented by the formula below:

[Chem. 191]

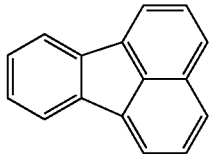

and a boron compound (0.13 mmol, 0.67 equivalents) represented by the formula below:

[Chem. 192]

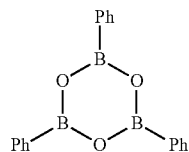

(Ph indicates a phenyl group.)

were introduced into dry 1,2-dichloroethane (1,2-DCE, 1.0 mL), and the mixture was stirred for 2 hours at 80° C. After cooling to room temperature, the reaction product was filtered using a silica gel (eluent: CH$_2$Cl$_2$, 50 mL). The regioselectivity was determined by the GC analysis of the filtrate using n-dodecane as an inner standard. The volatile substance was removed under reduced pressure, and the residue was purified by PTLC (main eluent: hexane). As a result, 27.6 mg of 3-phenylfluoranthene represented by the formula below:

[Chem. 193]

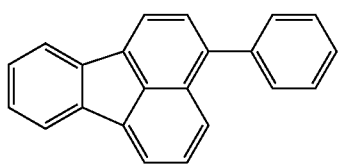

was obtained at a yield of 50% and a selectivity of 88%.

$^1$H NMR (600 MHz, CDCl$_3$) δ 7.97 (d, J=6.6 Hz, 1H), 7.94 (d, J=6.6 Hz, 1H), 7.93-7.91 (m, 3H), 7.62-7.59 (m, 4H), 7.52 (t, J=7.8 Hz, 2H), 7.44 (t, J=7.2 Hz, 1H), 7.39-7.38 (m, 2H); $^{13}$C NMR (100 MHz, CDCl$_3$) δ 140.3, 139.8, 139.1, 137.1, 136.3, 132.7, 130.3, 128.6, 128.4, 128.1, 127.6, 127.5, 127.4, 125.6, 121.5, 121.4, 120.0. HRMS (DART, ESI+) m/z calcd for C$_{22}$H$_{15}$ [M+H]$^+$: 279.1174, found: 279.1208. Mp: 139.3-141.0° C.

Example 38

Example 38 was prepared in the same manner as Example 37, except that a compound represented by the formula below:

[Chem. 194]

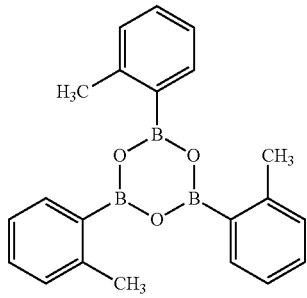

was used as a boron compound. Thus, 28.6 mg of 3-(o-toluoyl)fluoranthene represented by the formula below:

[Chem. 195]

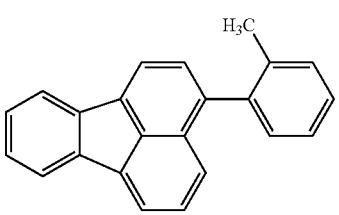

was obtained at a yield of 49% and a selectivity of 98%.

$^1$H NMR (CDCl$_3$, 600 MHz) δ 7.95 (d, J=6.6 Hz, 1H), 7.92-7.90 (m, 3H), 7.53 (dd, J=8.4, 7.2 Hz, 1H), 7.47 (d, J=8.4 Hz, 1H), 7.46 (d, J=6.6 Hz, 1H), 7.38-7.30 (m, 6H), 2.12 (s, 3H); $^{13}$C NMR (CDCl$_3$, 100 MHz) δ 140.0, 139.6, 139.3, 139.2, 137.1, 136.7, 136.2, 132.4, 130.7, 130.0, 129.1, 128.6, 128.0, 127.7, 127.6, 127.4, 125.7, 125.4, 121.5, 121.4, 120.0, 119.8, 20.5. HRMS (DART, ESI+) m/z calcd for C$_{23}$H$_{17}$ [M+H]$^+$: 293.1330, found: 293.1326, Mp: 50.5-51.5° C.

Example 39

Example 39 was prepared in the same manner as Example 37, except that a compound represented by the formula below:

[Chem. 196]

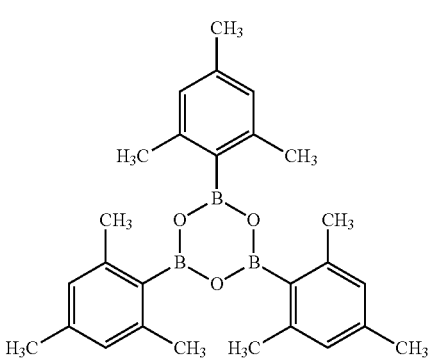

was used as a boron compound. Thus, 58.4 mg of 3-mesityl fluoranthene represented by the formula below:

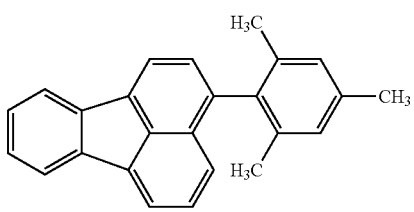

[Chem. 197]

was obtained at a yield of 71% and a selectivity of 99% or more.

$^1$H NMR (400 MHz, CDCl$_3$) δ 7.98 (d, J=7.2 Hz, 1H), 7.93-7.91 (m, 3H), 7.50 (dd, J=8.4, 6.8 Hz, 1H), 7.39-7.37 (m, 3H), 7.34 (d, J=8.4 Hz 1H), 7.02 (s, 2H), 2.40 (s, 3H), 1.93 (s, 6H); $^{13}$C NMR (100 MHz, CDCl$_3$) δ 139.5, 139.4, 139.3, 137.2, 136.99, 136.95, 135.9, 135.8, 132.7, 129.2, 128.5, 127.99, 127.95, 127.6, 127.4, 125.2, 121.5, 121.4, 120.2, 120.0, 21.1, 20.6. HRMS (DART, ESI+) m/z calcd for C$_{25}$H$_{21}$ [M+H]$^+$: 321.1643, found: 321.1649. Mp: 135.5-136.5° C.

Example 40

Example 40 was prepared in the same manner as Example 37, except that a compound represented by the formula below:

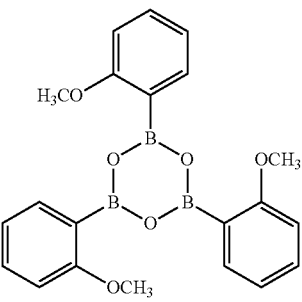

[Chem. 198]

was used as a boron compound, and an eluent for PTLC was changed to hexane/ethyl acetate-19:1. Thus, 26.1 mg of 3-(2-methoxyphenyl)fluoranthene represented by the formula below:

[Chem. 199]

was obtained at a yield of 42% and a selectivity of 97%.

$^1$H NMR (600 MHz, CDCl$_3$) δ 7.96 (d, J=7.2 Hz 1H), 7.90-7.88 (m, 3H), 7.61 (d, J=8.4 Hz 1H), 7.57 (d, J=7.2 Hz, 1H), 7.53 (dd, J=8.4, 6.6 Hz, 1H), 7.42 (t, J=7.8 Hz, 1H), 7.37-7.34 (m, 3H), 7.09 (t, J=7.8 Hz, 1H), 7.06 (d, J=7.8 Hz, 1H), 3.71 (s, 3H); $^{13}$C NMR (100 MHz, CDCl$_3$) δ 157.1, 139.6, 139.3, 137.0, 136.9, 136.3, 132.5, 132.3, 129.3, 129.2, 129.1, 128.5, 127.6, 127.4, 127.3, 126.1, 121.41, 121.35, 120.5, 119.9, 119.8, 111.1, 55.5. HRMS (DART, ESI+) m/z calcd for C$_{23}$H$_{17}$O [M+H]$^+$: 309.1279, found: 309.1266. Mp: 113.9-115.9° C.

Example 41

Example 41 was prepared as Example 37, except that a compound represented by the formula below:

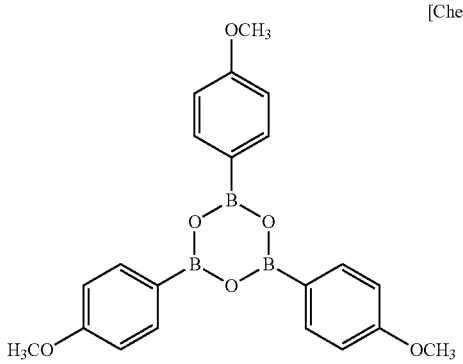

[Chem. 200]

was used as a boron compound, and an eluent for PTLC was changed to hexane/ethyl acetate-19:1. Thus, 24.6 mg of 3-(4-methoxyphenyl)fluoranthene represented by the formula below:

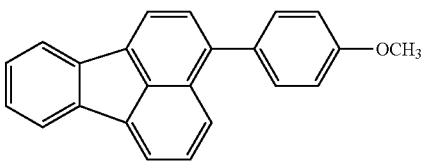

[Chem. 201]

was obtained at a yield of 40% and a selectivity of 78%.

$^1$H NMR (CDCl$_3$, 600 MHz) δ 7.96-7.90 (m, 5 H), 7.61 (dd, J=8.4, 7.2 Hz, 1H), 7.57 (d, J=7.2 Hz, 1H), 7.53 (d, J=8.4 Hz, 2H), 7.39-7.34 (m, 2H), 7.05 (d, J=8.4 Hz, 2H), 3.89 (s, 3H); $^{13}$C NMR (CDCl$_3$, 100 MHz) δ 159.1, 140.0, 139.5, 139.1, 137.1, 135.9, 132.7, 132.2, 131.3, 128.5, 128.4, 127.9, 127.5, 127.3, 125.7, 121.5, 121.3, 120.1, 119.9, 113.9, 55.4. HRMS (DART, ESI+) m/z calcd for C$_{23}$H$_{17}$O [M+H]$^+$: 309.1279, found: 309.1230. Mp: 161.8-168.3° C.

Example 42

Example 42 was prepared in the same manner as Example 37, except that a compound represented by the formula below:

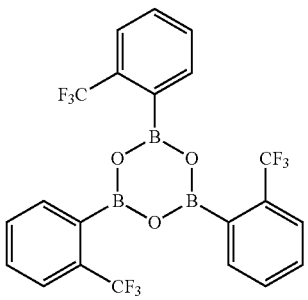

was used as a boron compound. Thus, 39.3 mg of 3-[2-(trifluoromethyl)phenyl]fluoranthene represented by the formula below:

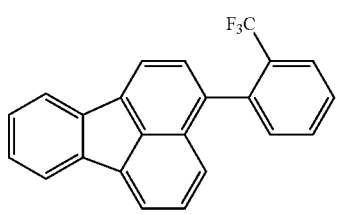

was obtained at a yield of 57% and a selectivity of 99%.

$^1$H NMR (CDCl$_3$, 600 MHz) δ 7.92 (d, J=6.6 Hz, 1H), 7.91-7.88 (m, 3H), 7.83 (d, J=7.8 Hz, 1H), 7.58 (d, J=7.2 Hz, 1H), 7.55-7.49 (m, 3H), 7.41 (d, J=7.2 Hz, 1H), 7.37-7.36 (m, 2H), 7.34 (d, J=8.4 Hz, 1H); $^{13}$C NMR (CDCl$_3$, 100 MHz) δ 139.6, 139.2, 138.34, 138.32, 136.9, 136.9, 132.9, 132.2, 130.8, 129.8 (q, $^2J_{FC}$=30.3 Hz), 129.5, 128.9, 128.8, 128.1, 127.8, 127.7, 127.67, 127.66, 126.1 (q, $^3J_{FC}$=5.1 Hz), 125.3, 124.0 (q, $^1J_{FC}$=275.4 Hz), 121.6, 120.1, 119.2. HRMS (DART, ESI+) m/z calcd for C$_{23}$H$_{14}$F$_3$ [M+H]$^+$: 347.1048, found: 347.1004. Mp: 61.8-63.8° C.

Example 43

Example 43 was prepared in the same manner as Example 37, except that a compound represented by the formula below:

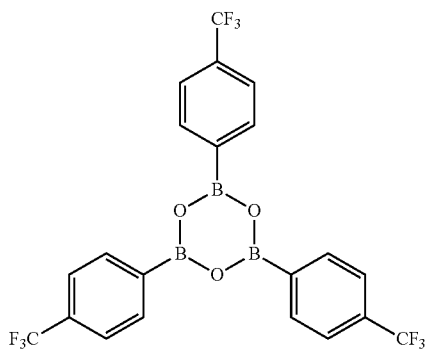

was used as a boron compound. Thus, 29.5 mg of 3-[4-(trifluoromethyl)phenyl]fluoranthene represented by the formula below:

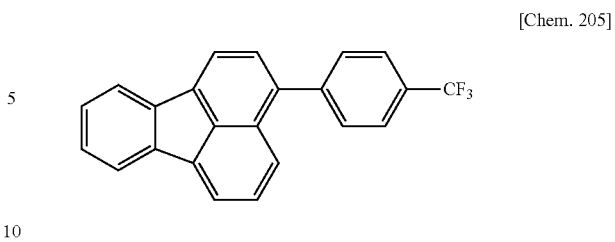

was obtained at a yield of 43% and a selectivity of 86%.

$^1$H NMR (CDCl$_3$, 600 MHz) δ 7.98 (d, J=7.2 Hz, 1H), 7.96 (d, J=6.6 Hz, 1H), 7.93-7.91, (m, 2H), 7.83 (d, J=8.4 Hz, 1H), 7.78 (d, J=7.8 Hz, 2H), 7.71 (d, J=7.8 Hz, 2H), 7.62 (dd, J=8.4, 7.2 Hz, 1H), 7.59 (d, J=7.2 Hz, 1H), 7.41-7.39 (m, 2H); $^{13}$C NMR (CDCl$_3$, 100 MHz) δ 143.5, 139.6, 138.9, 137.3, 137.1, 132.7, 130.5, 129.5 (q, $^2J_{FC}$=33.0 Hz), 128.9, 128.5, 128.1, 127.79, 127.75, 125.3 (q, $^3J_{FC}$=4.0 Hz), 124.3 (q, $^1J_{FC}$=273 Hz), 121.6, 120.3. 119.9. HRMS (DART, ESI+) m/z calcd for C$_{23}$H$_{14}$F$_3$[M+H]$^+$: 347.1048, found: 347.1003. Mp: 194.0-195.7° C.

Example 44

Example 44 was prepared in the same manner as Example 37, except that a compound represented by the formula below:

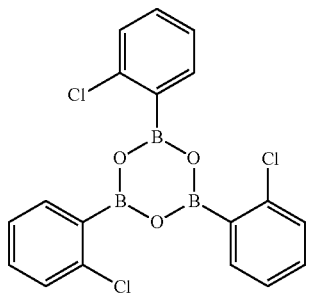

was used as a boron compound. Thus, 23.6 mg of 3-(2-chlorophenyl)fluoranthene represented by the formula below:

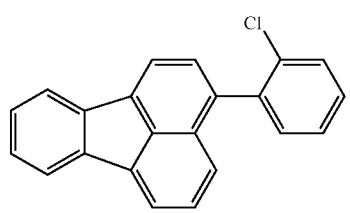

was obtained at a yield of 38% and a selectivity of 94%.

$^1$H NMR (CDCl$_3$, 600 MHz) δ 7.96 (d, J=7.2 Hz, 1H), 7.92-7.90 (m, 3H), 7.57-7.51 (m, 4H), 7.43-7.42 (m, 1H), 7.40-7.36 (m, 4H); $^{13}$C NMR (CDCl$_3$, 100 MHz) δ 139.7, 139.2, 138.3, 137.2, 137.1, 137.0, 133.9, 132.4, 132.4, 129.7, 129.2, 129.0, 128.8, 128.1, 127.6, 126.5, 125.5, 121.5, 120.1, 119.6. HRMS (DART, ESI+) m/z calcd for C$_{22}$H$_{14}$Cl [M+H]$^+$: 313.0784, found: 313.0787. Mp: 95.7-97.4° C.

Example 45

Example 45 was prepared in the same manner as Example 37, except that a compound represented by the formula below:

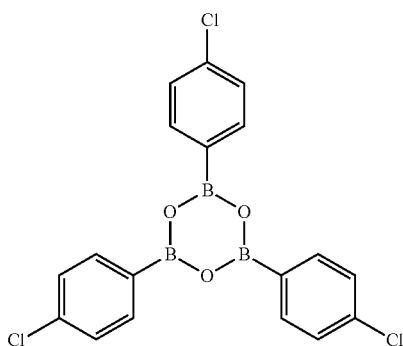

[Chem. 208]

was used as a boron compound. Thus, 29.2 mg of 3-(4-chlorophenyl)fluoranthene represented by the formula below:

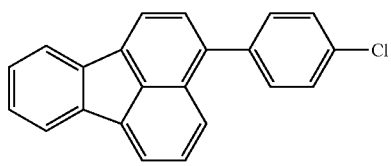

[Chem. 209]

was obtained at a yield of 47% and a selectivity of 88%.

$^1$H NMR (600 MHz, CDCl$_3$) δ 7.96 (d, J=7.8 Hz, 1H), 7.95 (d, J=6.0 Hz, 1H), 7.92-7.91 (m, 2H), 7.85 (d, J=9.0 Hz, 1H), 7.61 (dd, J=8.4, 7.8 Hz, 1H), 7.56 (d, J=7.2 Hz, 1H), 7.52 (d, J=8.1 Hz, 2H), 7.49 (d, J=7.8 Hz, 2H), 7.40-7.38 (m, 2H); $^{13}$C NMR (100 MHz, CDCl$_3$) δ 139.5, 139.0, 138.9, 138.2, 137.2, 136.7, 133.6, 131.5, 128.60, 128.58, 128.3, 128.2, 127.7 127.6, 125.2, 121.54, 121.49, 120.1, 119.9. HRMS (DART, ESI+) m/z calcd for C$_{22}$H$_{14}$Cl [M+H]$^+$: 313.0784, found: 313.0752. Mp: 173.8-175.8° C.

Example 46

Example 46 was prepared in the same manner as Example 37, except that a compound represented by the formula below:

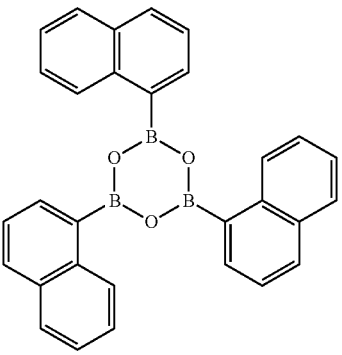

[Chem. 210]

was used as a boron compound. Thus, 13.1 mg of 3-(naphthalen-1-yl)fluoranthene represented by the formula below:

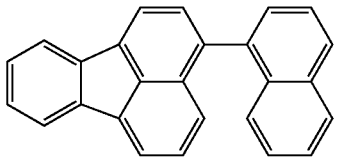

[Chem. 211]

was obtained at a yield of 20% and a selectivity of 92%.

$^1$H NMR (CDCl$_3$, 600 MHz) δ 8.04 (d, J=6.6 Hz, 1H), 7.97-7.93 (m, 5H), 7.66 (d, J=6.6 Hz, 1H), 7.62-7.59 (m, 2H), 7.56 (d, J=7.2 Hz, 1H), 7.50-7.46 (m, 2H), 7.43-7.40 (m, 3H), 7.32 (d, J=7.2 Hz, 2H), 7.31-7.29 (m, 1H); $^{13}$C NMR (CDCl$_3$, 100 MHz) δ 139.6, 139.2, 138.6, 137.4, 137.0, 136.6, 133.5, 132.9, 132.5, 129.9, 129.7, 128.3, 128.1, 128.04, 128.00, 127.62, 127.56, 126.6, 126.0, 125.9, 125.8, 125.2, 121.6, 121.5, 120.1, 119.8. HRMS (DART, ESI+) m/z calcd for C$_{26}$H$_{17}$ [M+H]$^+$: 329.1330, found: 329.1294. Mp: 187.9-189.5° C.

Examples 47 to 49

In Examples 47 to 49, experiments were conducted in which the kinds of the boron compound and the silver compound of Example 37 were changed. The details are explained below.

Example 47

Example 47 was prepared in the same manner as Example 37, except that phenylboronic acid represented by the formula below:

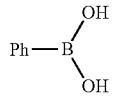

[Chem. 212]

(Ph indicates a phenyl group.)

was used as a boron compound, and a silver compound was not used. Thus, 3-phenylfluoranthene was obtained at a yield of 28% and a selectivity of 92%.

Example 48

Example 48 was prepared in the same manner as Example 37, except that phenylboronic acid represented by the formula below:

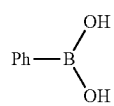

[Chem. 213]

(Ph indicates a phenyl group.)

was used as a boron compound. Thus, 3-phenylfluoranthene was obtained at a yield of 36% and a selectivity of 92%.

Example 49

Example 49 was prepared in the same manner as Example 37, except that a compound represented by the formula below:

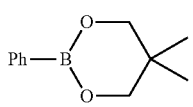

[Chem. 214]

(Ph indicates a phenyl group.)

was used as a boron compound. Thus, 3-phenylfluoranthene was obtained at a yield of 50% and a selectivity of 90%.

Example 50

In Example 50, a regioselectively arylated (mesitylated) aromatic compound (mesitylated fluoranthene) represented by the reaction (CH/CH coupling) of the formula below:

[Chem. 215]

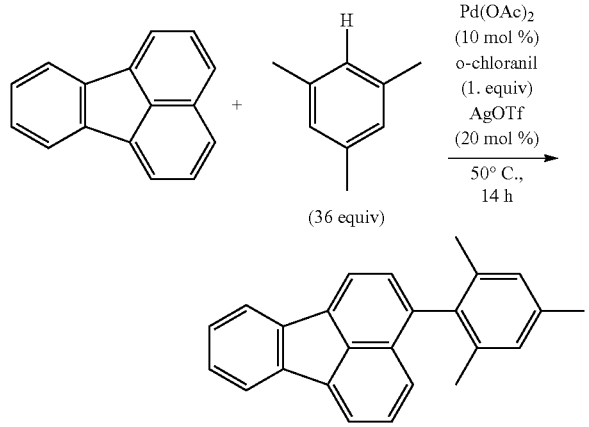

was obtained. The details are described below.

A Pd(OAc)$_2$ solution (2.2 mg, 10 µmol, 5.0 mol %), o-chloranil (49 mg, 0.20 mmol, 1.0 equivalent), AgOTf (Tf indicates a trifluoromethylsulfonyl group) (5.2 mg, 20 µmol, 10 mol %), and fluoranthene (40 mg, 0.20 mmol, 1.0 equivalent) represented by the formula below:

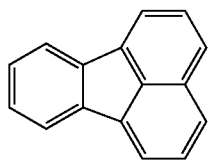

[Chem. 216]

were introduced into mesitylene (1.0 mL, 7.2 mmol, 36 equivalents) represented by the formula below:

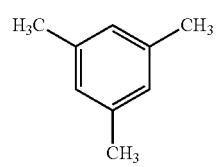

[Chem. 217]

and the mixture was stirred for 14 hours at 50° C. After cooling to room temperature, the reaction product was filtered using a silica gel (eluent: CH$_2$Cl$_2$, 50 mL), and the volatile substance was removed under reduced pressure. The residue was purified by PTLC (eluent: hexane). As a result, 47.7 mg of 3-mesityl fluoranthene represented by the formula below:

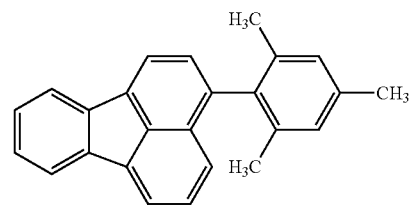

[Chem. 218]

was obtained at a yield of 74%.

Example 51

In Example 51, a regioselectively arylated (naphthylated) aromatic compound (naphthylated fluoranthene) represented by the reaction (CH/CH coupling) of the formula below:

[Chem. 219]

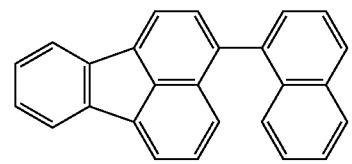

was obtained. The details are described below.

A Pd(OAc)$_2$ solution (2.2 mg, 10 μmol, 5.0 mol %), o-chloranil (25 mg, 0.10 mmol, 1.0 equivalent), AgOTf (Tf indicates a trifluoromethylsulfonyl group) (5.2 mg, 20 μmol, 10 mol %), fluoranthene (20 mg, 0.10 mmol, 1.0 equivalent) represented by the formula below:

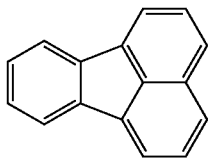
[Chem. 220]

and naphthalene (256 mg, 2.0 mmol, 20 equivalents) were introduced into dry 1,2-dichloroethane (1,2-DCE, 200 μL), and the mixture was stirred for 12 hours at 80° C. After cooling to room temperature, the reaction product was filtered using a silica gel (eluent: CH$_2$Cl$_2$, 50 mL), and the volatile substance was removed under reduced pressure. The residue was purified by PTLC (eluent: hexane). As a result, 3.3 mg of 3-(naphthalen-1-yl)fluoranthene represented by the formula below:

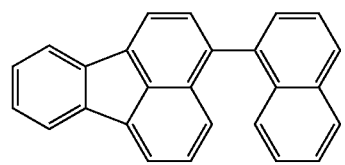
[Chem. 221]

was obtained at a yield of 10%.

Example 52

In Example 52, the conjugated system was extended by the reaction (condensation reaction) of the formula below.

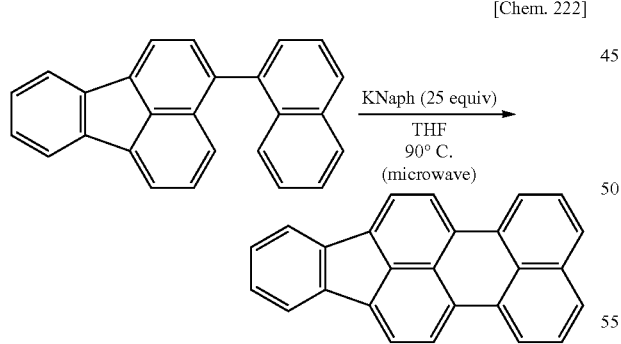
[Chem. 222]

The details are described below.

The mixture of potassium (100 mg, 2.56 mmol) and naphthalene (162 mg, 1.26 mmol) were stirred in dry THF (5 mL) for 1 hour, and the THF solution of potassium naphthalenide was obtained. A glass microwave synthesis reaction container (10 mL) with a stirring bar was flame-dried under vacuum. After cooling to room temperature, argon was loaded. 3-(Naphthalen-1-yl)fluoranthene (16.4 mg, 0.05 mmol) obtained in Example 46 or 51 and the THF solution of potassium naphthalenide (5 mL) obtained above were added to the reaction container. The reaction container was sealed and heated for 1 hour at 90° C. under stirring. After cooling to room temperature, oxygen was bubbled for 30 minutes, and the reaction product was filtered using a silica gel (CH$_2$Cl$_2$). The residue was purified by PTLC (hexane). As a result, 2.7 mg of a compound represented by the formula below:

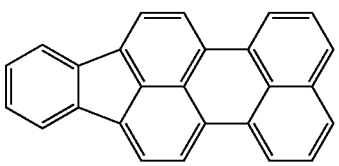
[Chem. 223]

was obtained at a yield of 17% as an orange solid.

$^1$H NMR (C$_2$D$_{2c}$l$_4$. 600 MHz, 80° C.) 68.41 (d, J=7.4 Hz, 2H), 8.35 (d, J=7.4 Hz, 2H), 8.04 (d, J=7.6 Hz, 2H), 7.98 (dd, J=5.5, 3.1 Hz, 2H), 7.84 (d, J=8.1 Hz, 2H), 7.61 (t, J=7.6 Hz, 2H), 7.44 (dd, J=5.6, 3.0 Hz, 2H); $^{13}$C NMR (C$_2$D$_{2c}$l$_4$, 150 MHz, 80° C.) 6138.8, 135.4, 134.6, 132.8, 131.4, 130.1, 129.1, 127.8, 127.2, 126.5, 125.3, 121.54, 121.50, 121.2, 120.6. HRMS (DART, ESI+) m/z calcd for C$_{21}$H$_{15}$ [M+H]$^+$: 327.1173, found: 327.1173. Mp: >300° C.

Reference Example 2

Figure 5:
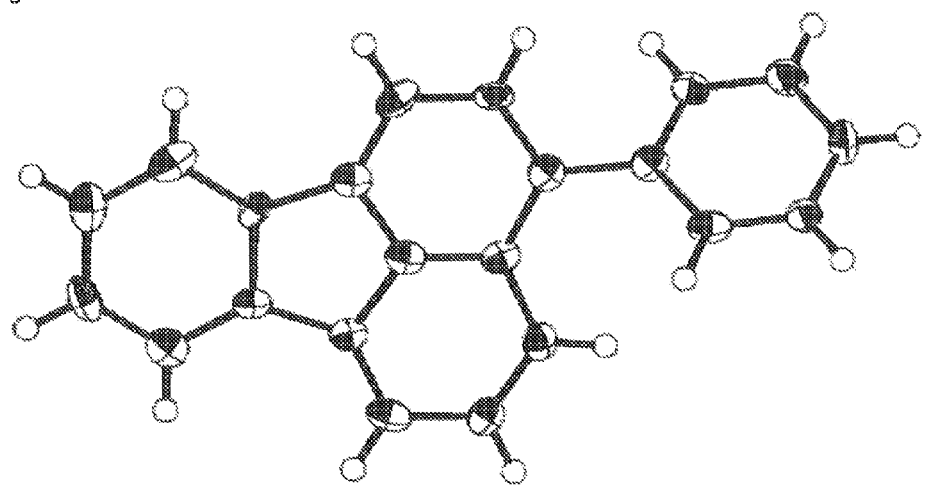
FIG. 5 is a drawing showing a structure of 3-phenylfluoranthene, produced using the Oak Ridge Thermal Ellipsoid Plot (ORTEP) program (50% probability ellipsoids).
Figure 6:
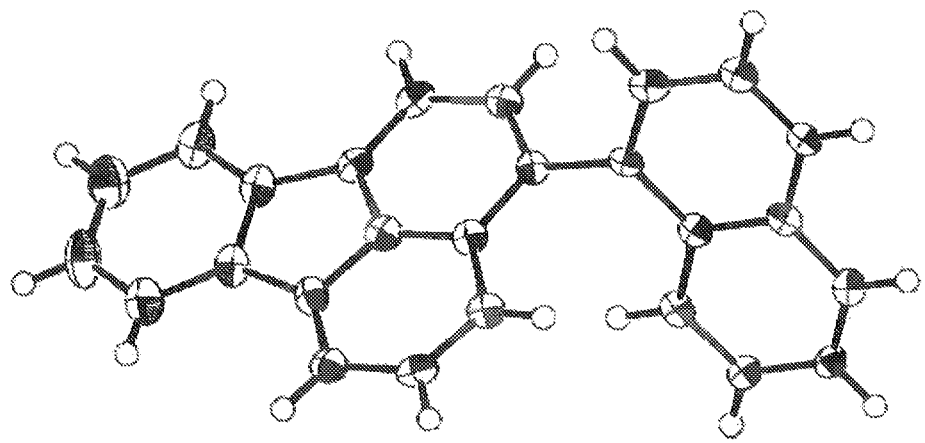
FIG. 6 is a drawing showing a structure of 3-(naphthalene-1-yl)fluoranthene, produced using the Oak Ridge Thermal Ellipsoid Plot (ORTEP) program (50% probability ellipsoids).

X-Ray Structure Analysis of 3-phenylfluoranthene and 3-(naphthalen-1-yl)fluoranthene Table 5 shows the crystal data and strength data of 3-phenylfluoranthene and 3-(naphthalen-1-yl)fluoranthene. Each data was obtained using "Saturn" (trade name, a CCD single-crystal automatic X-ray structure analysis device produced by Rigaku Corporation). FIGS. 5 and 6 show the structures according to the Oak Ridge Thermal Ellipsoid Plot (ORTEP) program.

TABLE 5

| | 3-Phenylfluoranthene | 3-(Naphthalen-1-yl)fluoranthene |
|---|---|---|
| formula | C$_{22}$H$_{14}$ | C$_{26}$H$_{16}$ |
| fw | 278.33 | 328.39 |
| T (K) | 103(2) | 103(2) |
| λ (Å) | 0.7107 | 0.7107 |
| cryst syst | Orthorhombic | Monoclinic |
| space group | P2$_1$2$_1$2$_1$ | P2$_1$/a |
| a, (Å) | 7.521(2) | 9.587(4) |
| b, (Å) | 16.456(5) | 6.368(2) |
| c, (Å) | 23.063(7) | 27.417(11) |
| α, (deg) | 90 | 90 |
| β, (deg) | 90 | 96.254(6) |
| γ, (deg) | 90 | 90 |
| V, (Å$^3$) | 2854.6(14) | 1663.7(11) |
| Z | 8 | 4 |
| Dcalc, (g/cm$^3$) | 1.295 | 1.311 |
| μ (mm$^{-1}$) | 0.073 | 0.074 |
| F(000) | 1168 | 688 |
| cryst size (mm) | 020 × 0.05 × 0.01 | 0.10 × 0.05 × 0.01 |
| 2 θ range, (deg) | 3.04-25.00 | 3.29-25.00 |
| reflns collected | 19297 | 10557 |
| indep reflns/R$_{int}$ | 5005/0.1296 | 2926/0.0983 |
| params | 397 | 235 |
| GOF on F$^2$ | 1.074 | 1.040 |
| R$_1$, wR$_2$ [I > 2 σ (I)] | 0.0974, 0.2133 | 0.0909, 0.2140 |
| R$_1$, wR$_2$ (all data) | 0.1377, 0.2403 | 0.1623, 0.2694 |

Reference Example 3

Optical Properties of fluoranthene, 3-phenylfluoranthene, and 3-(naphthalen-1-yl)fluoranthene Fluoranthene, 3-phenylfluoranthene and 3-(naphthalen-1-yl)fluoranthene were the targets for the measurement of optical properties.

A target solid sample (amorphous) was weighted out to 3 significant figures, and a diluted solution by chloroform was prepared using a 50 mL measuring flask.

The optical properties (fluorescence spectrum) of the diluted solution was measured under the following conditions (device and apparatus used).
Ultra-violet and visible spectrophotometer: "UV-3600" produced by Shimadzu Corporation.
Spectrofluorophotometer: "F-4500" produced by Hitachi Ltd.
1 cm Quartz cell The excitation wavelength used for measuring fluorescence spectrum was the longest maximum absorption wavelength.

Figure 7:
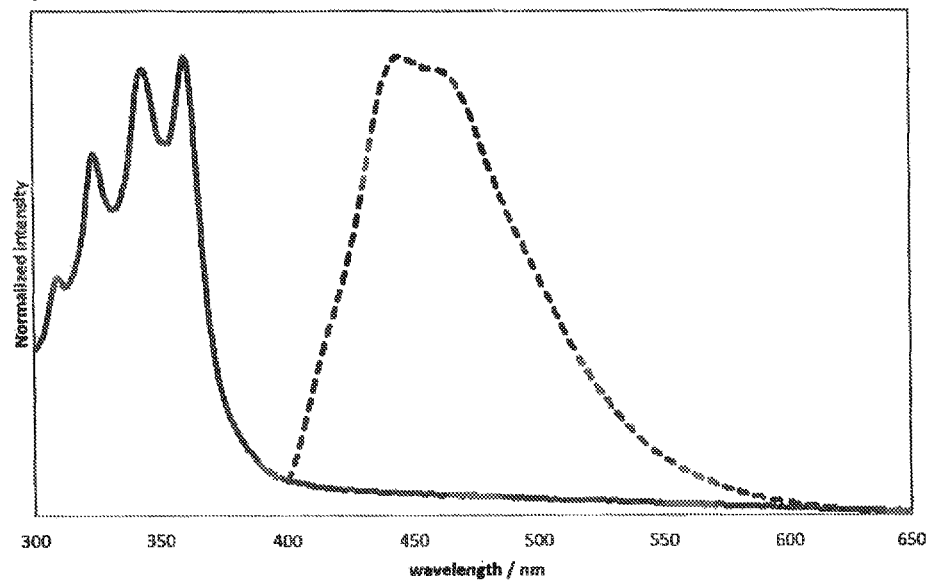
FIG. 7 shows the results of measuring the optical properties of fluoranthene. The solid line represents the absorption spectrum, and the dashed line represents the fluorescence spectrum.
Figure 8:
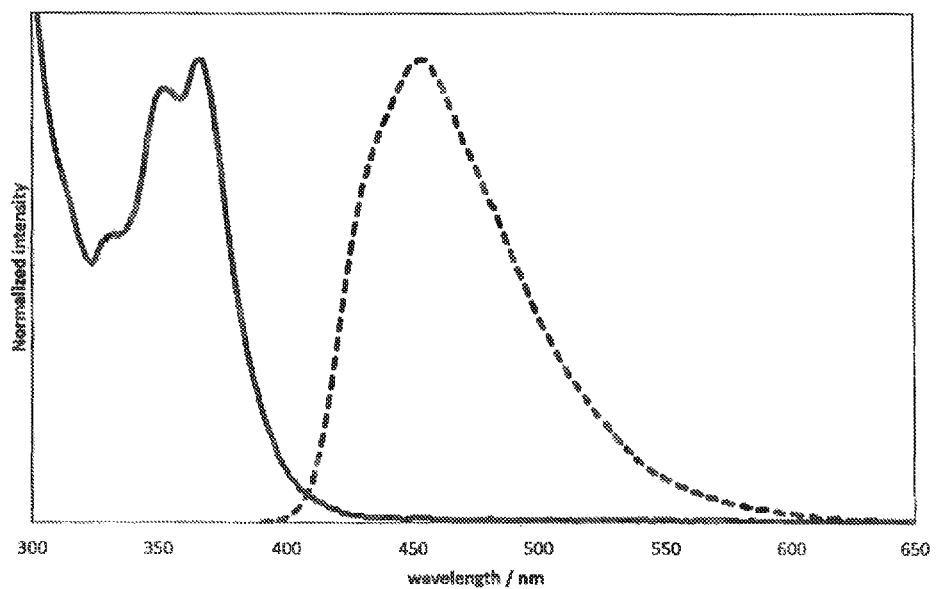
FIG. 8 shows the results of measuring the optical properties of 3-phenylfluoranthene. The solid line represents the absorption spectrum, and the dashed line represents the fluorescence spectrum.
Figure 9:
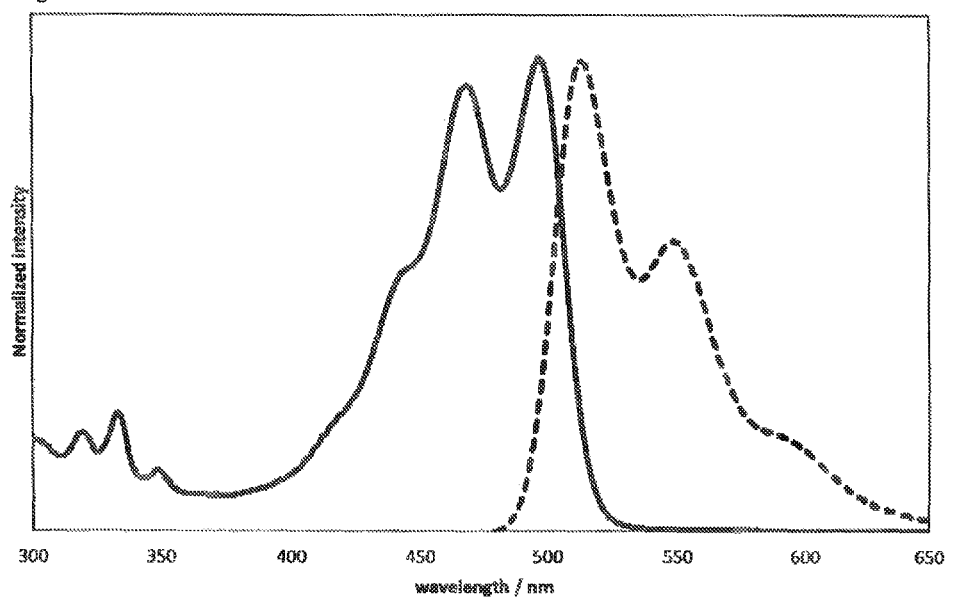
FIG. 9 shows the results of measuring the optical properties of 3-(naphthalene-1-yl)fluoranthene. The solid line represents the absorption spectrum, and the dashed line represents the fluorescence spectrum.

FIGS. 7 to 9 show the results. FIGS. 7, 8, and 9 respectively show the measurement results of fluoranthene, 3-phenylfluoranthene, and 3-(naphthalen-1-yl)fluoranthene. In each figure, the continuous line indicates an absorption spectrum, and the dashed line indicates an emission spectrum.

Example 53

Similar to Examples 37 to 52, perylene was used as a substrate in place of fluoranthene. By the reaction shown below,

[Chem. 224]

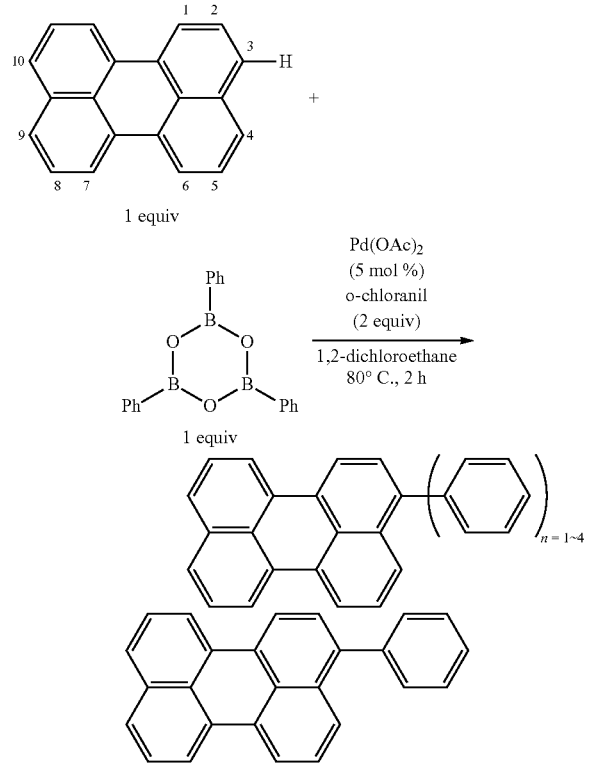

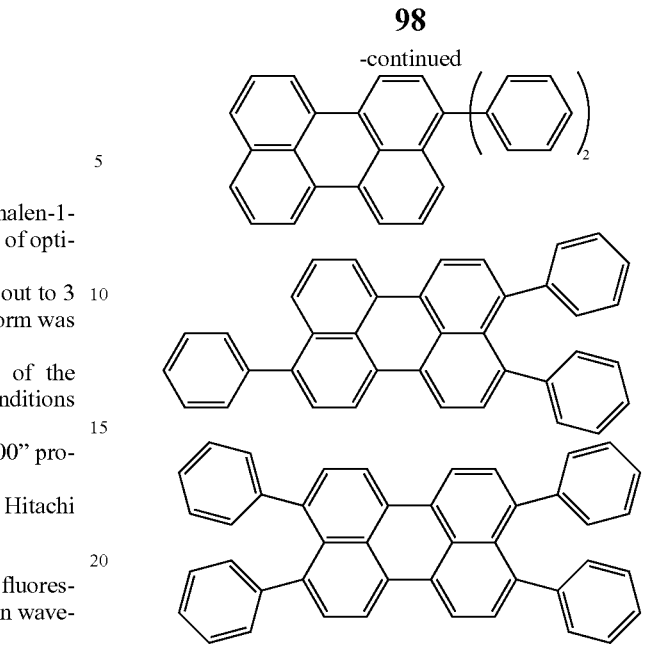

phenylperylene, di-phenylperylene, triphenylperylene, and tetraphenylperylene were obtained. The details are described below.

A Pd(OAc)$_2$ solution (11.2 mg, 50 µmol, 5.0 mol %), o-chloranil (490 mg, 2.0 mmol, 2.0 equivalents), perylene (252 mg, 1.0 mmol, 1.0 equivalent) represented by the formula below:

[Chem. 225]

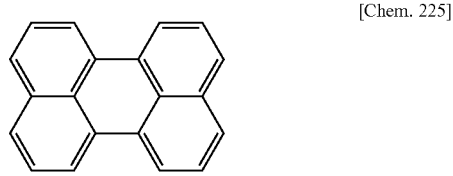 [SMILES: c1cc2cccc3c4cccc5cccc(c(c1)c23)c54]

and a boron compound (311 mg, 1.0 mmol, 1.0 equivalent) represented by the formula below:

[Chem. 226]

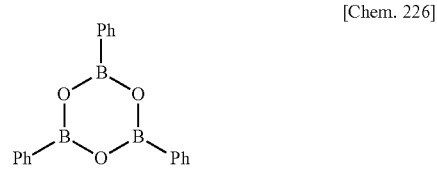

(Ph indicates a phenyl group.)

were introduced into dry 1,2-dichloroethane (1,2-DCE, 20 mL). The mixture was stirred for 2 hours at 80° C. After cooling to room temperature, the reaction product was filtered using a silica gel (eluent: CH$_2$Cl$_2$, 100 mL). After the filtrate was evaporated, the residue was purified by silica gel column chromatography (eluent: hexane/CH$_2$Cl$_2$=100/0 to 85/15) to obtain 56.2 mg of 3-phenylperylene at a yield of 17%, 97.5 mg of di-phenylperylene at a yield of 24%, 54.2 mg of 3,4,9-triphenylperylene at a yield of 11%, and 3.7 mg of tetraphenylperylene at a yield of 0.7%.

3,4,9-Triphenylperylene $^1$H NMR (600 MHz, CDCl$_3$/CS$_2$=1/1) δ 8.24 (d, J=7.8 Hz, 1H), 8.23 (d, J=7.8 Hz, 1H), 8.21 (d, J=7.8 Hz, 1H), 8.19 (d. J=7.8 Hz, 1H), 7.74 (d, J=7.8 Hz, 1H), 7.49-7.45 (m, 4H), 7.42-7.37 (m, 5H), 6.96 (d, J=7.2 Hz, 4H), 6.89 (t, J=7.2 Hz, 4H), 6.84 (d, J=7.2 Hz, 2H); $^{13}$C NMR (150 MHz, CDCl$_3$/CS$_2$=1/1) δ142.9, 140.4, 140.01, 139.98, 139.6, 132.5, 131.5, 131.3, 130.61, 130.59. 130.56, 130.5, 130.4, 129.8, 129.4, 128.4, 128.2, 127.8, 127.2, 126.6, 125.8, 125.7, 120.4, 120.3, 120.1, 120.0. HRMS (DART, ESI+) m/z calcd for C$_{38}$H$_{25}$ [M+H]$^+$: 481.1956, found: 481.1955.

3,4,9,10-Tetraphenylperylene $^1$H NMR (600 MHz, CDCl$_3$/CS$_2$=1/1) δ 8.32 (d, J=7.8 Hz 4H), 7.45 (d. J=7.8 Hz 4H), 7.02 (d, J=6.6 Hz, 8H), 6.93 (t, J=7.2 Hz, 8H), 6.89 (t, J=7.4 Hz, 4H); $^{13}$C NMR (150 MHz, CDCl$_3$/CS$_2$=1/1) δ142.8, 140.0, 131.7, 130.7, 130.4, 130.1, 129.4, 127.2, 125.7, 120.4. HRMS (DART, ESI+) m/z calcd for C$_{44}$H$_{29}$O [M+H]$^+$: 557.2269, found: 557.2243.

Figure 10:
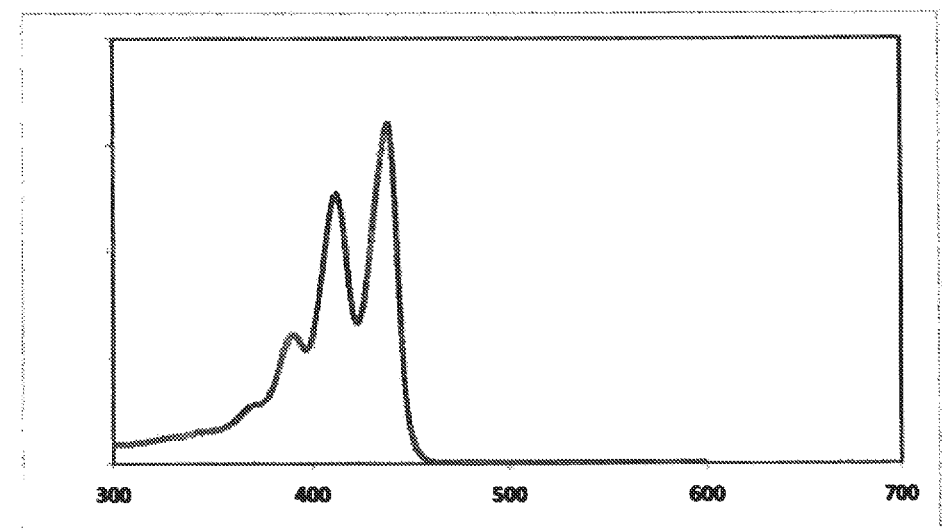
FIG. 10 shows the results of measuring the optical properties (absorption spectrum) of perylene.
Figure 11:
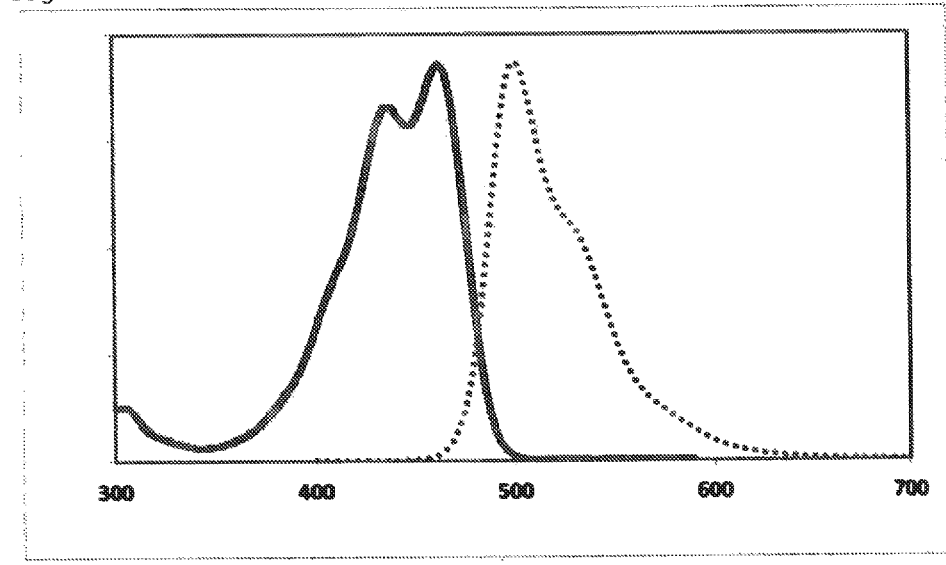
FIG. 11 shows the results of measuring the optical properties of 3,4,9-triphenyl perylene. The solid line represents the absorption spectrum, and the dashed line represents the fluorescence spectrum.
Figure 12:
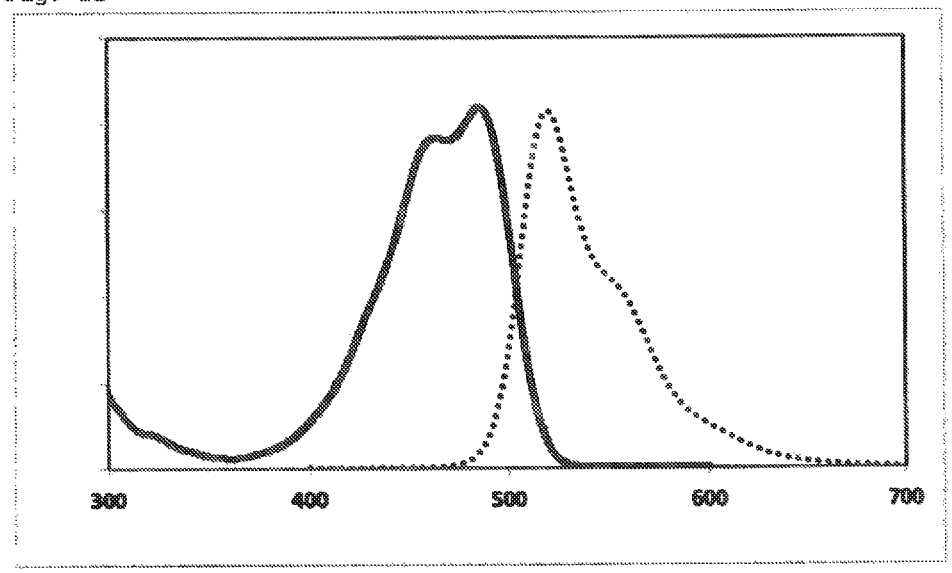
FIG. 12 shows the results of measuring the optical properties of 3,4,9,10-tetraphenyl perylene. The solid line represents the absorption spectrum, and the dashed line represents the fluorescence spectrum.

Similar to Reference Example 3, the optical properties of perylene, which was a starting material substrate, and the obtained 3,4,9-triphenylperylene and 3,4,9,10-tetraphenylperylene were measured. FIGS. 10 to 12 and Table 6 show the results.

TABLE 6

| | Absorption | | Fluorescence | | |
|---|---|---|---|---|---|
| | ε [M$^{-1}$cm$^{-1}$] | λ max [nm] | λ em [nm] | φ$_F$ | luminescent color |
| Perylene | 34000 | 438 | 448 | 0.89 | Blue |
| Triphenyl-perylene | 37000 | 473 | 500 | 0.93 | Green |
| Tetraphenyl-perylene | 42000 | 486 | 520 | 0.93 | Green |

The invention claimed is:

1. A method for producing a polycyclic aromatic compound substituted with at least one substituted or unsubstituted aryl group, the method comprising reacting a polycyclic aromatic compound with a substituted or unsubstituted aryl-containing boron compound in the presence of a palladium compound and o-chloranil.

2. The method according to claim 1, wherein the substituted or unsubstituted aryl-containing boron compound is an organic boron compound represented by Formula (A1):

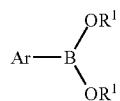

(A1)

wherein Ar is substituted or unsubstituted C$_{6-50}$ aryl; two R$^1$ may be the same or different, and each represents hydrogen or C$_{1-20}$ alkyl; or two R$^1$ may bond to each other to form a ring with the adjacent —O—B—O—, and the ring may further have an aromatic ring fused thereto; a cyclic organic boron compound represented by Formula (A2):

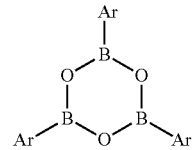

(A2)

wherein three Ar may be the same or different, and each is as defined above; or an ionic boron compound represented by Formula (A3):

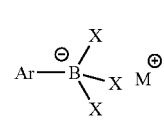

(A3)

wherein Ar is as defined above; three X may be the same or different, and each represents halogen or substituted or unsubstituted C$_{6-50}$ aryl, and M is an alkali metal.

3. The method according to claim 1, wherein the polycyclic aromatic compound substituted with at least one substituted or unsubstituted aryl group is a compound represented by Formula (D):

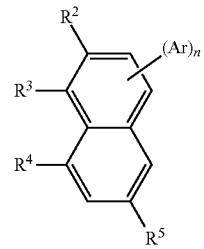

(D)

wherein R$^2$ to R$^5$ may be the same or different, and each represents hydrogen or C$_{1-20}$ alkyl, Ar represents substituted or unsubstituted C$_{6-50}$ aryl and may bond to any of the cyclic structures, n is an integer of 1 to 4, and one of the following requirements (1) to (4) is satisfied:

(1) R$^2$ to R$^5$ are each hydrogen;

(2) R$^2$ and R$^5$ are each hydrogen; R$^3$ and R$^4$ bond to each other to form a 5- or 6-membered unsaturated ring; and the unsaturated ring may further have a monocyclic or fused aromatic ring fused thereto;

(3) R$^2$ and R$^3$ bond to each other to form a substituted or unsubstituted aromatic ring; R$^4$ is hydrogen; and R$^5$ is hydrogen or C$_{1-20}$ alkyl;

(4) R$^2$ and R$^3$ bond to each other to form a substituted or unsubstituted aromatic ring; R$^3$ and R$^4$ bond to each other to form a substituted or unsubstituted aromatic ring; and R$^5$ is hydrogen or C$_{1-20}$ alkyl, and the polycyclic aromatic compound is a compound represented by Formula (B):

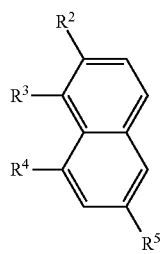

(B)

wherein $R^2$ to $R^5$ are as defined above.

4. The method according to claim 1, wherein the palladium compound comprises zerovalent or divalent palladium.

5. The method according to claim 1, wherein the reaction of the polycyclic aromatic compound with the substituted or unsubstituted aryl-containing boron compound is performed in the presence of a silver compound.

6. A method for producing a compound having a structure represented by Formula (C):

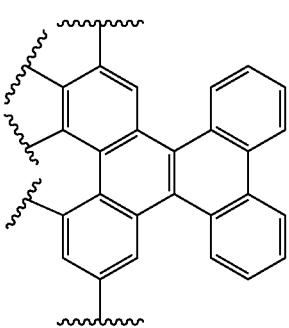

(C)

the method comprising the steps of:
(I) reacting a compound having a structure represented by Formula (B'):

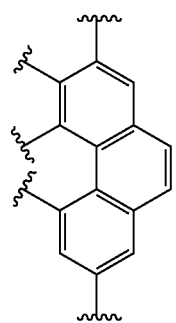

(B')

with a compound represented by Formula (G):

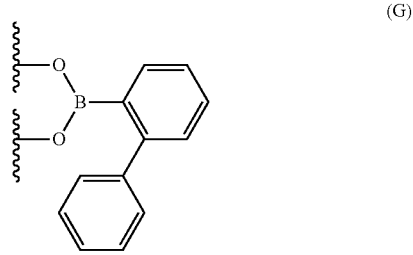 [SMILES: *OB(O*)c1ccccc1-c1ccccc1]

(G)

in the presence of a palladium compound and o-chloranil to produce a compound of Formula (D'):

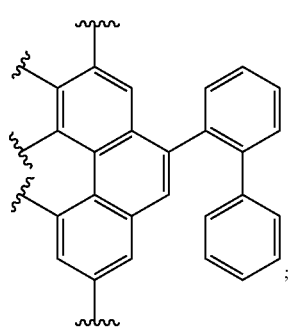

(D')

and
(II) subjecting the compound obtained in Step (I) to an annulation reaction.

7. A method for producing a compound represented by Formula (C'):

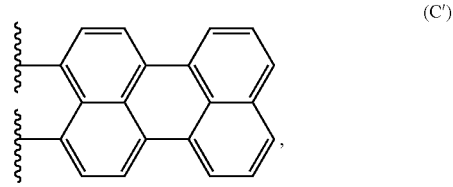 [SMILES: *c1ccc2c3cccc4cccc(c5ccc(*)c1c25)c43]

(C')

the method comprising the steps of:
(I) reacting a compound represented by Formula (B"):

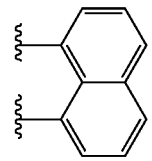

(B")

with a compound having a naphthalene skeleton in the presence of a palladium compound and o-chloranil to produce a compound having a structure represented by Formula (D"):

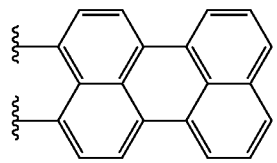
(D″)

and (II) subjecting the compound obtained in Step (I) to an annulation reaction.

8. The method according to claim 6, wherein step (II) is a step of performing an oxidation reaction using $FeCl_3$.

9. A method for producing a polycyclic aromatic compound substituted with at least one substituted or unsubstituted aryl group, the method comprising reacting a polycyclic aromatic compound with a substituted or unsubstituted aryl-containing compound in the presence of a palladium compound and o-chloranil.

10. The method according to claim 9, wherein the substituted or unsubstituted aryl-containing compound is an aryl-containing compound represented by Formula (E):

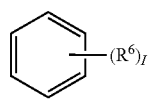
(E)

wherein $R^6$ may be the same or different, and each represents halogen, $C_{1-20}$ alkyl, $C_{1-20}$ alkoxy, $C_{3-50}$ cycloalkyl, or $C_{6-50}$ aryl; and l is an integer of 0 to 4, or an aryl-containing compound represented by Formula (E'):

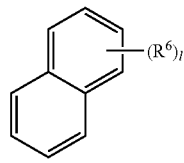
(E')

wherein $R^6$ and l are as defined above; and $R^6$ may bond to any of the benzene rings.

11. The method according to claim 9, wherein the polycyclic aromatic compound substituted with at least one substituted or unsubstituted aryl group is represented by Formula (D):

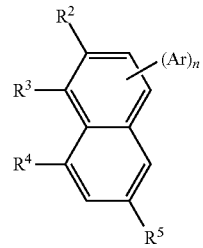
(D)

wherein $R^2$ to $R^5$ may be the same or different, and each represents hydrogen or $C_{1-20}$ alkyl, and Ar represents substituted or unsubstituted $C_{6-50}$ aryl and may bond to any of the cyclic structures, n is an integer of 1 to 4, and one of the following requirements (1) to (4) is satisfied:
(1) $R^2$ to $R^5$ are each hydrogen;
(2) $R^2$ and $R^5$ are each hydrogen; $R^3$ and $R^4$ bond to each other to form a 5- or 6-membered unsaturated ring; and the unsaturated ring may further have a monocyclic or fused aromatic ring fused thereto;
(3) $R^2$ and $R^3$ bond to each other to form a substituted or unsubstituted aromatic ring; $R^4$ is hydrogen; and $R^5$ is hydrogen or $C_{1-20}$ alkyl;
(4) $R^2$ and $R^3$ bond to each other to form a substituted or unsubstituted aromatic ring; $R^3$ and $R^4$ bond to each other to form a substituted or unsubstituted aromatic ring; and $R^5$ is hydrogen or $C_{1-20}$ alkyl, and
the polycyclic aromatic compound is a compound represented by Formula (B):

[Chem. 16]

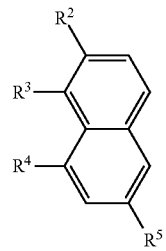

wherein $R^2$ to $R^5$ are as defined above.

12. The method according to claim 9, wherein the reaction of the polycyclic aromatic compound with the aryl-containing compound is performed in the presence of a silver compound.

13. The method according to claim 12, wherein the silver compound is silver trifluoromethanesulfonate.

14. The method according to claim 7, wherein step (II) is a step of performing an oxidation reaction using $FeCl_3$.

\* \* \* \* \*